US012642559B2

(12) United States Patent (10) Patent No.: US 12,642,559 B2
Vasta et al. (45) Date of Patent: Jun. 2, 2026

(54) TARSOMETATARSAL JOINT ARTHRODESIS TOOLS AND RELATED METHODS FOR BUNION CORRECTION

(71) Applicant: Gramercy Extremity Orthopedics LLC, Richardson, TX (US)

(72) Inventors: Paul J. Vasta, Richardson, TX (US); Scott Campbell, Richardson, TX (US); Edward A. Lebrija, Richardson, TX (US)

(73) Assignee: GRAMERCY EXTREMITY ORTHOPEDICS LLC, Richardson, TX (US)

( * ) Notice: Subject to any disclaimer, the term of this patent is extended or adjusted under 35 U.S.C. 154(b) by 0 days.

(21) Appl. No.: 19/145,726

(22) PCT Filed: Jan. 19, 2024

(86) PCT No.: PCT/US2024/012137
§ 371 (c)(1),
(2) Date: Jul. 3, 2025

(87) PCT Pub. No.: WO2024/158642
PCT Pub. Date: Aug. 2, 2024

(65) Prior Publication Data
US 2026/0114903 A1 Apr. 30, 2026

Related U.S. Application Data

(60) Provisional application No. 63/471,522, filed on Jun. 7, 2023, provisional application No. 63/446,445, filed
(Continued)

(51) Int. Cl.
A61B 17/56 (2006.01)
A61B 17/15 (2006.01)
A61B 17/68 (2006.01)

(52) U.S. Cl.
CPC ............ *A61B 17/56* (2013.01); *A61B 17/151* (2013.01); *A61B 2017/565* (2013.01); *A61B 2017/681* (2013.01)

(58) Field of Classification Search
CPC . A61B 17/56; A61B 17/151; A61B 2017/565; A61B 2017/681; A61B 17/1775; A61B 17/8866; A61B 2017/564
See application file for complete search history.

(56) References Cited

U.S. PATENT DOCUMENTS 4,718,413 A 1/1988 Johnson
4,729,369 A 3/1988 Cook
(Continued)

FOREIGN PATENT DOCUMENTS

AU 2014200305 A1 2/2014
GB 2589960 A 6/2021

OTHER PUBLICATIONS

International Search Report and Written Opinion in Application No. PCT/US2024/012137 dated Jun. 13, 2024.

*Primary Examiner* — Samuel S Hanna
(74) *Attorney, Agent, or Firm* — Panitch Schwarze Belisario & Nadel LLP

(57) ABSTRACT

A kit for conducting a tarsometatarsal joint arthrodesis to orient a first metatarsal relative to a medical cuneiform includes a metatarsal cut guide having a positioning paddle and a cut guide slot, four wires, a cuneiform cut guide having a second locking mechanism, a third locking mechanism, a cuneiform cut guide slot and an alignment guide and a compression-distraction tool having a first sliding member, a second sliding member, a fourth locking mechanism associated with the first sliding member and a fifth locking mechanism associated with the second sliding member. The positioning paddle positioned substantially parallel to the
(Continued)

cut guide slot. The metatarsal cut guide including a first locking mechanism.

21 Claims, 31 Drawing Sheets

Related U.S. Application Data on Feb. 17, 2023, provisional application No. 63/440,748, filed on Jan. 24, 2023.

(56) References Cited

U.S. PATENT DOCUMENTS

| | | | |
|---|---|---|---|
| 5,042,983 A | 8/1991 | Rayhack |
| 5,176,685 A | 1/1993 | Rayhack |
| 5,458,602 A | 10/1995 | Goble et al. |
| 5,593,411 A | 1/1997 | Stalcup et al. |
| 5,843,085 A | 12/1998 | Graser |
| 6,007,535 A | 12/1999 | Rayhack et al. |
| 6,629,943 B1 | 10/2003 | Schroder |
| 8,083,746 B2 | 12/2011 | Novak |
| 8,282,645 B2 | 10/2012 | Lawrence et al. |
| 8,753,348 B2 | 6/2014 | DiDomenico et al. |
| 9,622,805 B2 | 4/2017 | Santrock et al. |
| 9,687,250 B2 | 6/2017 | Dayton et al. |
| 9,936,994 B2 | 4/2018 | Smith et al. |
| 10,045,807 B2 | 8/2018 | Santrock et al. |
| 10,245,088 B2 | 4/2019 | Dayton et al. |
| 10,292,713 B2 | 5/2019 | Fallin et al. |
| 10,335,220 B2 | 7/2019 | Smith et al. |
| 10,342,590 B2 | 7/2019 | Bays et al. |
| 10,470,779 B2 | 11/2019 | Fallin et al. |
| 10,512,470 B1 | 12/2019 | Bays et al. |
| 10,524,808 B1 | 1/2020 | Hissong et al. |
| 10,555,757 B2 | 2/2020 | Dayton |
| 10,561,426 B1 | 2/2020 | Dayton et al. |
| 10,575,862 B2 | 3/2020 | Bays et al. |
| 10,582,936 B1 | 3/2020 | Hissong et al. |
| 10,603,046 B2 | 3/2020 | Dayton et al. |
| 10,610,241 B2 | 4/2020 | Wagner et al. |
| 10,646,263 B2 | 5/2020 | Lamm et al. |
| 10,743,995 B2 | 8/2020 | Fallin et al. |
| 10,849,631 B2 | 12/2020 | Hatch et al. |
| 10,849,663 B2 | 12/2020 | Dayton et al. |
| 10,849,670 B2 | 12/2020 | Santrock et al. |
| 10,874,446 B2 | 12/2020 | Smith et al. |
| 10,888,335 B2 | 1/2021 | Dayton et al. |
| 10,939,939 B1 | 3/2021 | Gil et al. |
| 10,945,764 B2 | 3/2021 | Dayton et al. |
| 11,020,148 B2 | 6/2021 | Hollis et al. |
| 11,039,873 B2 | 6/2021 | Santrock et al. |
| 11,076,863 B1 | 8/2021 | Bays et al. |
| 11,116,558 B2 | 9/2021 | Smith et al. |
| 11,147,590 B2 | 10/2021 | Dayton et al. |
| 11,154,340 B2 | 10/2021 | Dayton et al. |
| 11,185,359 B2 | 11/2021 | Smith et al. |
| 11,213,333 B2 | 1/2022 | Santrock et al. |
| 11,224,469 B2 | 1/2022 | Schumacher et al. |
| 11,278,337 B2 | 3/2022 | Bays et al. |
| 11,304,705 B2 | 4/2022 | Fallin et al. |
| 11,304,735 B2 | 4/2022 | Sayger et al. |
| 11,344,347 B2 | 5/2022 | Treace et al. |
| 11,389,221 B2 | 7/2022 | Tyber et al. |
| 11,439,415 B2 | 9/2022 | Cundiff et al. |
| 11,497,528 B2 | 11/2022 | Dayton et al. |
| 11,504,137 B2 | 11/2022 | Denham et al. |
| 11,523,845 B2 | 12/2022 | Dayton et al. |
| 11,547,425 B1 | 1/2023 | Lebrija et al. |
| 2008/0039850 A1 | 2/2008 | Rowley et al. |
| 2012/0016428 A1 | 1/2012 | White et al. |
| 2016/0213384 A1 | 7/2016 | Fallin et al. |
| 2017/0014143 A1 | 1/2017 | Dayton et al. |
| 2017/0042598 A1 | 2/2017 | Santrock et al. |
| 2019/0328435 A1* | 10/2019 | Bays .................... A61B 17/151 |
| 2020/0015856 A1 | 1/2020 | Treace et al. |
| 2020/0155176 A1 | 5/2020 | Bays et al. |
| 2020/0253641 A1 | 8/2020 | Treace et al. |
| 2021/0038212 A1 | 2/2021 | May et al. |
| 2021/0077120 A1 | 3/2021 | Hatch et al. |
| 2021/0077131 A1 | 3/2021 | Denham et al. |
| 2021/0093328 A1 | 4/2021 | Dayton et al. |
| 2021/0161246 A1 | 6/2021 | Lesser |
| 2021/0196324 A1 | 7/2021 | Dayton et al. |
| 2021/0251670 A1 | 8/2021 | Sayger et al. |
| 2021/0290250 A1 | 9/2021 | Denham et al. |
| 2021/0330311 A1 | 10/2021 | Denham et al. |
| 2021/0338450 A1 | 11/2021 | Hollis et al. |
| 2021/0369287 A1 | 12/2021 | Boffeli et al. |
| 2022/0151645 A1 | 5/2022 | Cundiff et al. |
| 2022/0361894 A1 | 11/2022 | Woodard et al. |

* cited by examiner

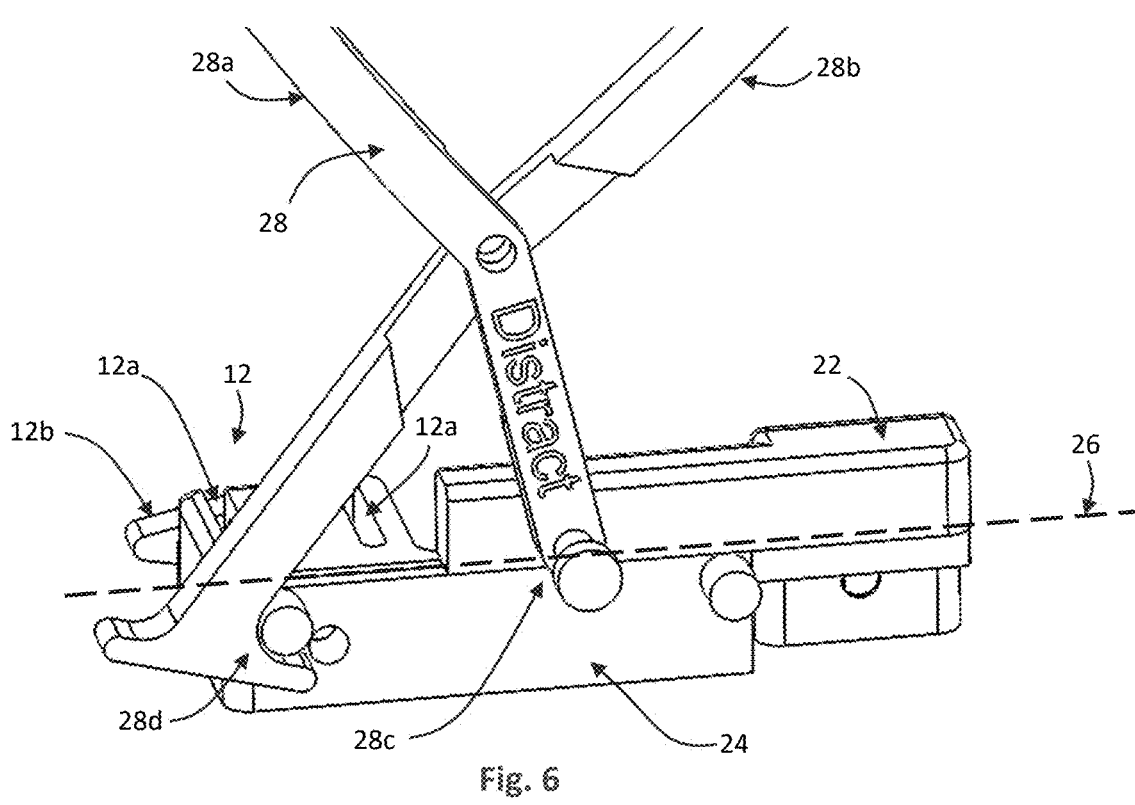
Fig. 6
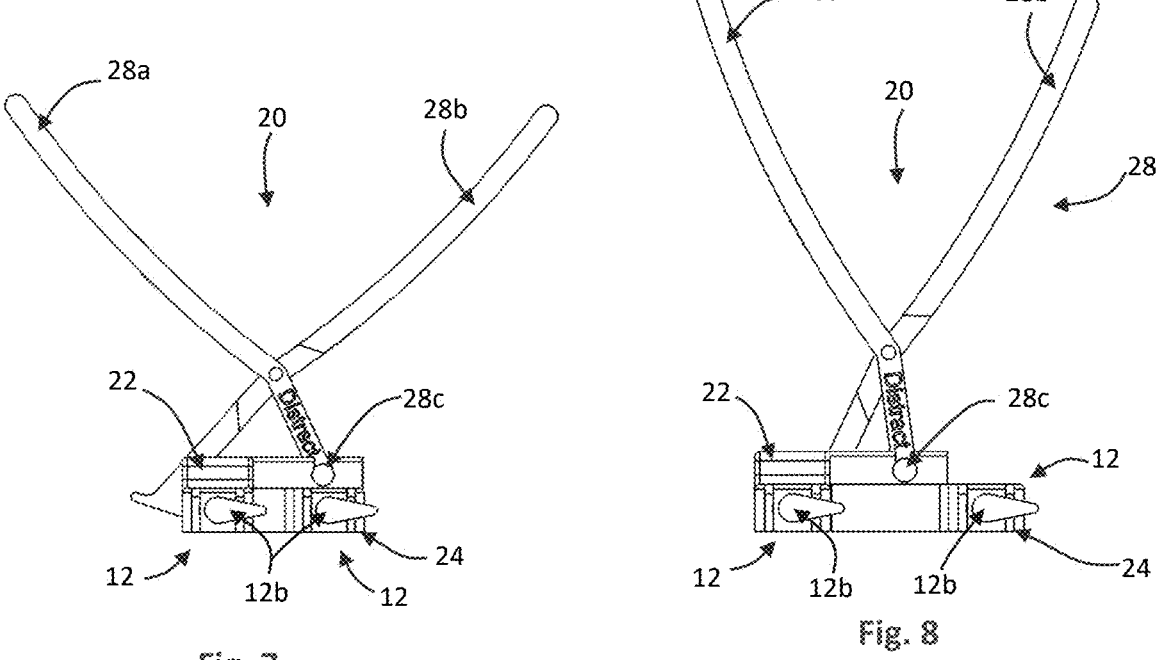
Fig. 7
Fig. 8

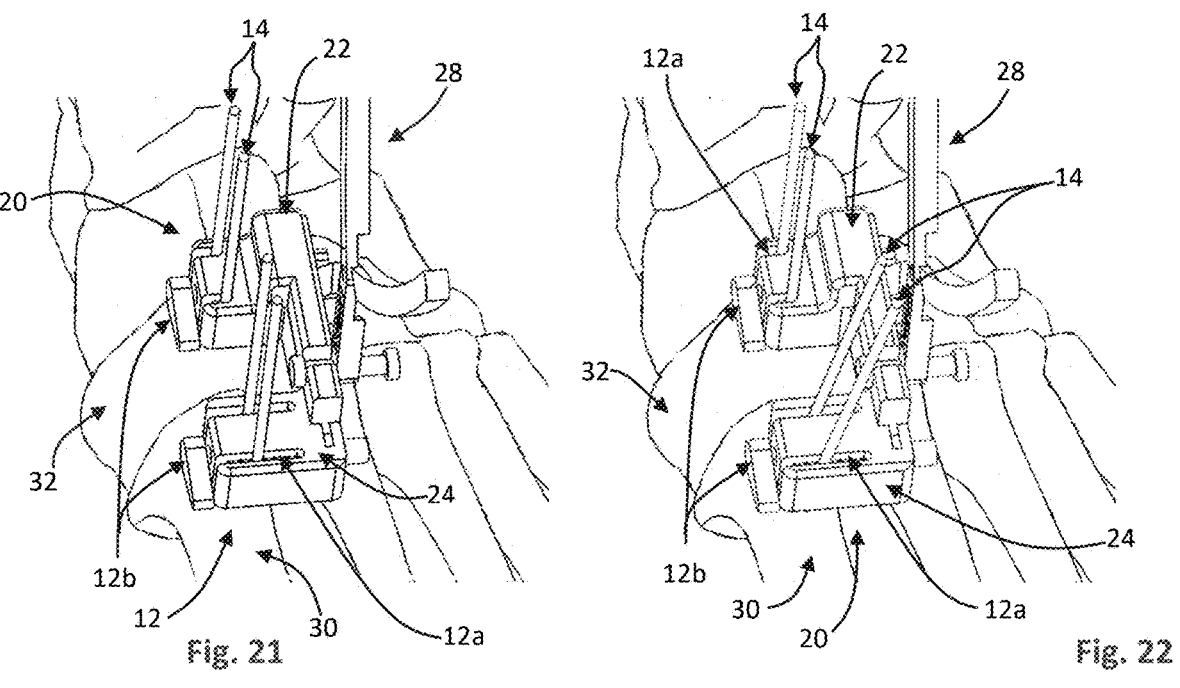
Fig. 21
Fig. 22
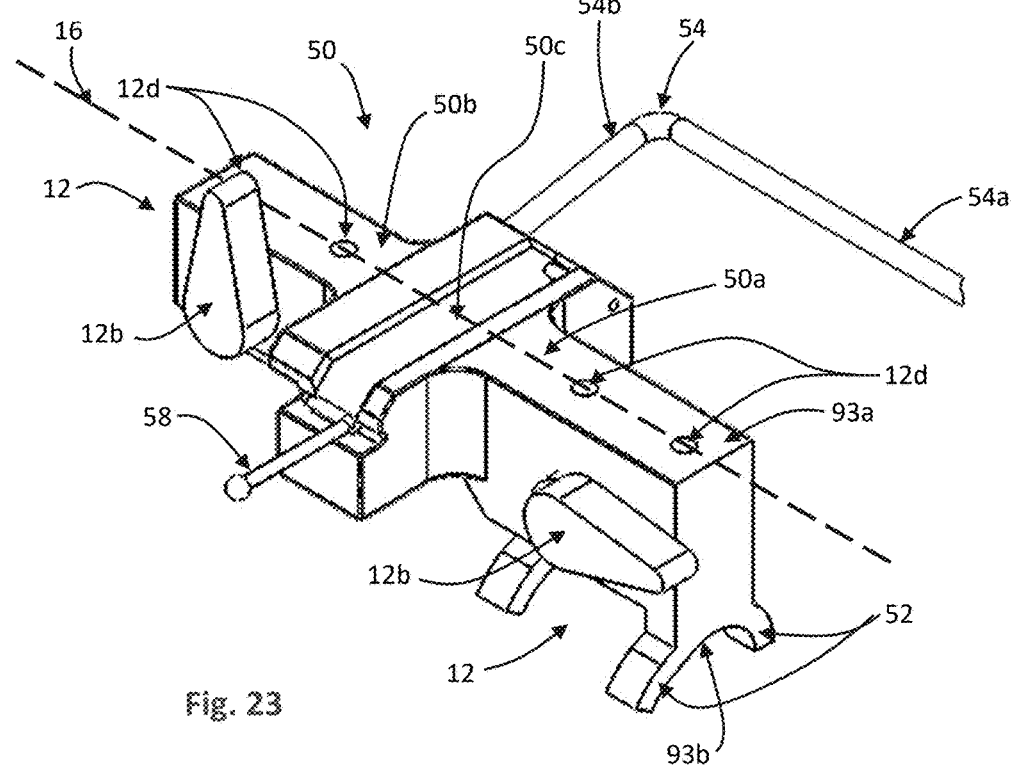
Fig. 23

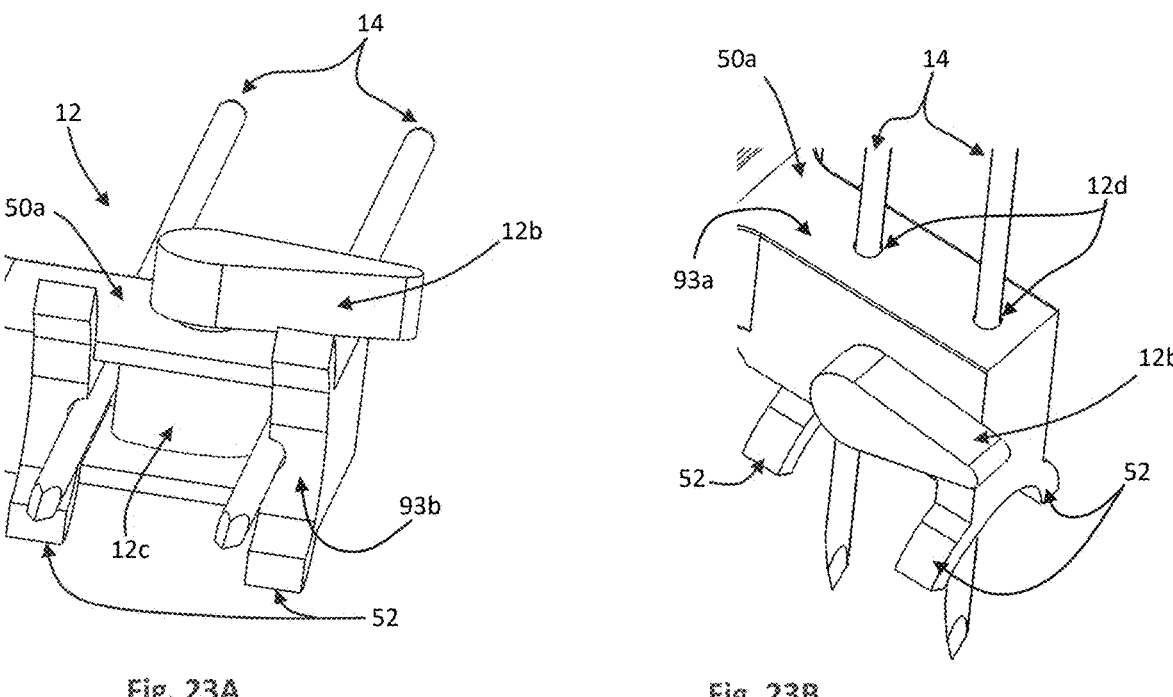
Fig. 23A
Fig. 23B
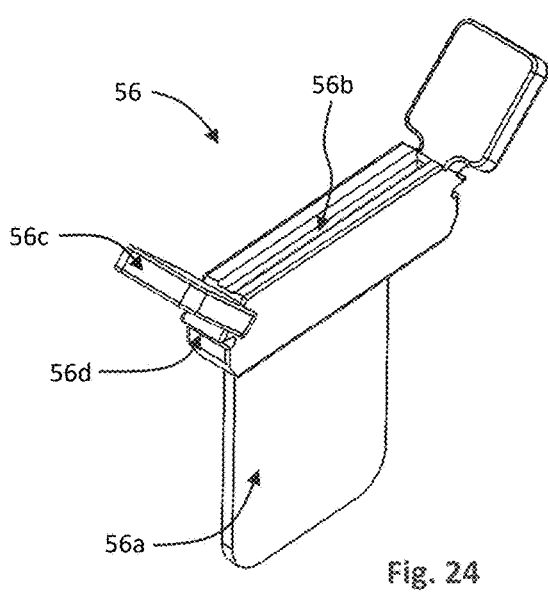
Fig. 24

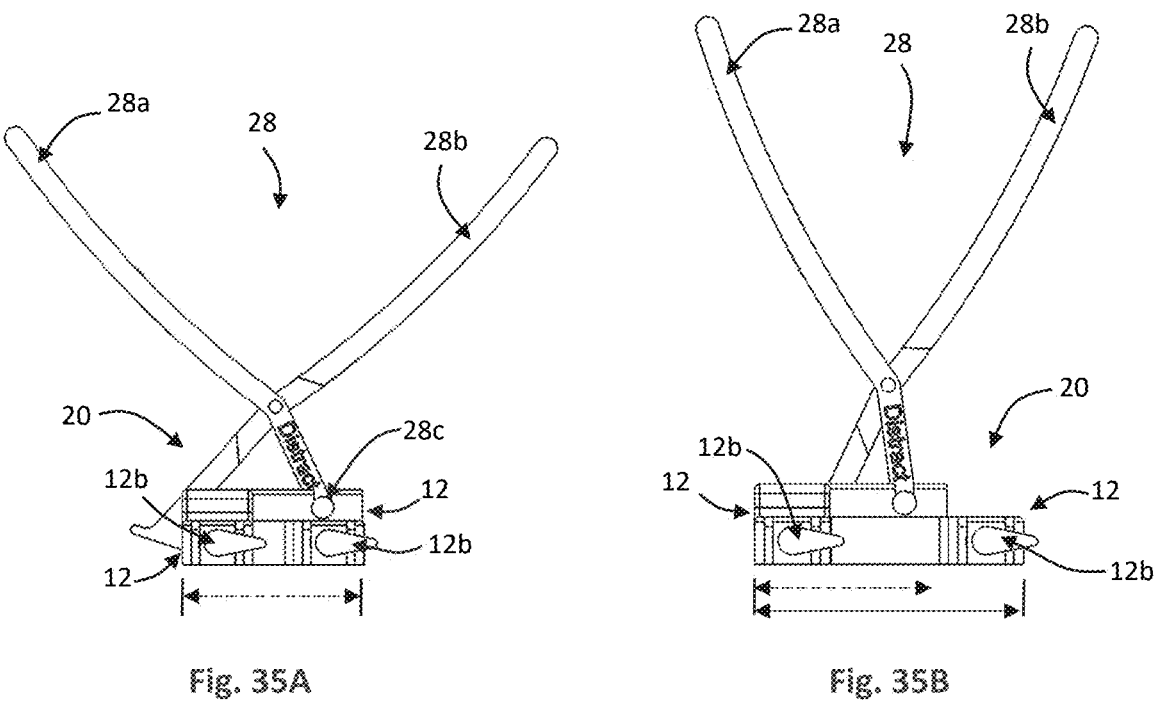
Fig. 35A
Fig. 35B
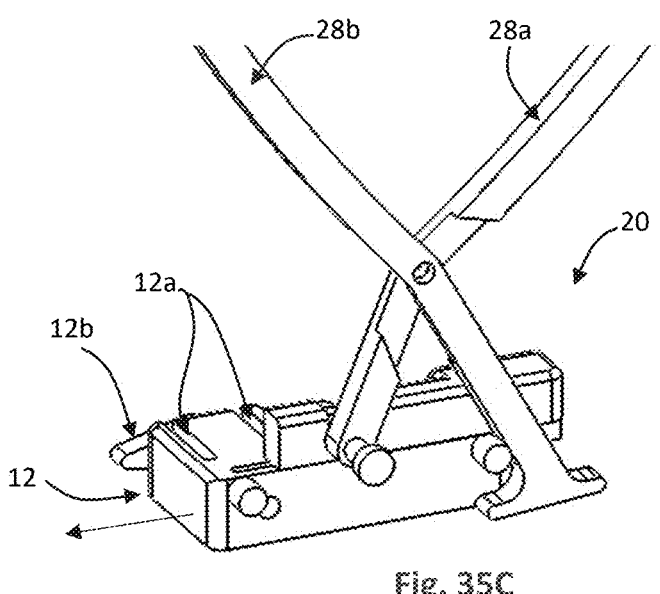
Fig. 35C

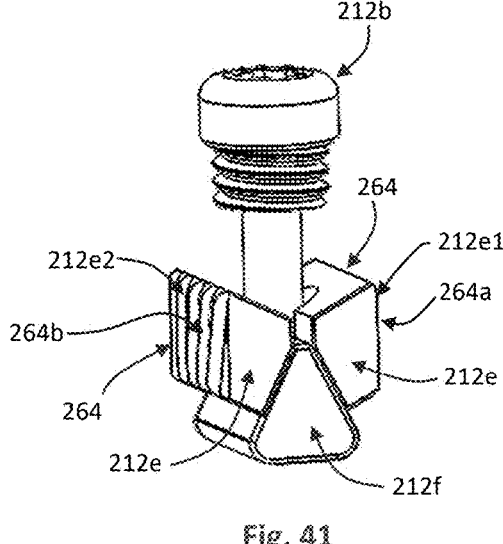
Fig. 41
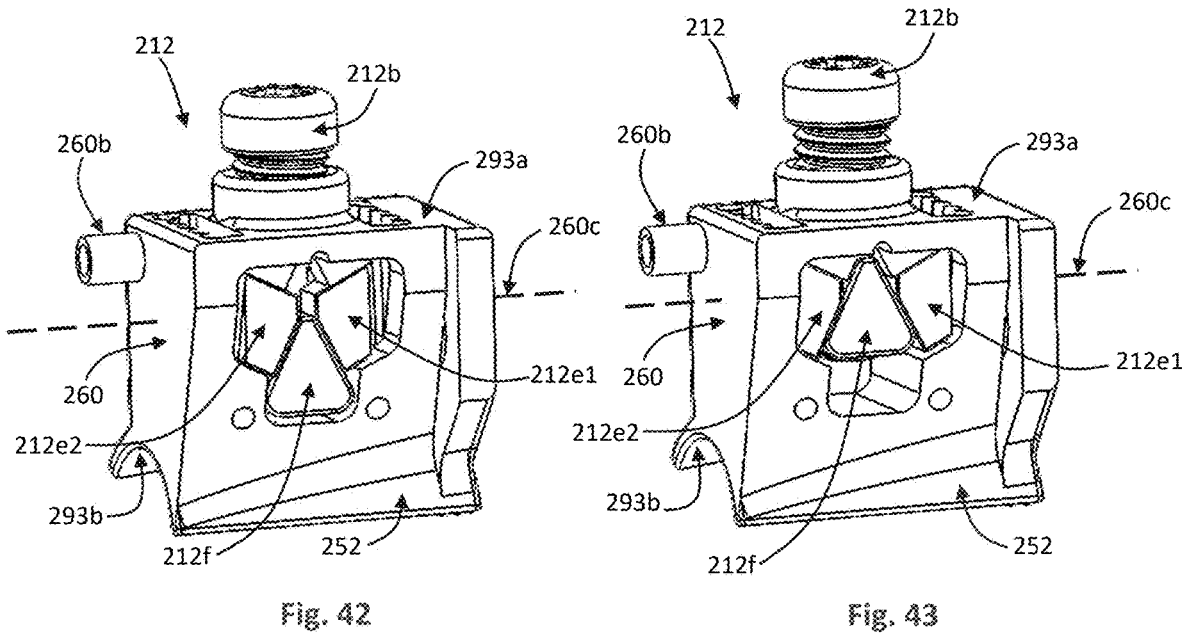
Fig. 42                    Fig. 43

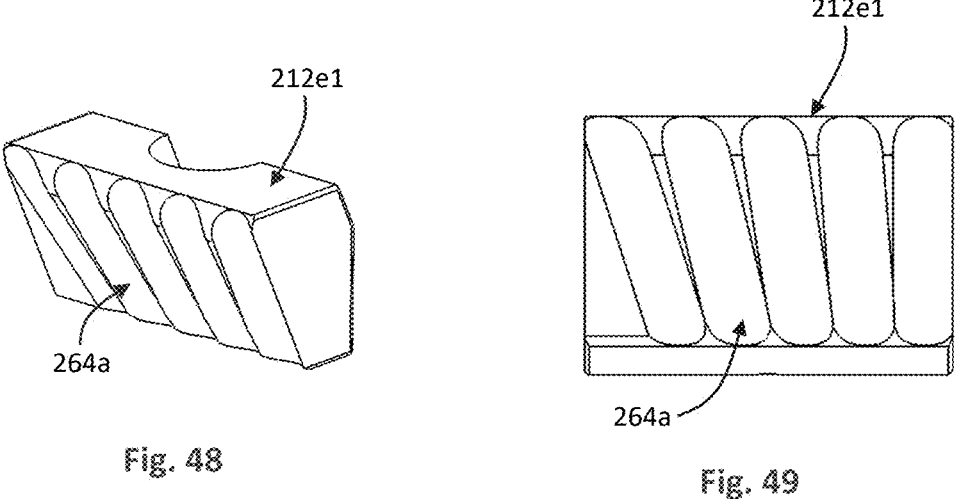
Fig. 48
Fig. 49
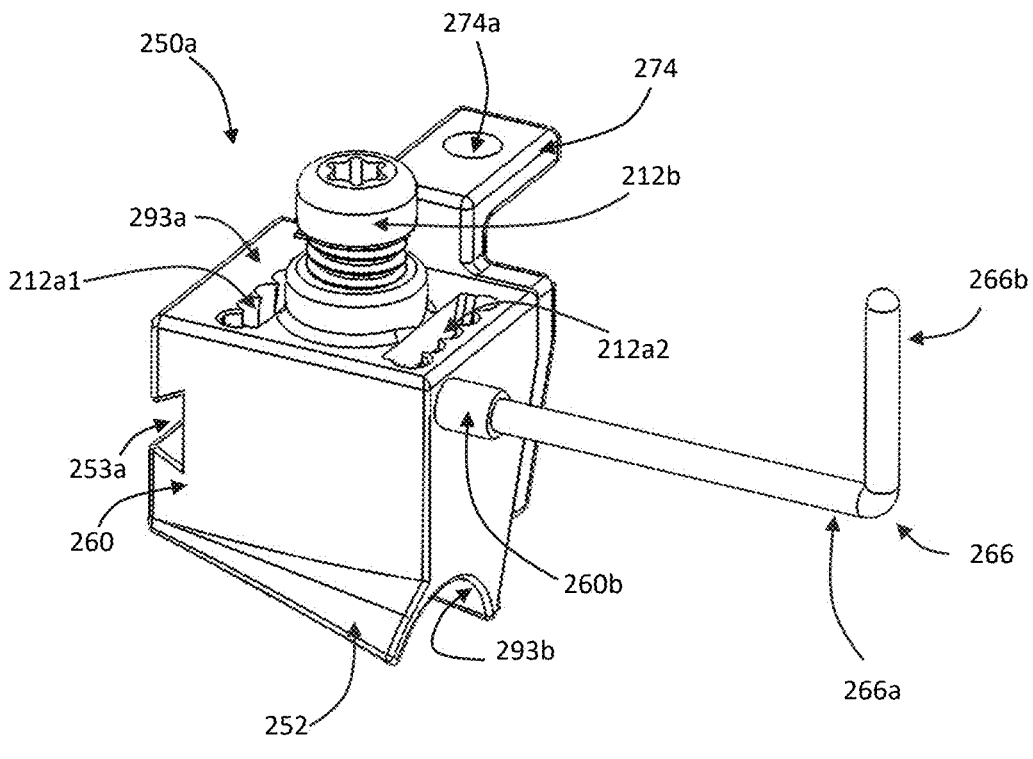
Fig. 50

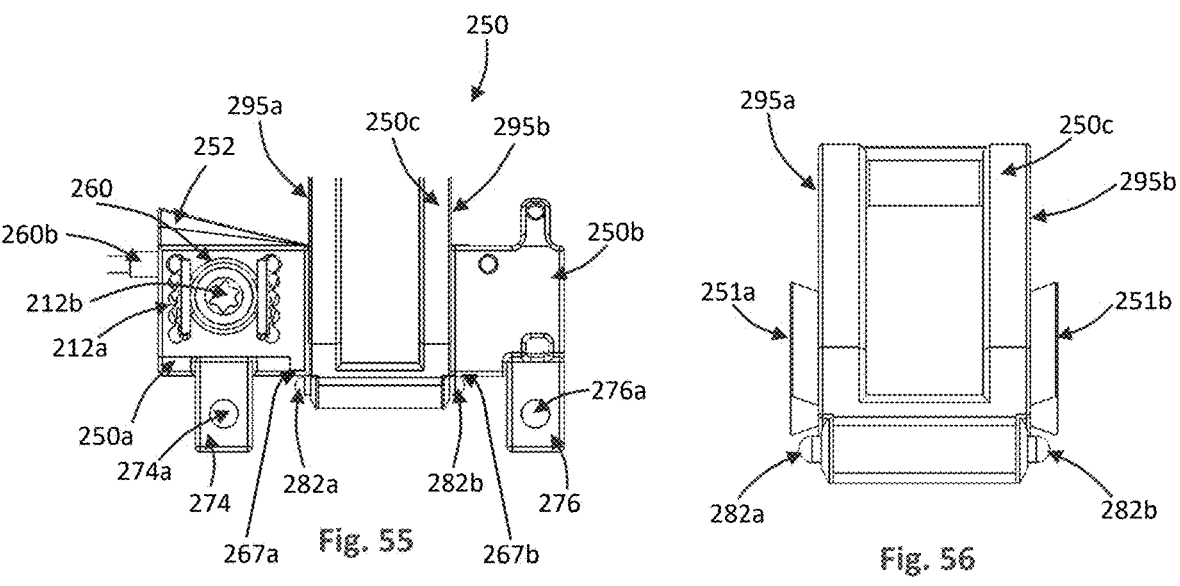
Fig. 55
Fig. 56
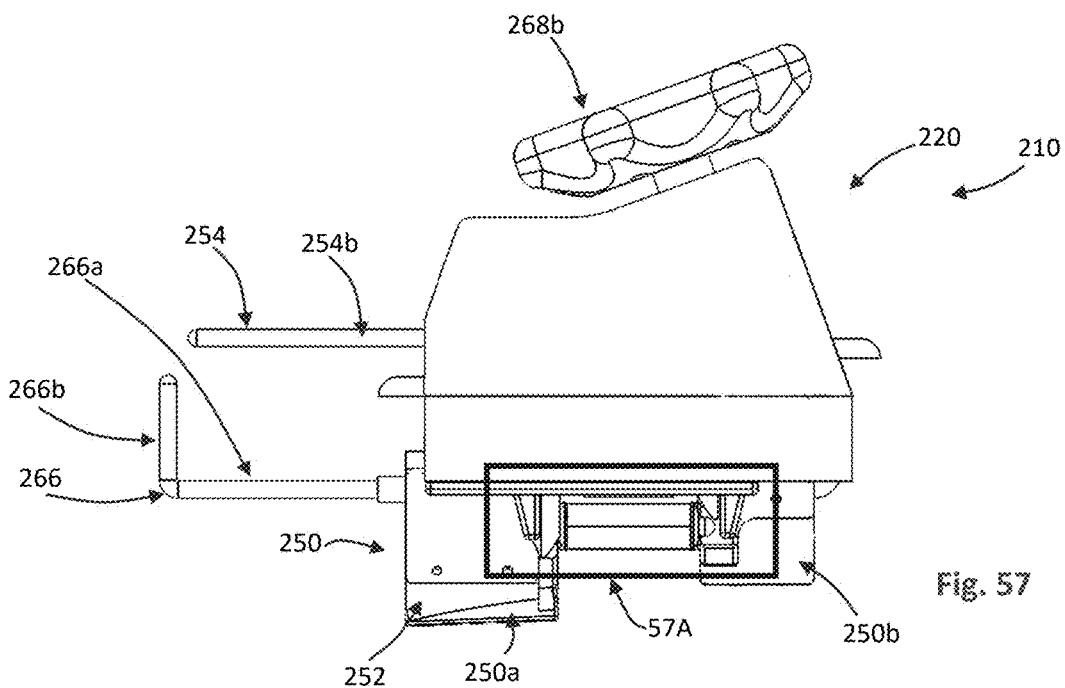
Fig. 57

250a        278d        250c        282b        278c        250b        250

296

210

268b

220

278b

254

250        254b

254a

294c

250b

212d

276

295b    250c 278a    266b

253b 266a    266

282a    293c    260    252    293b    266a
295a    251a    273d    253a    260b

250

TARSOMETATARSAL JOINT ARTHRODESIS TOOLS AND RELATED METHODS FOR BUNION CORRECTION

CROSS-REFERENCE TO RELATED APPLICATION

The present application is a U.S. national phase application under Section 371 of International Patent Application No. PCT/US2024/012137, filed Jan. 19, 2024 and titled, "Tarsometatarsal Joint Arthrodesis Tools and Related Methods for Bunion Correction," and claims the benefit of U.S. Provisional Patent Application Nos. 63/471,522; filed on Jun. 7, 2023; 63/446,445, filed on Feb. 17, 2023 and 63/440,748, filed on Jan. 24, 2023 and each titled "Tarsometatarsal Joint Arthrodesis Tools and Related Methods for Bunion Correction," the entire contents of which are incorporated herein by reference in their entirety.

BACKGROUND OF THE INVENTION

Bunion correction surgery involves the realignment of the first metatarsal from a deformed orientation to a normal or preferred anatomic alignment. This includes realignment of the first metatarsal generally within three degrees of motion. The first and primary being about an axis within the tarsometatarsal joint whereby the first metatarsal can be rotated toward the second metatarsal. The alignment between the two bones is commonly referred to as the intermetatarsal angle. The second degree of freedom is about the long axis of the metatarsal or rotation relative to the frontal plane. The third degree of freedom being a dorsal or plantar translation of the first metatarsal head, specifically if the first metatarsal is shortened during the procedure, to re-establish the plantar location of the first metatarsal head.

Many instruments and procedures have been developed to correct abnormal bunions. It would be desirable to design, develop and deploy instruments, tools and methods for bunion correction that are simple, reliable and accurate for use by surgeons.

BRIEF SUMMARY OF THE INVENTION

Briefly stated, the preferred invention is directed to the surgical repair of bones and specifically hallux valgus deformity correction, more commonly referred to as a bunion correction surgery leading to fusion of the tarsometatarsal ("TMT") joint.

The method of bunion correction described herein includes the utilization of tools for establishing removal of the joint surfaces of the bones such that the remaining bone surfaces are parallel planes after realignment of the first metatarsal relative to the medial cuneiform. This parallel plane configuration establishes a robust contact surface area that maintains the corrected alignment and promotes fusion after the bone ends are compressed at the joint.

A novel mechanism for securing surgical tools to surgical wires or pins inserted into bones is also described herein. In many orthopedic surgical cases, various instruments are needed to aid in the preparation and repair of bones. In certain situations, the instruments must be secured to one or more bones. Typically, one or more small rigid wires are inserted through holes in the instrument and then into the bone for this purpose. Often, at least one such wire is inserted at an angle oblique to the axis of another wire to secure the instrument from moving relative to the bone in multiple degrees of freedom.

However, this arrangement of wire attachment prevents the rapid removal or replacement of an instrument because one or more of the wires must be removed then re-inserted. Additionally, multiple removals and insertions of wires near or at the same location in the bone during a surgery may impact the structure and strength of the bone as well as reduce the rigidity of the wire connection to the bone. It is therefore advantageous to minimize or reduce the need for removal or replacement of wires for fixing instruments to bones.

In another aspect, a preferred embodiment of the present invention is directed to a method for conducting a tarsometatarsal joint arthrodesis to orient a first metatarsal relative to a medial cuneiform. The method includes securing a metatarsal scaffold to a dorsal side of the first metatarsal, positioning a cut guide with a positioning paddle in the tarsometatarsal joint and near a proximal end of the first metatarsal, cutting the proximal end of the first metatarsal with assistance of the cut guide, orienting the first metatarsal relative to the medial cuneiform and a second metatarsal, fixing a cuneiform scaffold to a dorsal side of the medial cuneiform and fixing the position of the first metatarsal relative to the medial cuneiform by fixing the cuneiform scaffold to the cuneiform. The metatarsal scaffold is connected to a cuneiform scaffold by a cut guide aperture. The cut guide is attachable to the cut guide aperture.

In an additional aspect, a preferred embodiment of the present invention is directed to a locking mechanism for securing an orthopedic device to a bone through wires. The locking mechanism includes a housing having a top surface and a bone contacting surface opposite the top surface. The housing defines a long locking axis. First and second slots extend between the top surface and the bottom surface through the housing. The first and second slots extend generally perpendicular to the long locking axis and have a slot length and a slot width. The first slot includes a first slot gripping surface and the second slot including a second slot gripping surface. A first locking lever and a second locking lever are positioned in the housing between the top and bone contacting surfaces. The first locking lever includes a first lock gripping surface and the second locking lever including a second lock gripping surface. The first slot gripping surface faces the first lock gripping surface and the second slot gripping surface faces the second lock gripping surface. A wedge is positioned between the first and second locking levers in the housing. An actuation mechanism is configured for manipulation by a user to move the wedge and the first and second locking levers such that the first lock gripping surface and the second lock gripping surface move at least along the long locking axis toward or away from the first and second slot gripping surfaces, respectively.

In a further aspect, a preferred embodiment of the present invention is directed to a first ray fixator for preparing a first metatarsal and a cuneiform for a bunion correction procedure. The first ray fixator includes a metatarsal scaffold having a housing with a top surface, a bone contacting surface and a first guide engagement surface. A cuneiform scaffold has a housing with a second guide engagement surface. The metatarsal scaffold and the cuneiform scaffold define a longitudinal axis of the first ray fixator. A cut guide aperture has a cut guide slot, a first cut engagement surface and a second cut engagement surface. The cut guide slot is oriented generally perpendicular to the longitudinal axis. The cut guide aperture is removably mountable to the metatarsal scaffold and the cuneiform scaffold by engaging the first guide engagement surface with the first cut engagement surface and the second guide engagement surface with the second cut engagement surface.

In another aspect, a preferred embodiment of the present invention is directed to a first ray fixator for preparing a first metatarsal and a cuneiform for a bunion correction procedure. The first ray fixator includes a metatarsal side, a cuneiform side and a cut guide aperture positioned between the metatarsal side and the cuneiform side. First and second metatarsal holes extend through the metatarsal side between a top surface and a bone contacting surface of the metatarsal side. First and second cuneiform holes extend through the cuneiform side between a top surface and a bone contacting surface of the cuneiform side. The first ray fixator also includes a longitudinal axis and an alignment arm having a longitudinal leg. The longitudinal leg is spaced laterally from the metatarsal side, the cuneiform side and the cut guide aperture. The longitudinal leg is oriented generally parallel to the longitudinal axis. The longitudinal leg is configured to orient the first metatarsal relative to a second metatarsal having a second metatarsal long axis.

In a further aspect, a preferred embodiment of the present invention is directed to a kit for preparing a first metatarsal and a cuneiform for a bunion correction procedure. The kit includes a first ray fixator having a metatarsal side and a cuneiform side and a compression-distraction tool having an actuation device and being releasably mountable to the metatarsal side and the cuneiform side. A longitudinal axis extends through the metatarsal and cuneiform sides. The metatarsal and cuneiform sides are movable relative to each other generally parallel to the longitudinal axis. The metatarsal side includes a metatarsal locking mechanism and the cuneiform side includes a cuneiform locking mechanism. The metatarsal locking mechanism is configured to releasably secure the metatarsal side to a metatarsal wire and the cuneiform locking mechanism is configured to releasably secure the cuneiform side to a cuneiform wire. The actuation device is configured to urge the metatarsal side toward or away from the cuneiform side when the compression-distraction tool is engaged with the metatarsal side and the cuneiform side.

In an additional aspect, a preferred embodiment of the present invention is directed to a kit for preparing a first metatarsal and a cuneiform for a bunion correction procedure. The kit includes a first ray fixator, a compression-distraction tool, a plurality of cut guides and a sterile package. The first ray fixator has a metatarsal side and a cuneiform side. The metatarsal side includes a metatarsal locking mechanism. The first ray fixator defines a longitudinal axis. The compression-distraction tool includes a first connecting member and a second connecting member. The first connecting member is configured to engage the metatarsal side and the second connecting member is configured to engage the cuneiform side. The plurality of cut guides is configured for removable mounting to the first ray fixator. The first ray fixator, compression-distraction tool and the plurality of cut guides are configured for delivery to a user in the sterile package.

In a further aspect, a preferred embodiment of the present invention is directed to a kit for conducting a tarsometatarsal joint arthrodesis to orient a first metatarsal relative to a medial cuneiform. The kit includes a metatarsal cut guide, four wires, a cuneiform cut guide and a compression-distraction tool. The metatarsal cut guide has a positioning paddle and a cut guide slot. The positioning paddle is positioned substantially parallel to the cut guide slot. The metatarsal cut guide includes a first locking mechanism. The cuneiform cut guide has a second locking mechanism, a third locking mechanism, a cuneiform cut guide slot and an alignment guide. The compression-distraction tool has a first sliding member, a second sliding member, a fourth locking mechanism associated with the first sliding member and a fifth locking mechanism associated with the second sliding member.

BRIEF DESCRIPTION OF THE SEVERAL VIEWS OF THE DRAWINGS

The foregoing summary, as well as the following detailed description of preferred embodiments of the instrument, implant and method of the preferred present invention, will be better understood when read in conjunction with the appended drawings. For the purposes of illustrating the tarsometatarsal joint arthrodesis tool and related methods, there are shown in the drawings preferred embodiments. It should be understood, however, that the application is not limited to the precise arrangements and instrumentalities shown. In the drawings:

FIG. 6 illustrates an opposite side perspective, magnified and partially broken view of the compression-distraction tool and compression distraction handle of FIG. 4;

FIG. 7 illustrates and alternate side perspective view of the compression-distraction tool and compression-distraction handle of FIG. 4;

FIG. 8 illustrates a further alternative side perspective view of the compression-distraction tool and compression-distraction handle of FIG. 4;

FIG. 21 illustrates a top perspective view of the compression-distraction tool and the compression-distraction handle of FIG. 7 mounted to the patient's foot, wherein the wires attached to the first metatarsal and the medial cuneiform are aligned along a longitudinal axis;

FIG. 22 illustrates a top perspective view of the compression-distraction tool and the compression-distraction handle of FIG. 7 mounted to the patient's foot, wherein the first metatarsal is rotated relative to the medial cuneiform with the wires attached to the first metatarsal unlocked relative to the locking mechanism and the prepared surfaces of the proximal end of the first metatarsal and the distal end of the medial cuneiform maintained in a generally parallel orientation as a result of the wires being constrained in their movement by slots in the locking mechanism;

FIG. 23 illustrates a top perspective view of a first ray fixator in accordance with the preferred embodiment of the present invention;

FIG. 23A illustrates a bottom perspective view of a metatarsal side of the first ray fixator of FIG. 23;

FIG. 23B illustrates a top perspective view of the metatarsal side of the first ray fixator of FIG. 23;

FIG. 24 illustrates a top perspective view of a cut guide for use with the first ray fixator of FIG. 23;

FIG. 35A illustrates a side perspective view of the compression-distraction tool of FIG. 7 and the compression-distraction handle of FIG. 4, wherein the compression-distraction tool and the compression-distraction handle are prepared for distraction;

FIG. 35B illustrates a side perspective view of the compression-distraction tool and the compression-distraction handle of FIG. 35A, wherein the compression-distraction handle is actuated to distract the bones;

FIG. 35C illustrates a magnified, opposite side perspective view of the compression-distraction tool and the compression-distraction handle of FIG. 35A, wherein the compression-distraction handle is actuated to distract the bones;

FIG. 41 illustrates a side perspective view of a portion of the internal locking mechanism of FIG. 39;

FIG. 42 illustrates a rear perspective view of the metatarsal scaffold of FIG. 39, wherein the internal locking mechanism is in an unlocked position;

FIG. 43 illustrates a rear perspective view of the metatarsal scaffold of FIG. 39, wherein the internal locking mechanism is in a locked position;

FIG. 48 illustrates a side perspective view of a scalloped gripping surface of levers of the locking mechanism of FIG. 39;

FIG. 49 illustrates a side elevational view of the scalloped gripping surface of FIG. 48;

FIG. 50 illustrates a top perspective view of the metatarsal scaffold of FIG. 39, including an alignment wire;

FIG. 55 illustrates a magnified top plan view of a portion of the first ray fixator of FIG. 38;

FIG. 56 illustrates a top plan view of a cut guide of the first ray fixator of FIG. 38;

FIG. 57 illustrates a side elevational view of the compressor-distractor of FIG. 37;

DETAILED DESCRIPTION OF THE INVENTION

Figure 1:
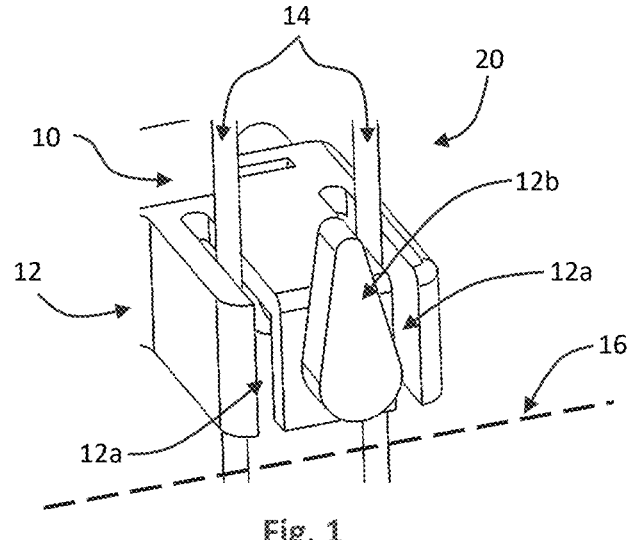
FIG. 1 illustrates a side perspective, broken view of a first preferred surgical instrument or compression-distraction tool, particularly focusing on a locking mechanism of the compression-distraction tool.

Certain terminology is used in the following description for convenience only and is not limiting. Unless specifically set forth herein, the terms "a", "an" and "the" are not limited to one element but instead should be read as meaning "at least one." The words "right", "left", "lower" and "upper" designate directions in the drawings to which reference is made. The words "inwardly" or "distally" and "outwardly" or "proximally" refer to directions toward and away from, respectively, the patient's body, or the geometric center of the preferred tarsometatarsal joint arthrodesis tools and related parts thereof. The words, "anterior", "posterior", "superior," "inferior", "lateral" and related words and/or phrases designate preferred positions, directions and/or orientations in the human body to which reference is made and are not meant to be limiting. The terminology includes the above-listed words, derivatives thereof and words of similar import.

It should also be understood that the terms "about," "approximately," "generally," "substantially" and like terms, used herein when referring to a dimension or characteristic of a component of the preferred invention, indicate that the described dimension/characteristic is not a strict boundary or parameter and does not exclude minor variations therefrom that are functionally the same or similar, as would be understood by one having ordinary skill in the art. At a minimum, such references that include a numerical parameter would include variations that, using mathematical and industrial principles accepted in the art (e.g., rounding, measurement or other systematic errors, manufacturing tolerances, etc.), would not vary the least significant digit.

Figure 2:
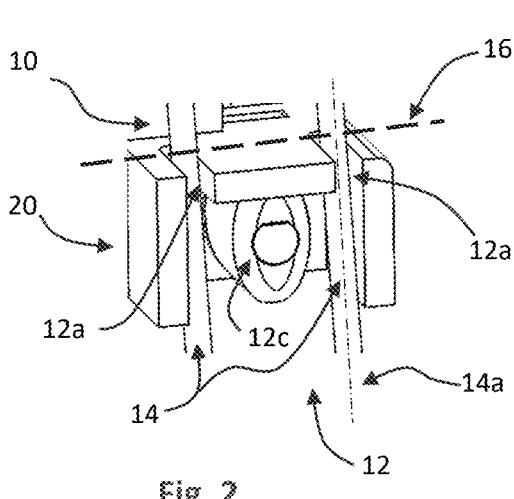
FIG. 2 illustrates a side perspective, broken view of the locking mechanism of the compression-distraction tool of FIG. 1, wherein an actuation mechanism and support structure are removed to clearly show locking bumpers of the locking mechanism in an open position.
Figure 3:
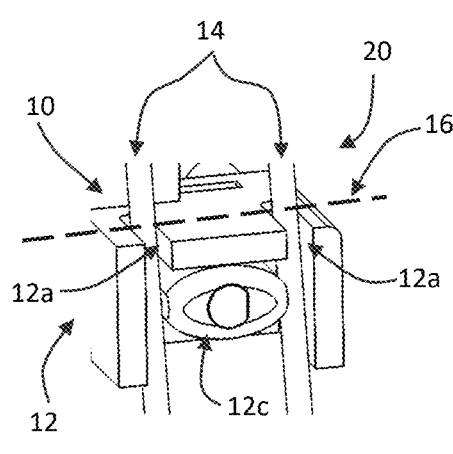
FIG. 3 illustrates a side perspective, broken view of the locking mechanism of the compression-distraction tool of FIG. 1, wherein the actuation mechanism and support structure are removed to clearly show locking bumpers of the locking mechanism in a locked position.

Referring to FIGS. 1-3, The mechanism of the preferred embodiment uses frictional force between a locking mechanism 12 of a surgical instrument, generally designated 10, which may be comprised of a compression-distraction tool 20, and bone wires, bone pins, K-wires, bone screws or other bone fasteners 14 to maintain the position of the instrument 10 relative the fasteners 14 within a plane generally defined by the slot 12a. The bone wires 14 described herein may be comprised of bone wires, bone pins, K-wires, bone screws or other bone fasteners 14 that are mounted to a bone and extend from the bone. The locking mechanism 12 applies a force against both wires 14, preferably simultaneously, along a vector approximately perpendicular to the long wire axis 14a defined by the wires 14. A first preferred example of the locking mechanism 12 associated with the surgical instrument 10 is shown in FIGS. 1-3 and may be associated with nearly any instrument 10 that is selectively attached and/or removed from wires 14 during a surgical procedure. The compression-distraction tool 20 of the first preferred embodiment is shown in FIG. 1 focusing on the locking mechanism 12 and in FIGS. 2 and 3 with an actuation mechanism 12b and support structure removed to show a locking bumper 12c that selectively engages the wires 14.

The locking mechanism 12 of the preferred embodiment facilitates sliding or moving the herein described instruments relative to or over one or more wires 14 or k-wires 14 that may be fixed in bone. The locking mechanism 12 may be actuated to the locked position to clamp onto the wire(s) 14 to restrict movement of the instruments relative to the locking mechanism 12, such as translation along the wire axis, thereby generally locking the wire(s) 14 to the locking mechanism 12 and the associated instrument. The preferred locking mechanism 12 includes the locking bumpers or cam 12c that is rotated by actuating the actuation mechanism 12b to impart a friction-lock between the k-wire(s) 14 and the walls of the locking bumpers 12c. The locking mechanism 12 is not limited to including the actuation mechanism 12b and the locking bumpers 12c and may be comprised of a screw threaded into the side wall of the housing of the locking mechanism 12 that presses directly against the wire 14 or against an insert that may, in turn, press against the wire 14.

The locking mechanism 12 of the preferred embodiment includes slots 12a through which the wires 14 may be inserted into the locking mechanism 12 thus allowing the instrument 10 to be placed onto the wires 14 along a direction at an angle relative to a longitudinal axis 16 defined by the wires 14. The locking mechanism 12 with the slots 12a preferably allows engagement of the locking mechanism 12 from a side of the wires 14 generally perpendicular to the longitudinal axis 16, however, the locking mechanism 12 is not so limited, as is described in further detail below. The slots 12a also facilitate engagement of the locking mechanism 12 with the wires 14 along the long wire axis 14a and at angled relative to the long wire axis 14a between perpendicular and vertical. Additionally, the instrument 10, preferably the compression-distraction tool 20 in the first preferred embodiment, may be locked onto the wires 14 at an angle relative to the longitudinal axis 16. The locking mechanism 12 also may include an actuation mechanism 12b with locking bumpers 12c that may be actuated from an open position where the locking bumpers 12c are spaced from the wires 14 (FIGS. 1 and 2) to a locked position where the locking bumpers 12c are engaged with the wires 14 (FIG. 3). In the open position, the actuation mechanism 12b and locking bumpers 12c allow insertion of the wires 14 into the slots 12a and in the locked position, the actuation mechanism 12b, specifically the locking bumpers 12c, engage and inhibit movement of the wires 14 relative to the locking mechanism 12 and the surgical instrument 10.

In an alternative embodiment (FIGS. 10-13), the locking mechanism 12 may include holes 12d through which the wires 14 are inserted allowing the instrument 10 to be placed onto the wires 14 by sliding the wires 14 through the holes 12d. In general, the locking mechanism 12 allows the instrument 10 to be secured to the wires 14 at any position along a length of the wires 14 such that the instrument 10 may be selectively positioned at a preferred distance from the bone. It is contemplated that other known means for creating a locking force can be implemented in the mechanism described herein for connecting the instrument 10 to the wires 14. The locking mechanism 12 may include fasteners, clamps, adhesive bonding, threaded connections, bayonet connections or other securing or locking mechanisms to connect the surgical instrument 10 to the wires 14. The locking mechanism 12 is not limited to connecting to two wires 14 that are secured to bones and may be designed and configured to connect to three or more wires 14 that are connected to a bone, bones or bone fragments to provide additional stability to the connection between the wires 14, the bones and the locking mechanism 12.

Figure 1A:
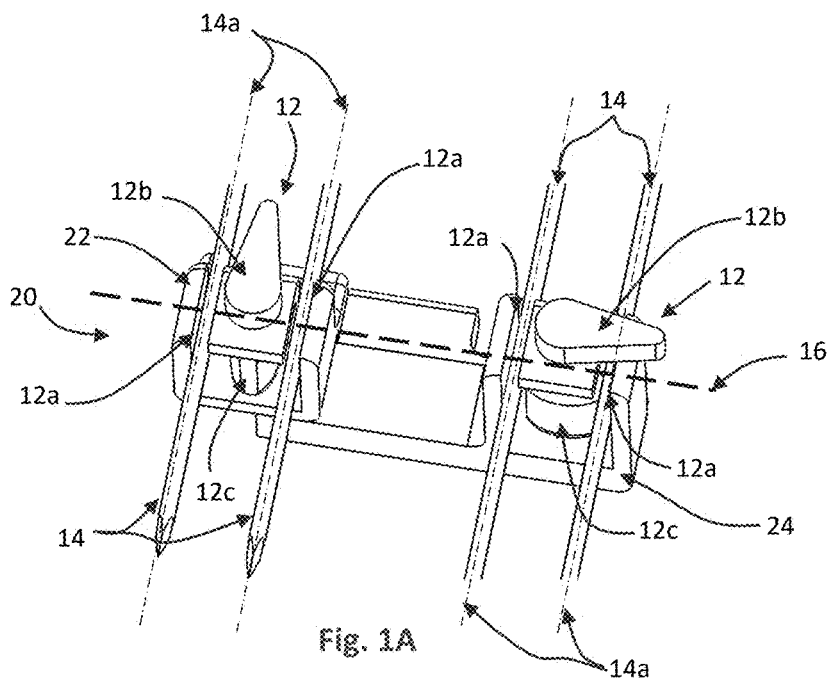
FIG. 1A illustrates a bottom perspective view of the compression-distraction tool of FIG. 1, mounted to four wires.

Referring to FIGS. 1A and 7-9, a second preferred instrument 20, preferably comprised of a compression-distraction tool 20, for compressing and/or distracting two bones relative to each other also utilizes the locking mechanisms 12. In many orthopedic surgical cases, a joint between two bones or a break in a single bone must be prepared for surgical fusion. Preparation of the surfaces between the bones is typically performed to encourage fusion and may require a gap between the bones to access the bone ends. Once the bone ends are prepared, the bone ends are compressed together to elicit bone fusion. Many tools are known in the art for both distracting and compressing bones at a joint or at two opposing prepared surfaces. The preferred embodiment of the second preferred instrument or compression-distraction tool 20 is intended to simplify the use and minimize the instrumentation required for compression and distraction of two bones or bone segments that are prepared for fusion. The second preferred instrument or compression-distraction tool 20 includes two sliding members 22, 24 that attach to wires 14 inserted into the bones of the joint, wherein each of the sliding members 22, 24 includes one of the locking mechanisms 12 discussed above. The sliding members 22, 24 are connected to each other in a manner that allows them to translate along a single degree of freedom or along a sliding axis 26, which is typically aligned with a long bone axis of the associated bone segments or a bone. Each sliding member 22, 24 includes one of the locking mechanisms 12 such that each member 22, 24 is attached to only one of the bones thereby allowing the sliding connection to draw the bones together or apart for compression or distraction. In FIG. 1A, the locking mechanism 12 associated with the first sliding member 22 is in the open position, allowing the wires 14 to move within the slots 12a, and the locking mechanism associated with the second sliding member 24 is in the locked position, fixing the second sliding member 24 to the wires 14 with the locking bumpers 12c engaged with the wires 14.

To apply force to the sliding members 22, 24, a preferred compression-distraction handle 28 is mounted at one side to the first sliding member 22 and at a second side to the second sliding member 24. The handle 28 includes two gripping members 28a, 28b and two connecting members 28c, 28d. The first connecting member 28c attaches to the first sliding member 22 in a manner that can apply force in either direction along the single degree of freedom the sliding connection allows or along the sliding axis 26. The second connecting member 28d attaches to the second sliding member 24 at one of two locations positioned at a distance from the first connecting member's 28c attachment location along the allowable single degree of freedom of the sliding connection or along the sliding axis 26.

Compression of the bones is achieved by attaching the first connecting member 28c to the first sliding member 22 and the second connecting member 28d to the second sliding member 24 at the location that is adjacent to the wire locking mechanism 12 of the second sliding member 24. By applying a compressive force to, i.e., squeezing, the gripping members 28a, 28b, the first and second connecting members 28c, 28d are drawn together. This action decreases the distance between the wire locking mechanisms 12 of the first and second sliding members 22, 24 and the first sliding member 22 thereby decreasing the distance between the wires 14 (not shown in FIGS. 4-6) of the first and second bones which results in compression.

Figure 4:
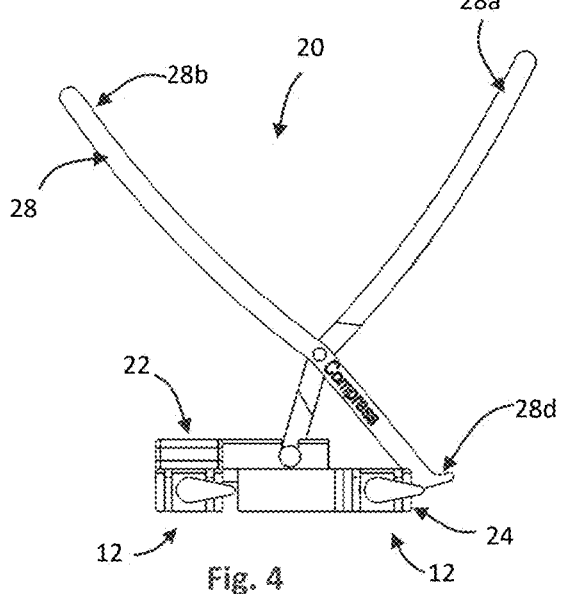
FIG. 4 illustrates a side elevational view of a second instrument or compression-distraction tool and a compression-distraction handle in a distracted position in accordance with a preferred embodiment of the present invention.
Figure 5:
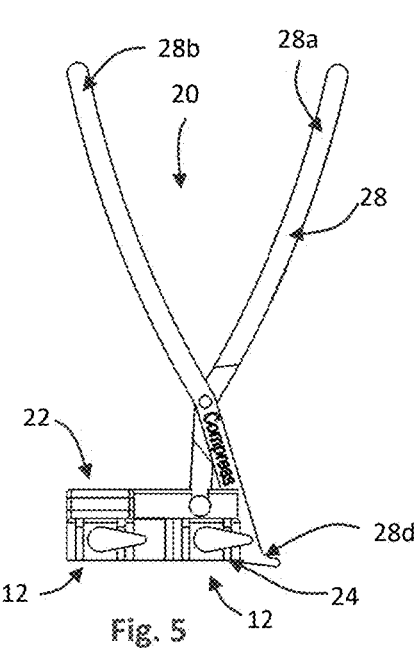
FIG. 5 illustrates a side elevational view of the compression-distraction tool and compression-distraction handle of FIG. 4 in a compressed position.
Figure 9:
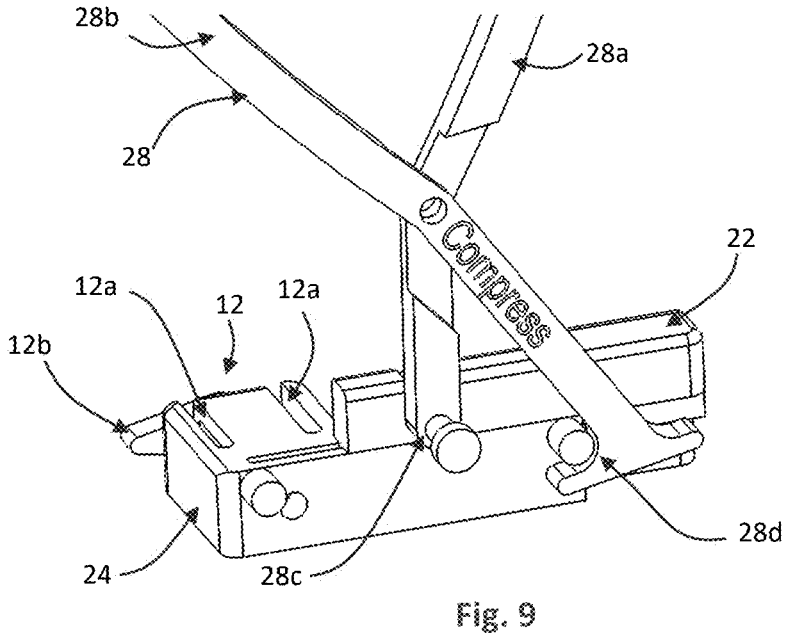
FIG. 9 illustrates an alternative opposite side perspective, magnified and partially broken view of the compression-distraction tool and compression distraction handle of FIG. 4.

Distraction of the bones is achieved by attaching the first connecting member 28c to the first sliding member 22 and the second connecting member 28d to the second sliding member 24 at the location that places the first connecting member 28c between the second connecting member 28d and the wire locking mechanism 12 of the second sliding member 24. By applying a compressive force to, i.e., squeezing, the gripping members 28a, 28b, the first and second connecting members 28c, 28d are drawn apart along the single degree of freedom of the sliding member connection. This action increases the distance between the wire locking mechanisms 12 of the second sliding member 24 and the first sliding member 22 thereby increasing the distance between the wires 14 (not shown in FIGS. 4-10) of the first and second bones which results in distraction. An example of the preferred embodiment for the compression configuration is shown in FIGS. 4-6 and the preferred embodiment for the distraction configuration is shown in FIGS. 7-9.

A ratcheting mechanism (not shown) bridging the gripping members 28a, 28b of the compression-distraction handle 28 may be incorporated such that when the desired amount of translation, either compressive or distractive, is attained, the position of the sliding members 22, 24 may be temporarily fixed, and the force applied to the gripping members 28a, 28b by the surgeon or technician may be removed. This temporary handle position locking feature of the ratcheting mechanism will allow the surgeon to release the compression-distraction handle 28 without losing the position of the bones relative to one another. Other mechanisms for temporarily fixing the position of the gripping members 28a, 28b relative to one another is contemplated for this purpose (not shown in the figures)

Referring to FIGS. 10-22, the preferred method for performing a bunion correction procedure with the metatarsal cut guide 29, the compression-distraction tool 20, tools having the locking mechanism 12 and other tools and instruments may include making an incision to expose the tarsometatarsal joint of the impacted foot, which is positioned between the first metatarsal 30 and the medial cuneiform 32. The tarsometatarsal joint between the first metatarsal 30 and the medial cuneiform 32 is prepared for correction whereby the tissues attaching the medial cuneiform 32 and the first metatarsal 30 and potentially additional soft tissue are severed to release the joint.

Figure 10:
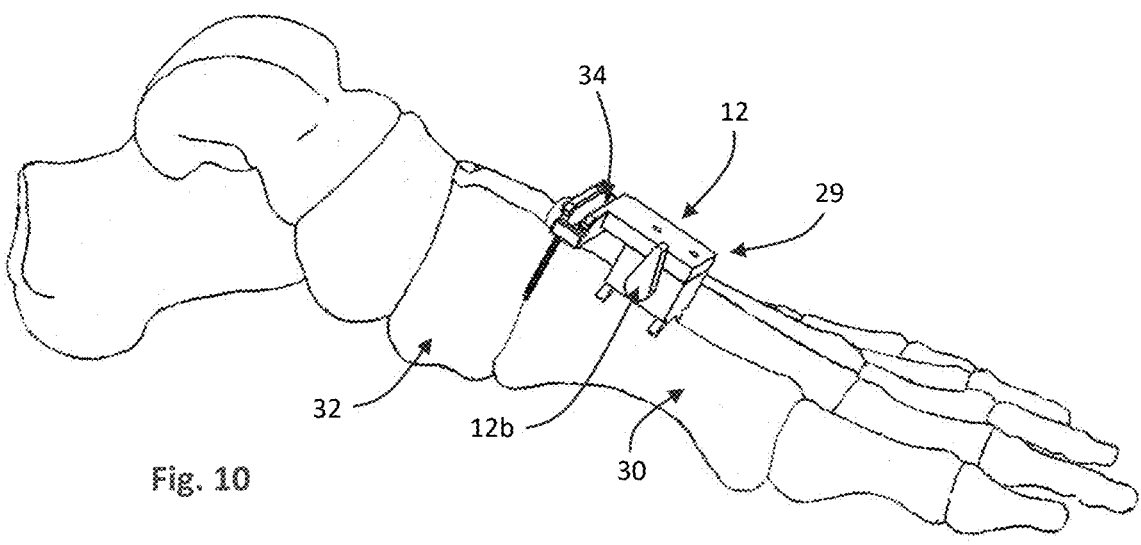
FIG. 10 illustrates a side perspective view of a metatarsal cut guide of the preferred embodiment, wherein the metatarsal cut guide is positioned on a first metatarsal of a patient's foot.
Figure 11:
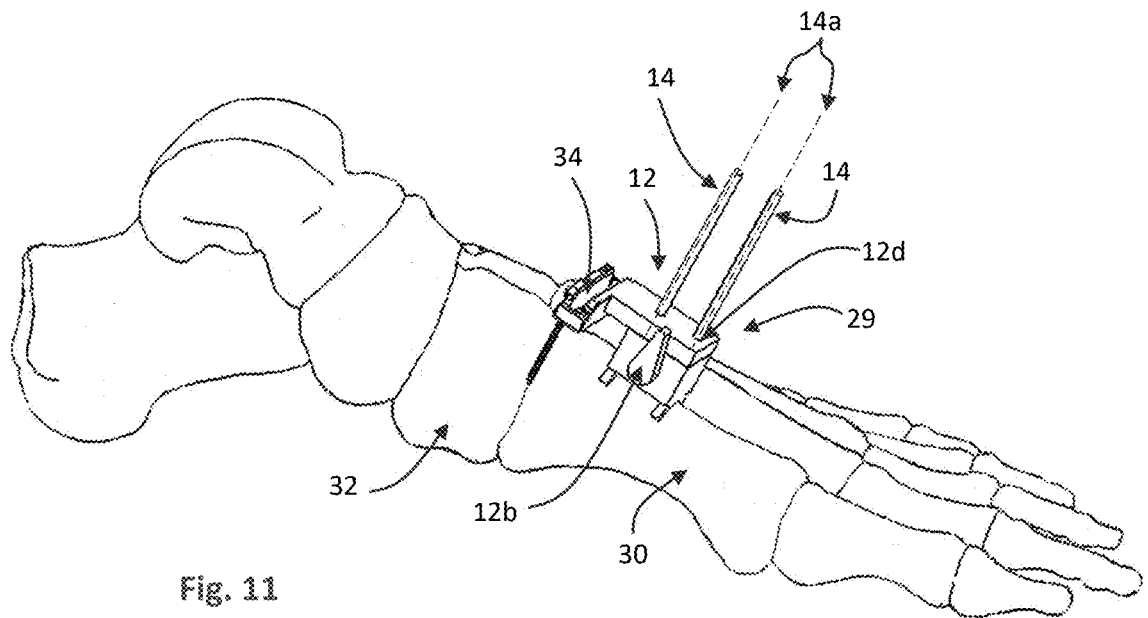
FIG. 11 illustrates a side perspective view of the metatarsal cut guide of FIG. 10, wherein wires are mounted to the first metatarsal and the wires are positioned in holes of the metatarsal cut guide.

In the preferred embodiment, the metatarsal cut guide 29 is placed on the dorsal aspect of the first metatarsal 30 with a positioning paddle 18 abutted against a base or proximal end of the first metatarsal 30. The long axis of the metatarsal cut guide 29 is manually aligned with the first metatarsal long axis 30a of the first metatarsal 30 and the surgical wires or pins 14 are inserted through the cut guide holes 12d then into the first metatarsal 30 to maintain the alignment and position of the metatarsal cut guide 29 with the first metatarsal 30 (FIG. 10-11).

Figure 12:
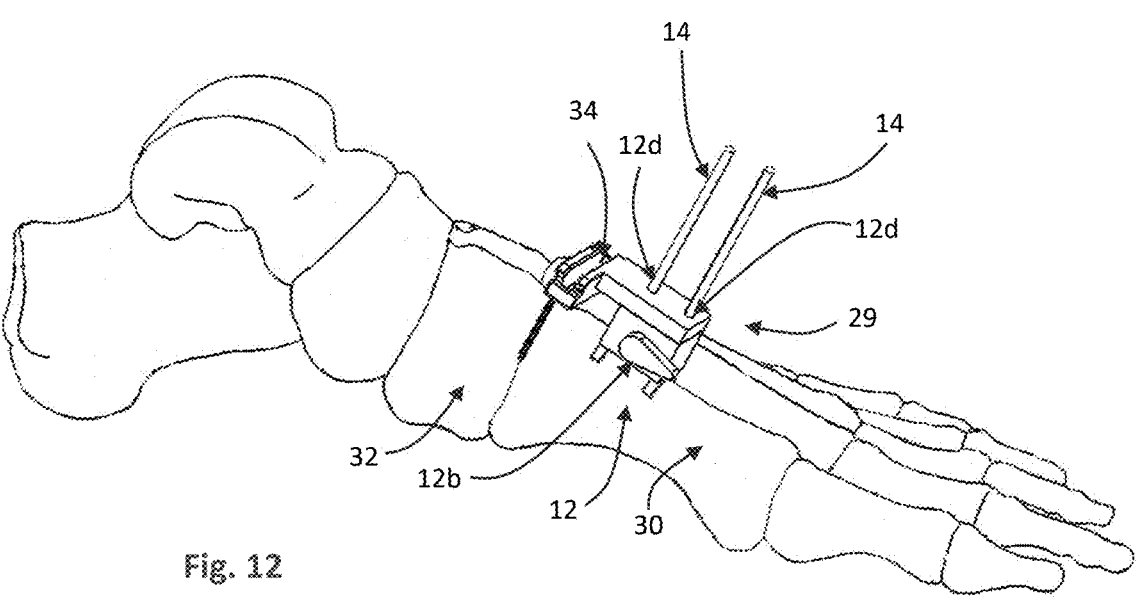
FIG. 12 illustrates a side perspective view of the metatarsal cut guide of FIG. 10, wherein a locking mechanism is positioned in a locked configuration.

The actuation mechanism 12b of the wire locking mechanism 12 of the metatarsal cut guide 29 is then actuated, thereby fixing the metatarsal cut guide 29 to the wires 14 and preventing motion along the longitudinal axis 16 and the long wire axis 14a of the wires 14. Actuation of the actuating mechanism 12b generally fixes the position of the metatarsal cut guide 29 relative to the first metatarsal 30 (FIG. 12). In the locked configuration, the locking bumpers 12c engage the wires 14 to secure the metatarsal cut guide 29 to the wires 14.

A saw blade (not shown) is inserted into a cut guide slot 34 of the metatarsal cut guide 29 and the joint surface of the metatarsal base or proximal end of the first metatarsal 30 is removed or prepared to have a generally planar surface that is perpendicular to the longitudinal axis 16. (Not shown in the figures) The cut guide slot 34 of the metatarsal cut guide 29 is configured such that the saw blade is oriented to cut along a plane perpendicular to the longitudinal axis 16 such that the prepared surface is perpendicular to a long axis of the first metatarsal 30.

Figure 13:
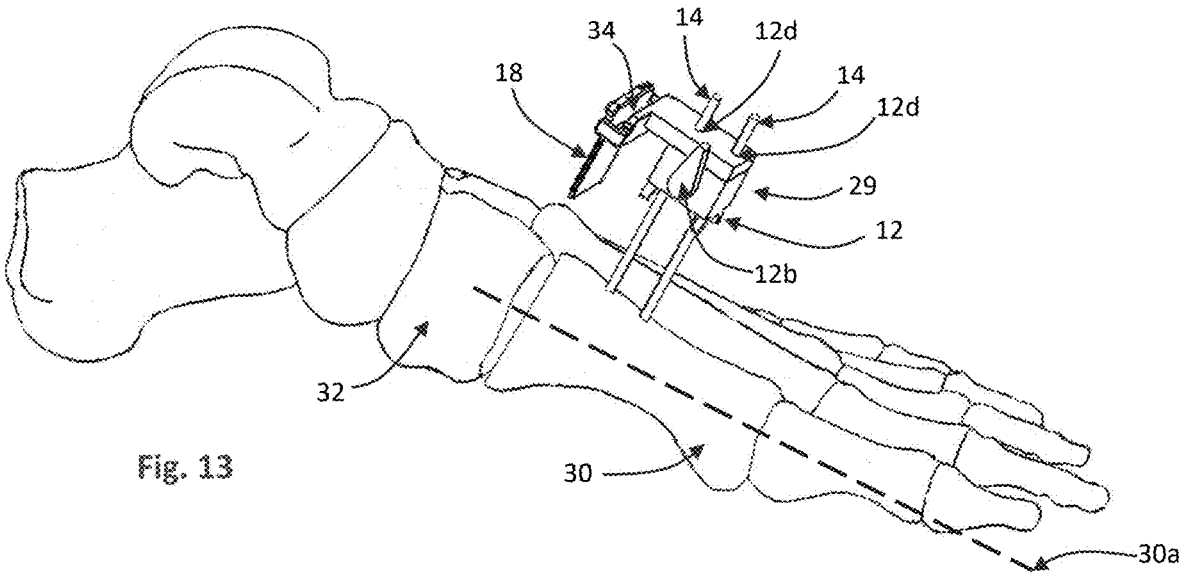
FIG. 13 illustrates a side perspective view of the metatarsal cut guide of FIG. 10, wherein the metatarsal cut guide is moved upwardly on the wires.

The wire locking mechanism 12 of the metatarsal cut guide 29 is then unlocked by actuating the actuation mechanism 12b to disengage the locking bumpers 12c from the wires 14, thereby freeing the metatarsal cut guide 29 to move relative to the wires 14, and the metatarsal cut guide 29 is translated along the long wire axis 14a of the wires 14 and removed (FIG. 13).

Figure 14:
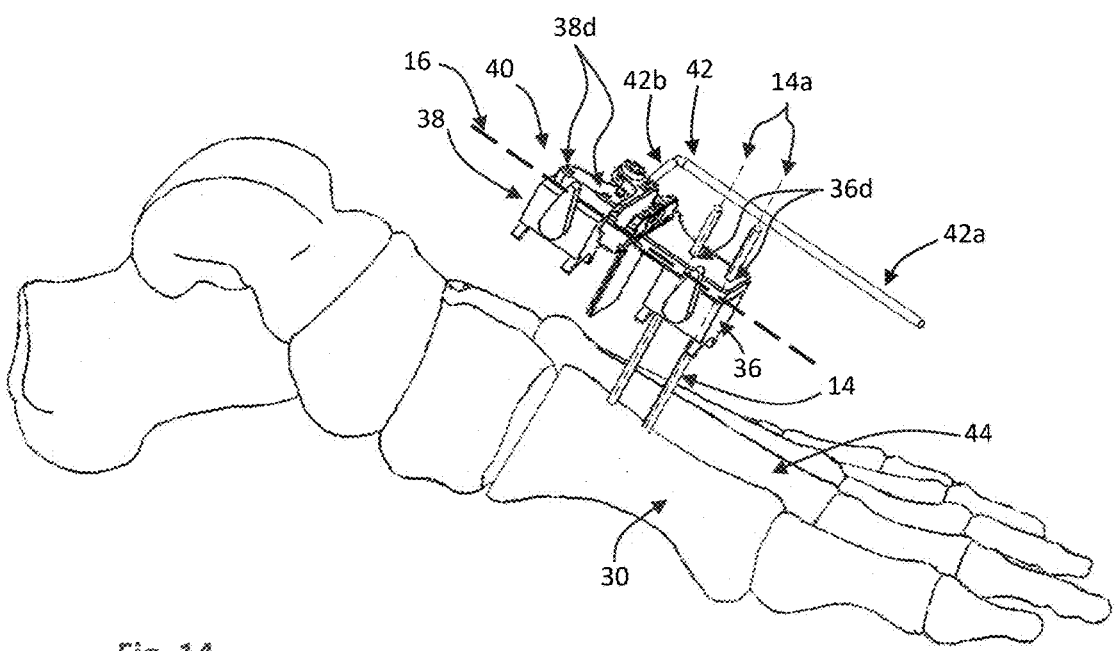
FIG. 14 illustrates a side perspective view of a preferred cuneiform cut guide, wherein the cuneiform cut guide is positioned on the wires.

A cuneiform cut guide 40 is then placed onto the wires 14 that are connected to the first metatarsal 30 by passing the wires 14 through a first locking mechanism or metatarsal scaffold 36 and holes 36d in the first locking mechanism or metatarsal scaffold 36 of the cuneiform cut guide 40. The cuneiform cut guide 40 is then translated down the wires 14 to the dorsal surface of the first metatarsal 30. The locking mechanism 36, which is similarly designed and configured as the locking mechanism 12, is then actuated by manipulating an actuation mechanism 36b to lock the cuneiform cut guide 40 to the pins or wires 14 in the first metatarsal 30 (FIG. 14).

Figure 15:
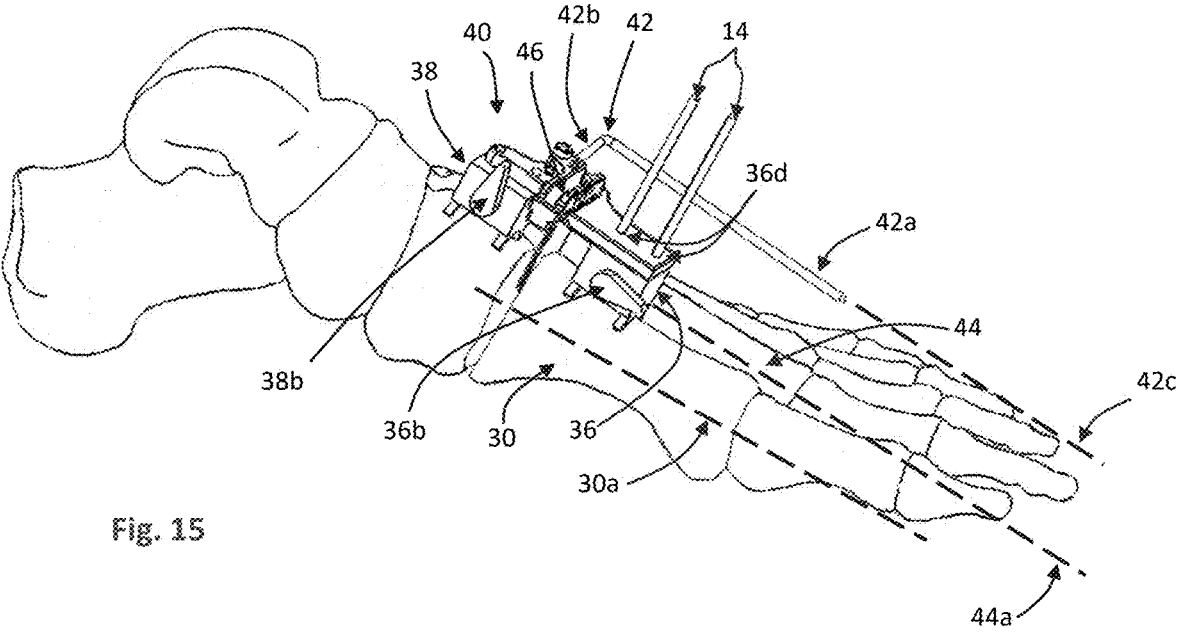
FIG. 15 illustrates a side perspective view of the cuneiform cut guide of FIG. 14, wherein the cuneiform cut guide is positioned on the first metatarsal and a medial cuneiform of the patient.

Manual force is then applied by the surgeon against the first metatarsal 30 to correct the intermetatarsal angle by aligning an alignment guide or arm 42 having a longitudinal arm 42a, a lateral leg or arm 42b and an alignment guide axis 42c of the cuneiform cut guide 40 with a second metatarsal long axis 44a of a second metatarsal 44. This manual manipulation of the positioning of the first metatarsal 30 relative to the medial cuneiform 32 is conducted after the proximal or base surface of the first metatarsal 30 is cut and prepared, but before the cuneiform cut guide 40 is connected to cut and prepare the distal end of the medial cuneiform 32. Rotation of the first metatarsal 30 about a first metatarsal long axis 30a of the first metatarsal 30 may also be achieved during this step by applying a manual force to the first metatarsal 30 for rotation about a first metatarsal long axis 30a (FIG. 15).

Figure 16:
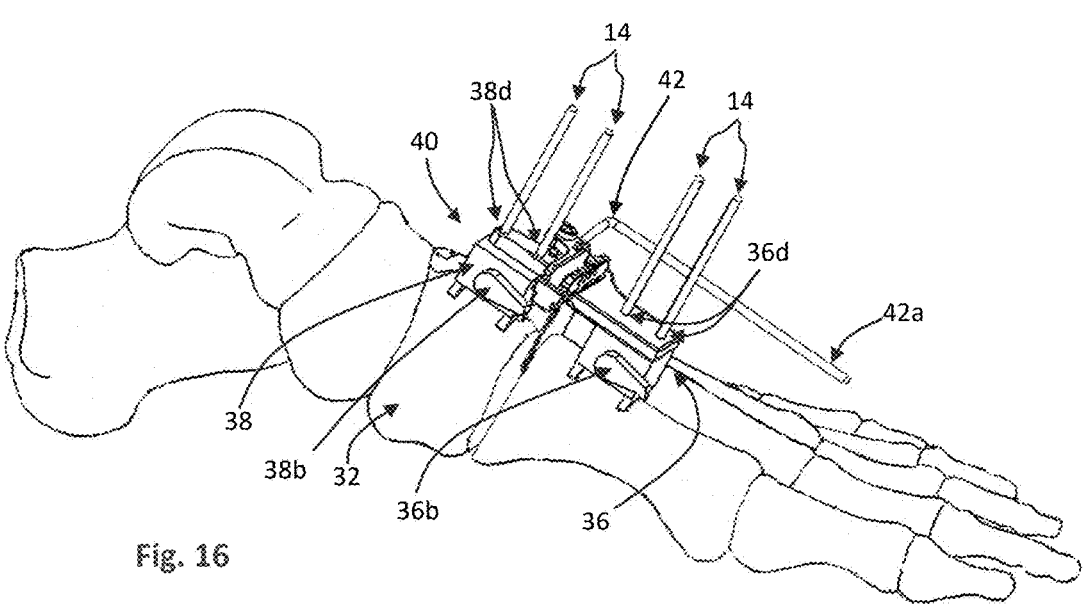
FIG. 16 illustrates a side perspective view of the cuneiform cut guide of FIG. 14, wherein wires are mounted to the medial cuneiform through holes in the cuneiform cut guide.

Once the first metatarsal 30 is placed in the corrected alignment with the second metatarsal 44 and rotationally, wires 14 are inserted through a second locking mechanism or cuneiform scaffold 38 and holes 38d of the second locking mechanism or cuneiform scaffold 38 into the medial cuneiform 32 (FIG. 16).

A saw blade (not shown) is inserted into a cuneiform cut guide slot 46 of the cuneiform cut guide 40 and a distal joint surface of the medial cuneiform 32 is removed or shaved such that the surface is generally oriented perpendicular to the longitudinal axis 16. The cuneiform cut guide slot 46 of the cuneiform cut guide 40 is configured such that the saw blade is directed to cut along a plane perpendicular to the first metatarsal long axis 30a of the first metatarsal 30. With the first metatarsal 30 in the corrected position prior to cutting the cuneiform distal joint surface, the cut planes of the first metatarsal 30 and the medial cuneiform 32 are, therefore, generally parallel to each other following the cutting step of the distal surface of the medial cuneiform 32.

Figure 17:
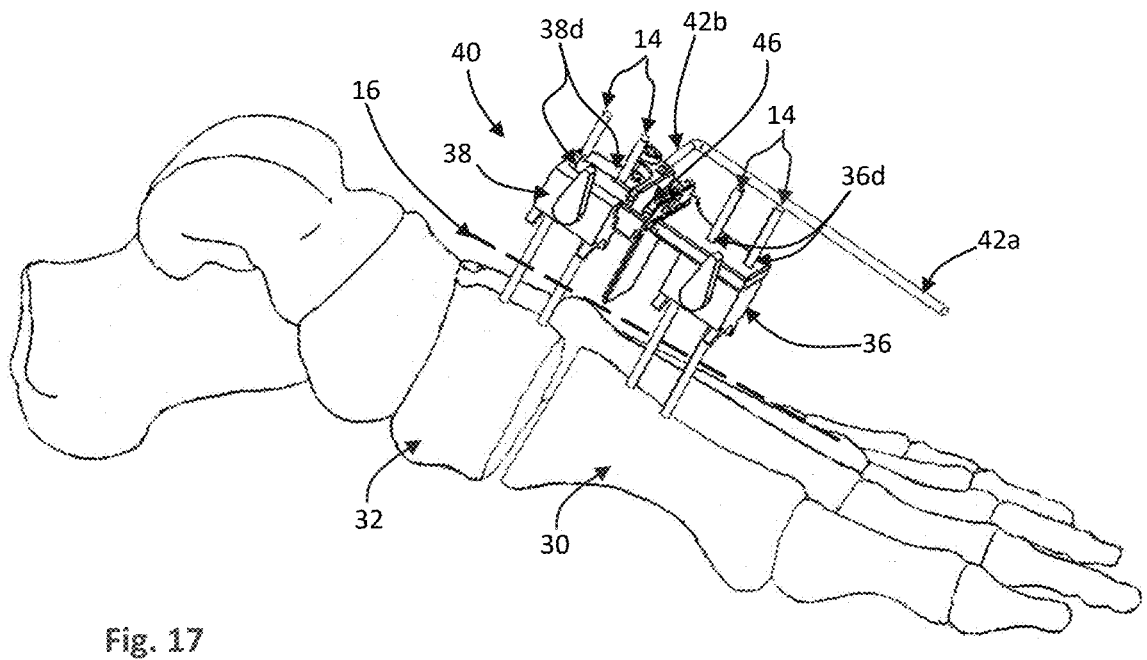
FIG. 17 illustrates a side perspective view of the cuneiform cut guide of FIG. 14, wherein the cuneiform cut guide is moved away from the bones along the wires.

The first and second wire locking mechanisms 36, 38 of the cuneiform cut guide 40 are unlocked by manipulating actuation mechanisms 36b, 38b of the first and second locking mechanisms 36, 38, thereby freeing the cuneiform cut guide 40 to move relative to the wires 40, and the cuneiform cut guide 40 is translated along the wires 14 away from the bones, specifically the first metatarsal 30 and the medial cuneiform 32 in this preferred procedure. The cuneiform cut guide 40 is position such that the wires 14 remain within the holes 36d, 38d of the cuneiform cut guide 40, thereby retaining the corrected alignment of the first metatarsal 30 relative to the medial cuneiform 32 (FIG. 17).

Figure 18:
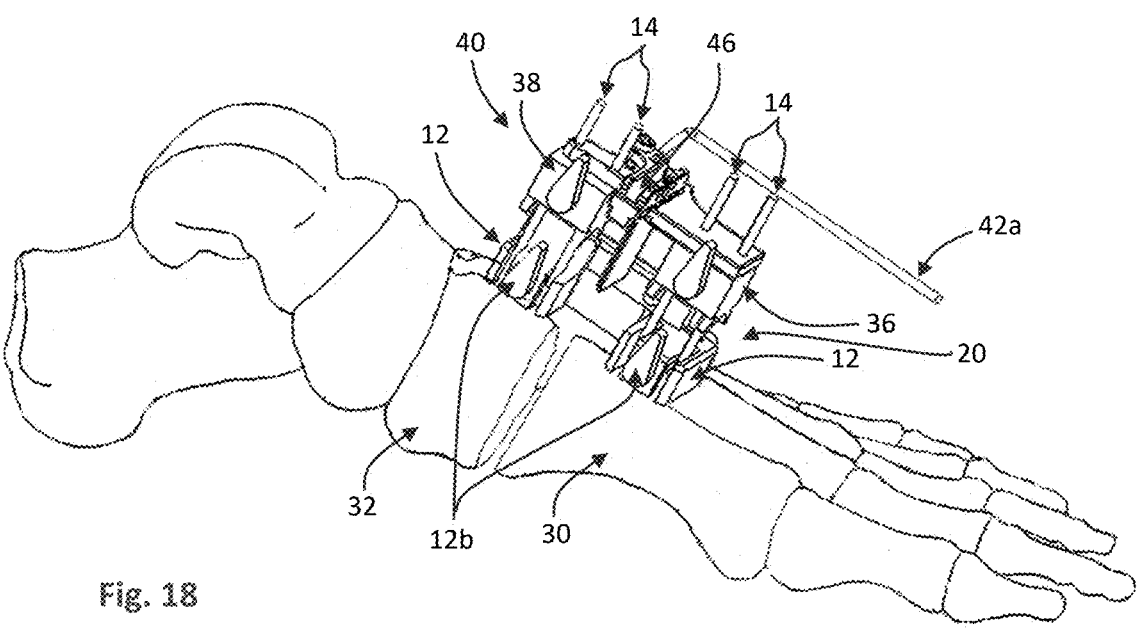
FIG. 18 illustrates a side perspective view of the cuneiform cut guide of FIG. 14 and the compression-distraction tool of FIG. 7, wherein the compression-distraction tool is mounted between the cuneiform cut guide and the bones.

With the cuneiform cut guide 40 positioned above the medial cuneiform 32 and the first metatarsal 30 and the generally parallel prepared surfaces aligned and facing each other, the compression-distraction tool 20 is engaged to the wires 14 between the first metatarsal 30 and the medial cuneiform 32 and the cuneiform cut guide 40 (FIG. 18). With the two locking mechanisms 12 of the compression-distraction tool 20 in an unlocked configuration, the compression-distraction tool 20 is placed onto the bone wires 14 between the cuneiform cut guide 40 and the bones by moving the compression-distraction locking mechanisms in a relatively perpendicular direction to the wires 14 and positioning the wires 14 within the slots 12a of the locking mechanisms 12 (FIG. 18).

Figure 19:
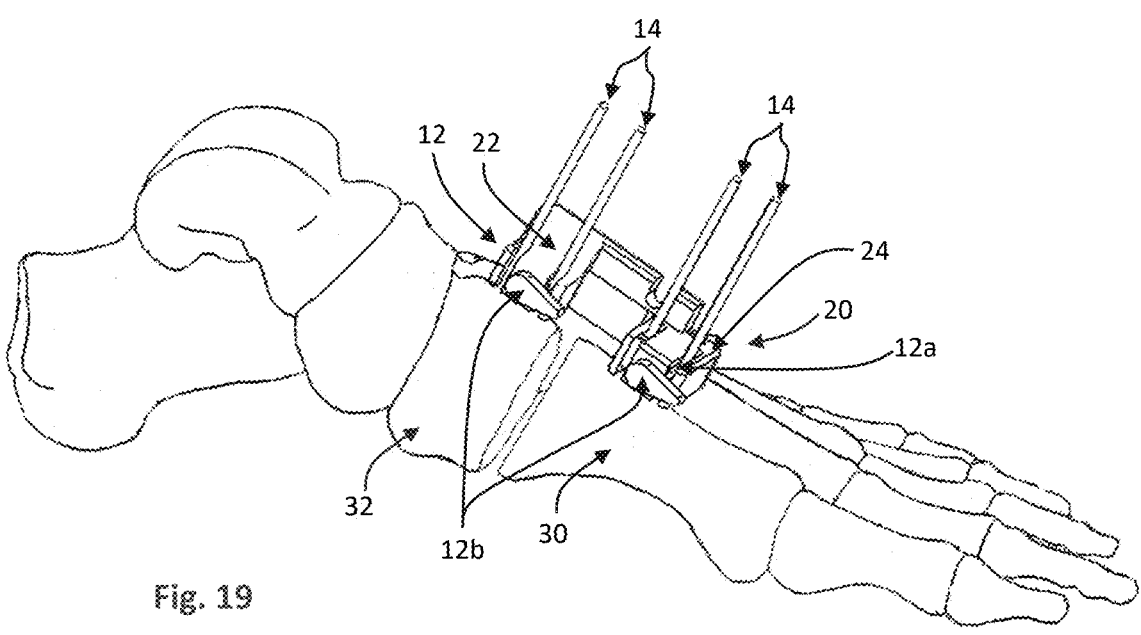
FIG. 19 illustrates a side perspective view of the compression-distraction tool of FIG. 7, wherein the compression-distraction tool is positioned on the first metatarsal and the medial cuneiform.

The actuation mechanisms 12b of the wire locking mechanisms 12 of the compression-distraction tool 20 are then actuated to lock the compression-distraction tool 20 to the wires 14 wherein the locking bumpers 12c engage the wires 14. The cuneiform cut guide 40 is then removed from the wires 14 by sliding the cuneiform cut guide 40 away from the bones and the compression-distraction tool 20 (FIG. 19).

Figure 20:
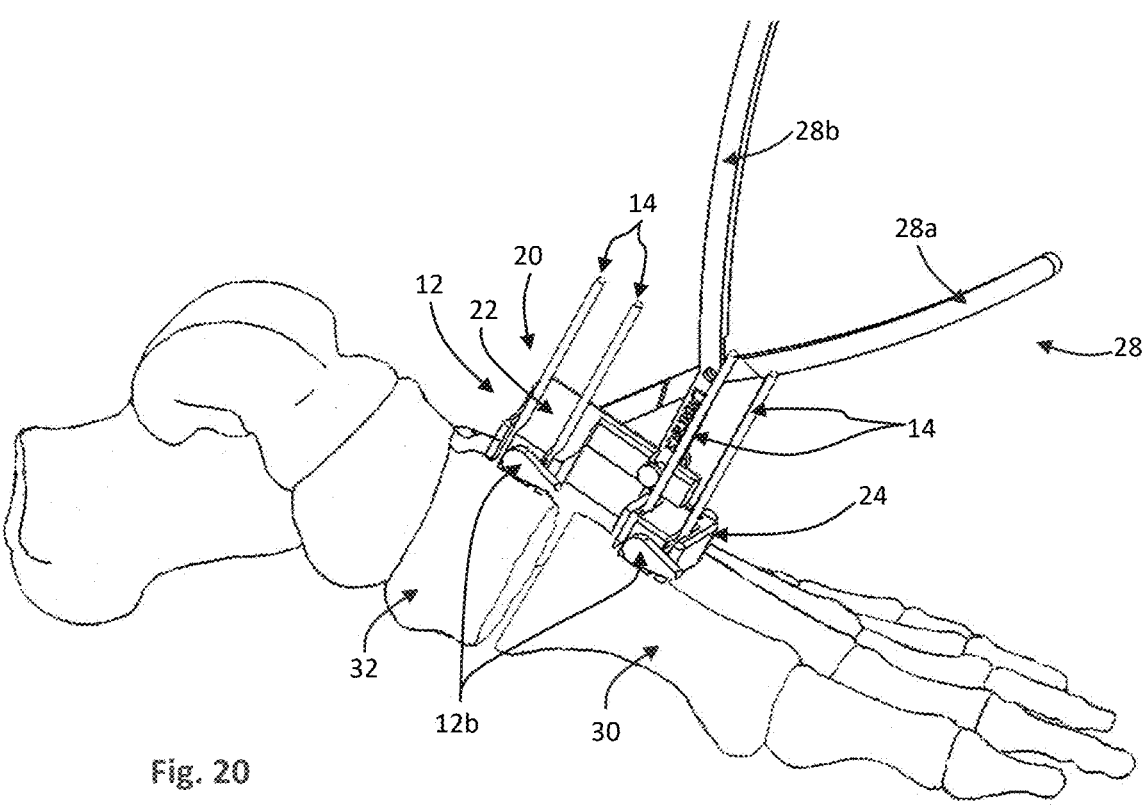
FIG. 20 illustrates a side perspective view of the compression-distraction tool and the compression-distraction handle of FIG. 7 mounted to the patient's foot.

The compression-distraction handle 20 is attached to the first and second sliding members 22, 24 for either compression or distraction as described above. The handle 20 is squeezed to apply the compression or distraction force (FIG. 20). If needed, the temporary handle position lock (not shown) is engaged to retain the compressed or distracted position of the first metatarsal 30 relative to the medial cuneiform 32. When in the compressed positions, the first metatarsal 30 and the medial cuneiform 32 may be fixed in place for fusion using any of the known fixation implants, including screws, bone plates, or other fixation mechanisms.

The wire locking mechanisms 12 of the preferred compression-distraction tool 20 also serves as a means for allowing the surgeon to adjust the bone positions relative to each other before applying the fixation elements to the first metatarsal 30 and the medial cuneiform 32. The wire locking mechanism 12 that is locked to the wires 14 attached to the first metatarsal 30 is unlocked thereby releasing the wires 14 attached to the first metatarsal 30 from the compression-distraction tool 20. The wires 14 may be positioned within the slots 12a of the wire locking mechanism 12 within three degrees of freedom including motion within a plane parallel to the bone cut planes of the first metatarsal 30 and the medial cuneiform 32 and about the first metatarsal long axis 30a of the first metatarsal 30. Therefore, manual manipulation of the first metatarsal 30 by the surgeon after the wires 14 are attached to the first metatarsal 30 and have been unlocked allows the first metatarsal 30 to be translated, relative to the anatomy, in a dorsal-plantar direction, medial-lateral direction, or rotated in the frontal plane (i.e., about the first metatarsal long axis 30a of the first metatarsal 30). After the surgeon manually manipulates the first metatarsal 30 to the desired alignment, the locking mechanism 12 associated with the wires 14 attached to the first metatarsal 30 is locked by manipulating the actuation mechanism 12b to engage the locking bumpers 12c with the wires 14 and compression or distraction may be performed (FIGS. 21-22). The compression-distraction tool 20 in combination with the compression-distraction handle 28, accordingly, is the only instrument or tool in the preferred procedure that facilitates movement of the first metatarsal 30 relative to the medial cuneiform 32 in the compression or distraction direction along the longitudinal axis 16 and the first metatarsal axis 30a and all other rotation, translation or pivoting of the first metatarsal 30 relative to the medial cuneiform 32 during the procedure is performed manually by the surgeon to align the bones in a desired position.

While the example of tarsometatarsal correction surgeon is used to describe the devices and methods above, it should be understood that other surgical applications of the devices, particularly the metatarsal cut guide 29, the compression-distraction tool 20, the compression-distraction handle 20 and the cuneiform cut guide 40, and methods herein are contemplated and applicable.

In the preferred embodiment, the compression-distraction tool 20 includes the slots 12a of the locking mechanism 12 that facilitate attachment of the compression-distraction tool 20 to the wires 14 in a direction generally parallel to the long wire axis 14a and the metatarsal cut guide 29 and the cuneiform cut guide 40 include the holes 12d, 36d, 38d that facilitate attachment of the metatarsal cut guide 29 and the cuneiform cut guide 40 in a direction generally parallel to the long wire axis 14a. The compression-distraction tool 20, the metatarsal cut guide 29 and the cuneiform cut guide 40 are not so limited and may include locking mechanisms 12 with the holes 12d, the slots 12a or other connection mechanisms to secure the instruments to the wires 14. The compression-distraction tool 20 may particularly be designed to include the slots 12a so that the compression-distraction tool 20 may be engaged with the wires 14 laterally while the cuneiform cut guide 40 is spaced from the bones 30, 32 but with the wires 14 still positioned in the holes 12d. This preferred procedure with the compression-distraction tool 20 and the cuneiform cut guide 40 assists in maintaining the positioning of the bones 30, 32 relative to each other while and until the compression-distraction tool 20 is engaged with the wires 14.

Figure 25:
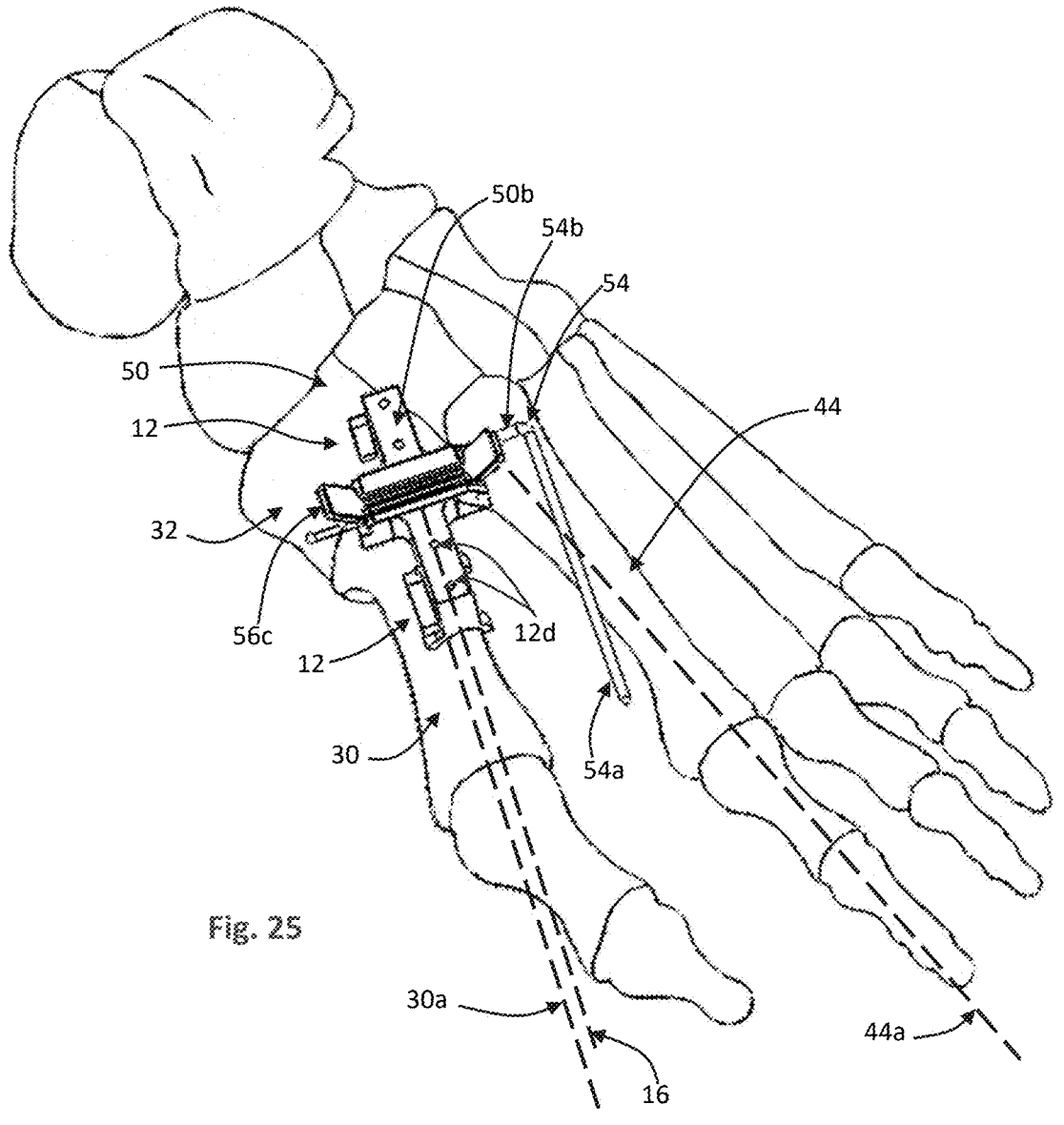
FIG. 25 illustrates a top perspective view of the first ray fixator of FIG. 23 with the cut guide of FIG. 24 mounted thereto, wherein the first ray fixator is positioned on a first metatarsal of a patient's foot and a positioning paddle of the cut guide is positioned in the tarsometatarsal joint of the patient's foot.

Referring to FIGS. 23-25, the preferred system or kit may also include a first ray fixator 50 having a metatarsal side or scaffold 50a, a cuneiform side or scaffold 50b and a cut guide aperture 50c between the metatarsal and cuneiform scaffolds or sides 50a, 50b. The metatarsal side or scaffold 50a and the cuneiform side or scaffold 50b each include a locking mechanism 12 and a pair of holes 12d for selective engagement with the wires 14. The metatarsal side or scaffold 50a also includes arcuate feet 52 on a lower surface that facilitates alignment and engagement with the first metatarsal 30 during use. An alignment arm 54 includes a longitudinal leg 54a that is positioned laterally from the first ray fixator 50 and extends generally parallel to the longitudinal axis 16 when the first ray fixator 50 is mounted to wires 14. The first ray fixator 50 also preferably includes a retention clip 58 having spring-like characteristics. The preferred system or kit also includes a cut guide 56 having a positioning paddle 56a, a cut guide slot 56b oriented generally parallel and laterally spaced from the positioning paddle 56a, ears 56c extending from opposite sides of the cut guide slot 56b and engagement slots 56d. The ears 56c may be utilized by the physician to manipulate the cut guide 56, such as to insert the cut guide 56 into the cut guide aperture 50c and to remove the cut guide 56 from the cut guide aperture 50c. The cut guide slot 56b is preferably laterally positioned and oriented generally parallel to the positioning paddle 56a to align a cut of the bone, as is described in greater detail below. The engagement slot 56d interacts with the retention clip 58 to secure the cut guide 56 in the cut guide aperture 50c of the first ray fixator 50 when the cut guide 56 is positioned in the cut guide aperture 50c. The cut guide 56 includes the joint reference paddle or positioning paddle 56a. There may be two, three or four or more of these cut guides 56 and they can be reversable to be used for both the metatarsal and cuneiform cuts. The cut guides 56 may drop or slide into the cut guide aperture 50c of the first ray fixator 50 and may be reversable relative to the cut guide aperture 50*c*. Alternatively, the cut guides 56 may be configured such that they only fit into the cut guide aperture 50*c* in a single orientation and the kit, in this configuration, includes specific cut guides 56 for the metatarsal cut and separate cut guides 56 for the medial cuneiform cut.

Referring to FIGS. 25-34, in an alternative method for a bunion correction surgery, an incision is made to expose the tarsometatarsal joint of the impacted foot, which is positioned between the first metatarsal 30 and the medial cuneiform 32. The tarsometatarsal joint between the first metatarsal 30 and the medial cuneiform 32 is prepared for correction by removing the tissues attaching the medial cuneiform 32 and the first metatarsal 30 and potentially additional soft tissue. The first ray fixator 50 is positioned over and aligned with the first metatarsal, such that a long axis of the first ray fixator 50 is positioned generally parallel to the first metatarsal long axis 30*a* (FIG. 25). The cut guide 56 is preferably pre-positioned in the cut guide aperture 50*c* with the retention clip 58 engaged with the engagement slot 56*d* such that the positioning paddle 56*a* contacts the proximal head of the first metatarsal 30 and the cut guide slot 56*b* is positioned over the proximal head of the first metatarsal 30. The preferred kit includes multiple cut guides 56 having different lengths for the positioning paddle 56*a* and/or spacing of the cut guide slot 56*b* relative to the positioning paddle 56*a*. The first ray fixator 50 is positioned on the first metatarsal 30 with the first metatarsal 30 in the diseased orientation and the engagement of the engagement slot 56*d* with the retention clip 58 assists in maintaining the cut guide 56 in the cut guide aperture 50*c*. The feet 52 on the metatarsal side or scaffold 50*a* of the first ray fixator 50 assist with aligning the long axis of the first ray fixator 50 with the first metatarsal long axis 30*a* (FIG. 25).

Figure 26:
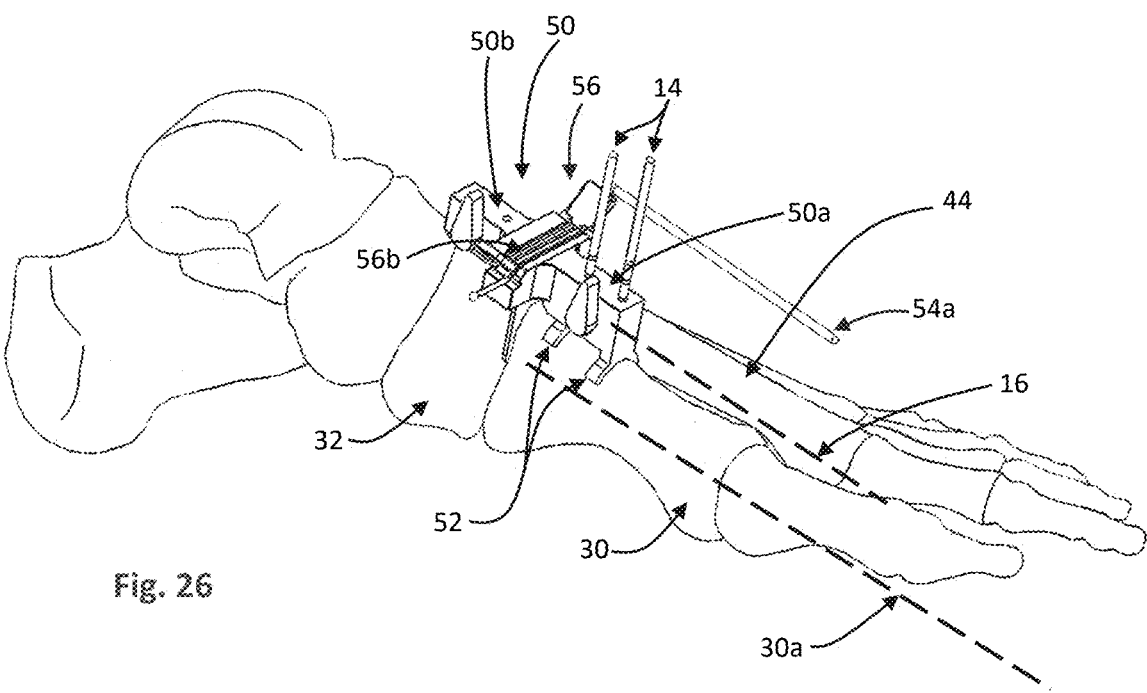
FIG. 26 illustrates a side perspective view of the first ray fixator and cut guide of FIG. 25, wherein wires are mounted to the first metatarsal through holes in a metatarsal side of the first ray fixator.
Figure 27:
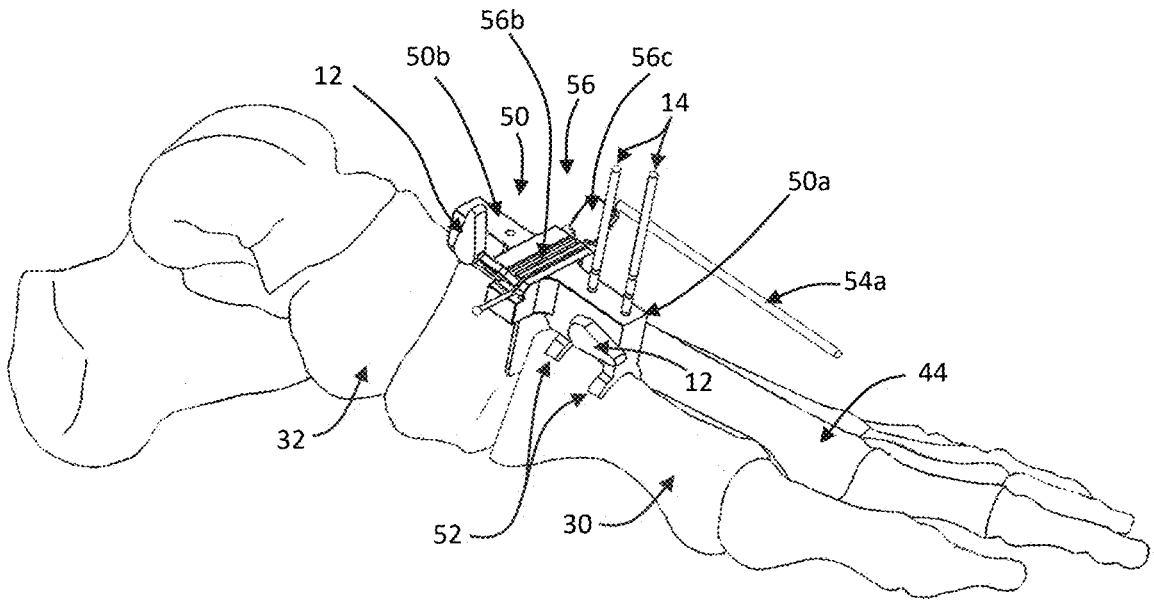
FIG. 27 illustrates a side perspective view of the first ray fixator and cut guide of FIG. 25, wherein a metatarsal side locking mechanism is configured in a locked position.

Wires 14 are then inserted through the holes 12*d* in the metatarsal side or scaffold 50*a* of the first ray fixator 50 to secure the first ray fixator 50 to the first metatarsal. In this position, the longitudinal axis 16 is preferably aligned generally parallel to the first metatarsal long axis 30*a* (FIG. 26). The locking mechanism 12 on the metatarsal side or scaffold 50*a* is then actuated from the open position to the locked position to secure the wires 14 to the first ray fixator 50 and the position of the first metatarsal 30 to the first ray fixator 50 and the cut guide 56. A cutting instrument or saw is then inserted into the cut guide slot 56*b* to cut the proximal joint surface of the first metatarsal 30 (FIG. 27).

Figure 28A:
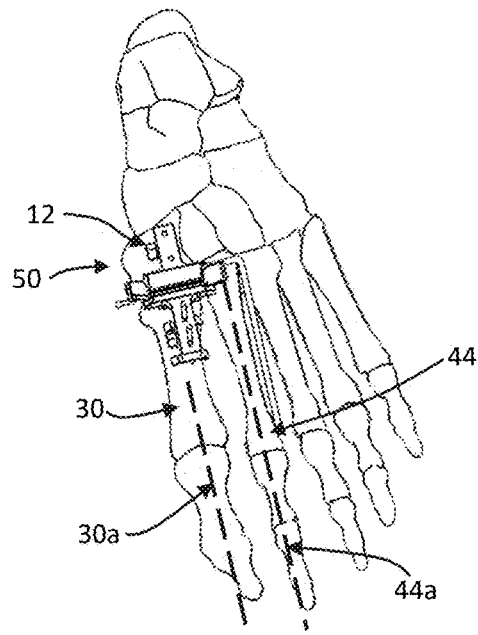
FIG. 28A illustrates a top perspective view of the first ray fixator of FIG. 25, wherein the first metatarsal is moved such that an alignment guide of the first ray fixator is aligned with the patient's second metatarsal and the cut guide of FIG. 24 is rotated one hundred eighty degrees an inserted into a cut guide slot of the first ray fixator or another cut guide is inserted into the cut guide slot of the first ray fixator.
Figure 28B:
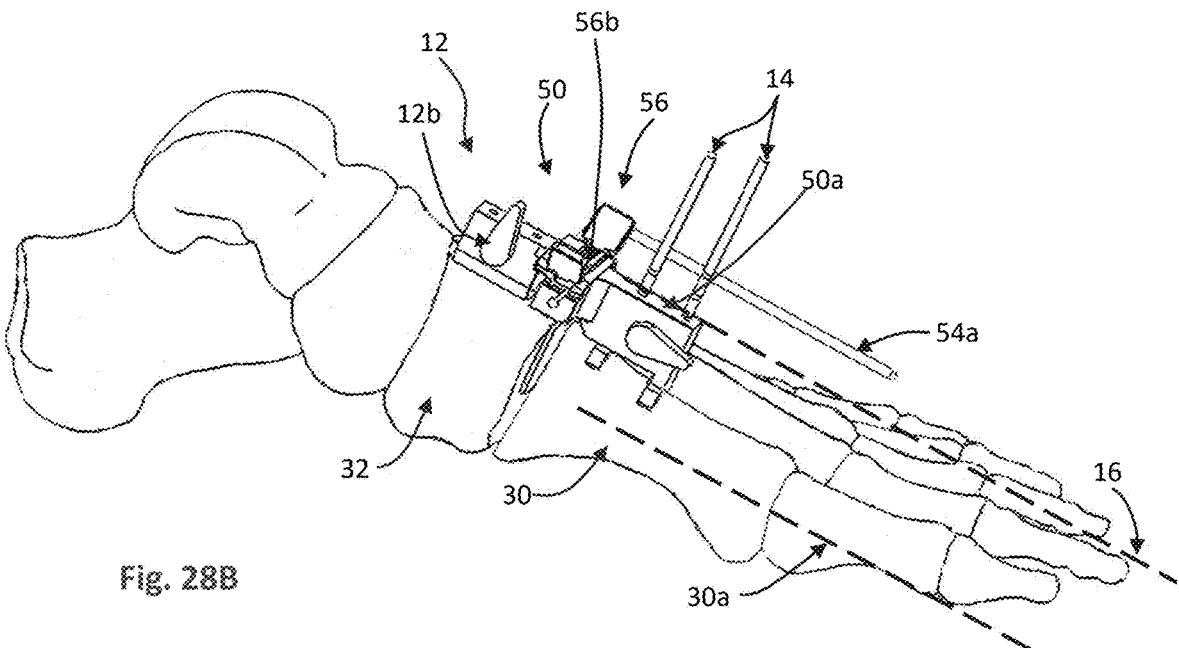
FIG. 28b illustrates side perspective view of the first ray fixator and the cut guide of FIG. 28A.

The cut guide 56 is then removed from the cut guide aperture 50*c*, rotated one hundred eighty degrees (180°) relative to the cut guide aperture 50*c*, and reinserted into the cut guide aperture 50*c* or the first cut guide 56 is replaced by a second cut guide 56 having a different length for the positioning paddle 56*a* or distance between the cut guide slot 56*b* and the positioning paddle 56*a* to facilitate cutting of the distal end of the medial cuneiform 32. The cut guide 56 is removed by releasing the retention clip 58 from the engagement slot 56*d* and when rotates and replaced, the cut guide 56 preferably snap locks into the cut guide aperture 50*c* when the retention clip 58 engages the engagement slot 56*d*. The surgeon then manually repositions the orientation of the first metatarsal 30 relative to the medial cuneiform 32 by pivoting and moving the first metatarsal 30 such that it is aligned with the medial cuneiform 32 and the longitudinal leg 54*a* of the alignment arm 54 is aligned generally parallel to the second metatarsal long axis 44*a* of the second metatarsal 44 to correct the bunion (FIGS. 28A and 28B).

Wires 14 are then inserted into the medial cuneiform 32 through the locking mechanism holes 12*d* in the cuneiform

Figure 29:
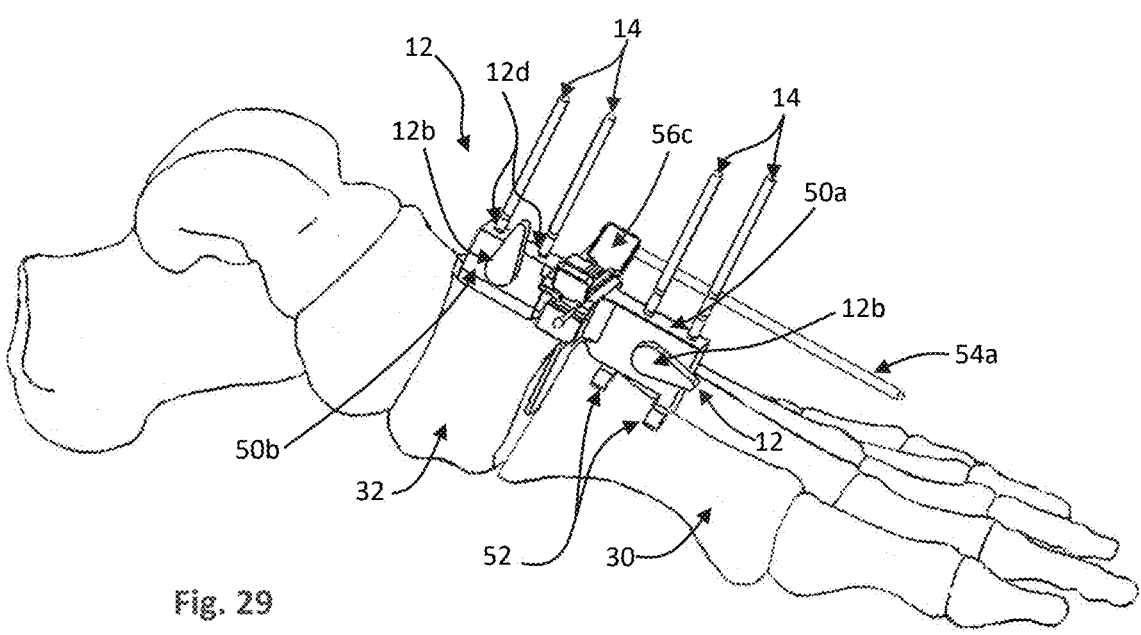
FIG. 29 illustrates a side perspective view of the first ray fixator and the cut guide of FIG. 28A, wherein wires are inserted through holes in a cuneiform side of the first ray fixator and into the patient's cuneiform.
Figure 30:
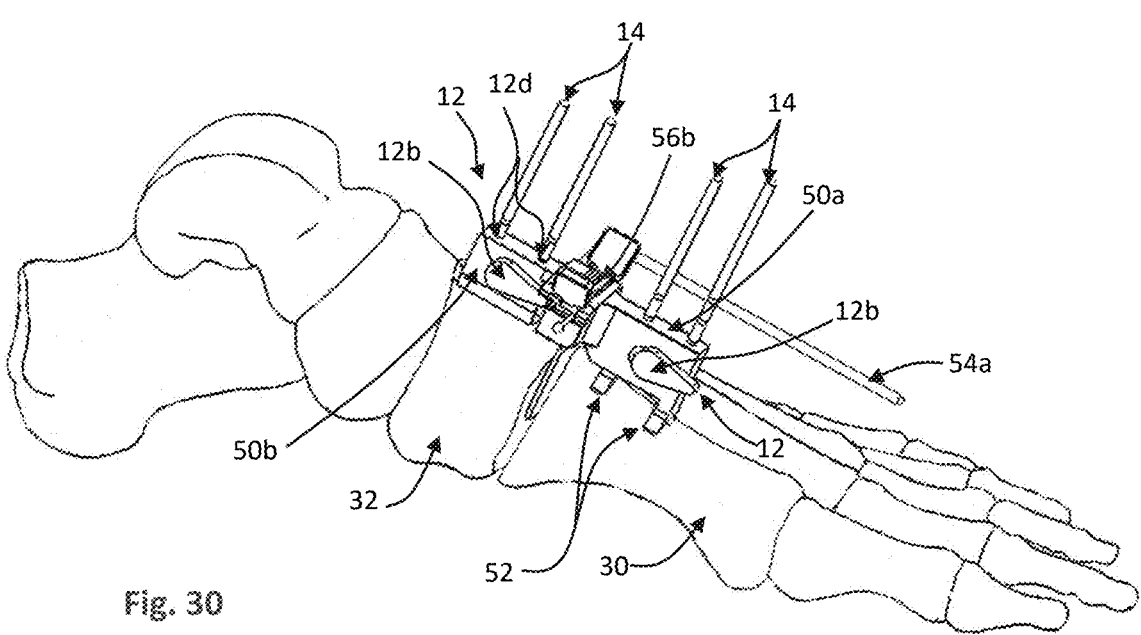
FIG. 30 illustrates a side perspective view of the first ray fixator and the cut guide of FIG. 29, wherein a cuneiform side locking mechanism is configured in a locked position.
Figure 31:
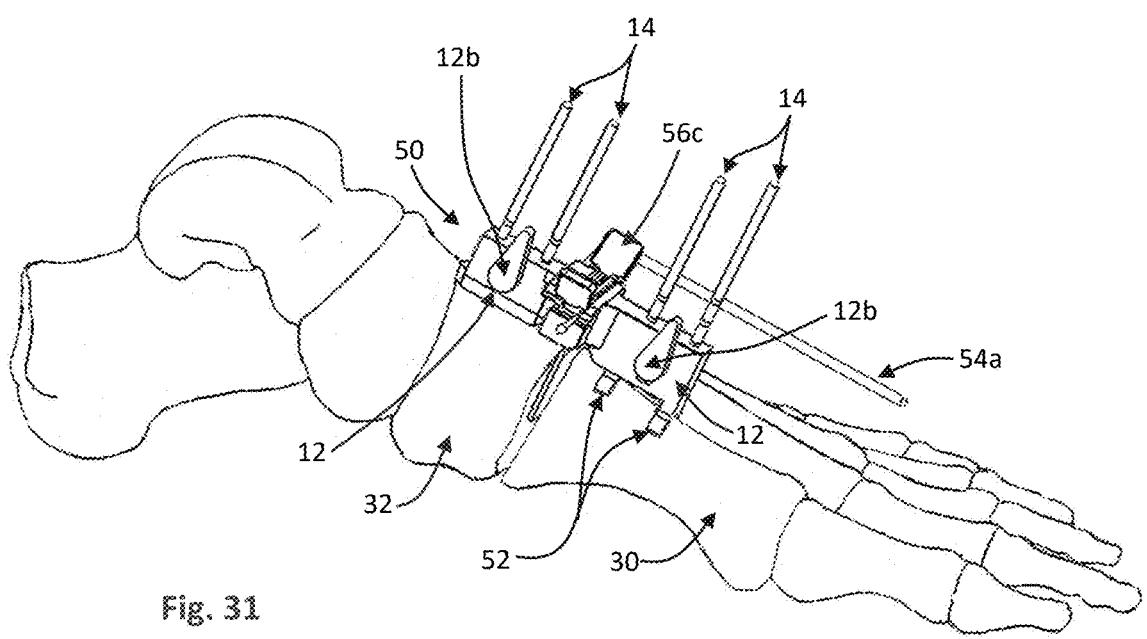
FIG. 31 illustrates a side perspective view of the first ray fixator and the cut guide of FIG. 29, wherein the cuneiform and metatarsal side locking mechanisms are configured in an open position.
Figure 32:
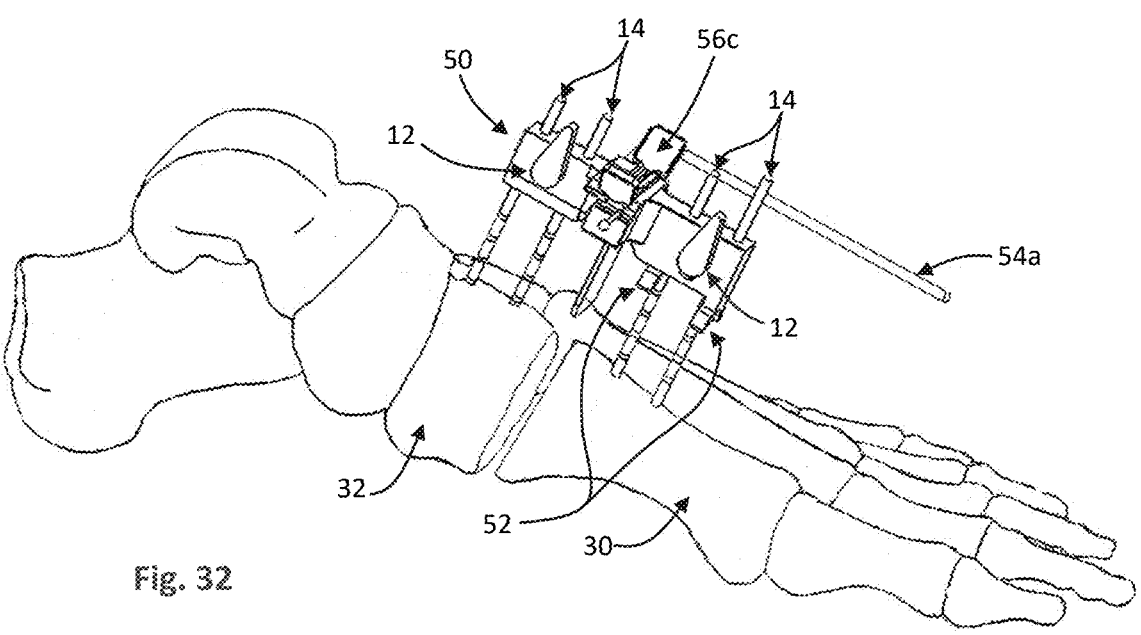
FIG. 32 illustrates a side perspective view of the first ray fixator and the cut guide of FIG. 29, wherein the first ray fixator is moved away from the bones along the wires.
Figure 33:
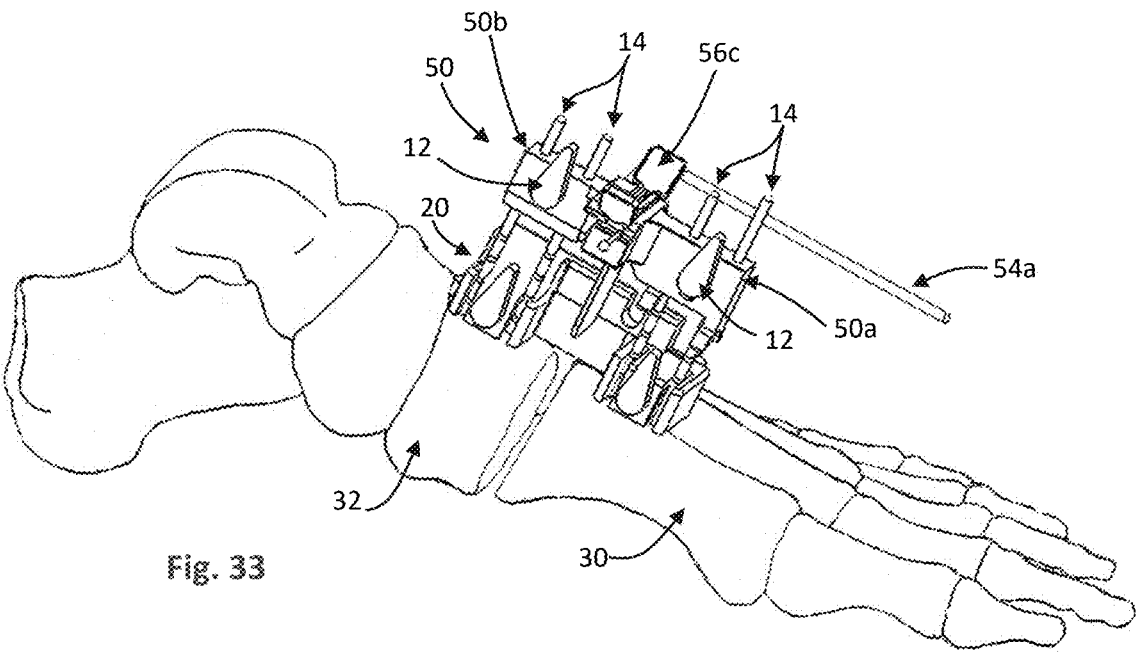
FIG. 33 illustrates a side perspective view of the first ray fixator and the cut guide of FIG. 32 and the compression-distraction tool of FIG. 7, wherein the compression-distraction tool is mounted between the first ray fixator and the bones.
Figure 34:
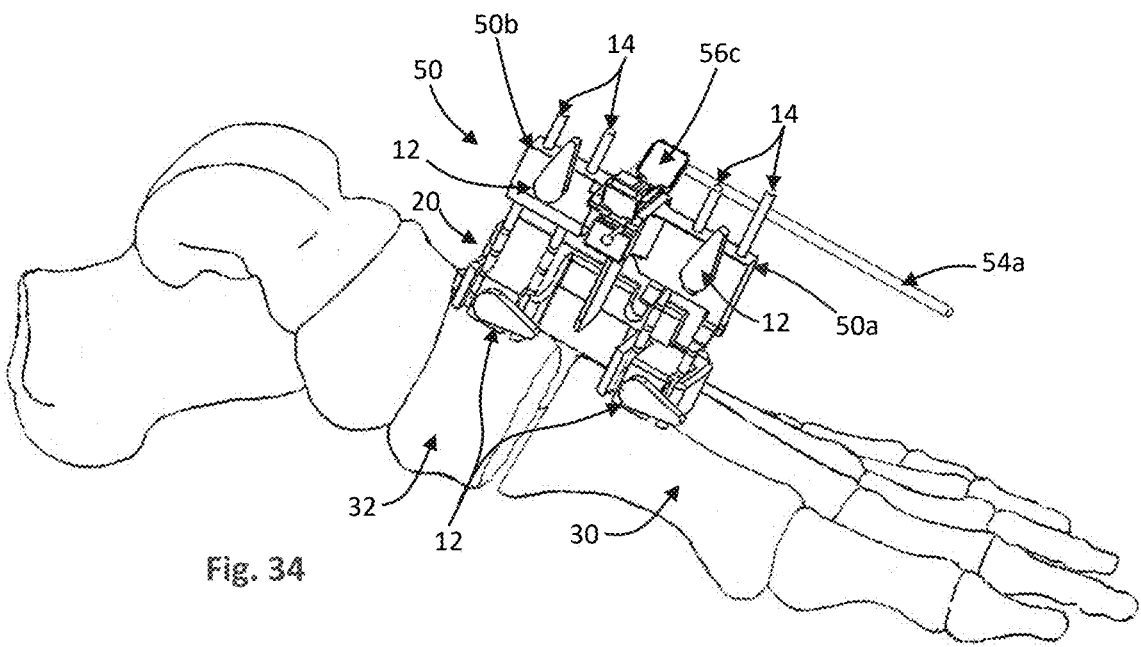
FIG. 34 illustrates a side perspective view of the first ray fixator, the cut guide and the compression-distraction tool of FIG. 33, wherein locking mechanisms of the compression-distraction tool are configured in a locked position.

16 side 50*b* and into the medial cuneiform 32 and the locking mechanisms 12 are actuated to the locked position by pivoting the actuation mechanism 12*b* to fix the positions of the first metatarsal 30, the medial cuneiform 32 and the first ray fixator 50 (FIGS. 29 and 30). With the first metatarsal 30, the medial cuneiform 32 and the first ray fixator 50 fixed relative to each other, the surgeon inserts a cutting blade or saw through the cut guide slot 56*b* to cut the distal surface of the medial cuneiform 32, which cut surface is oriented generally parallel to the opposing cut surface on the proximal end of the first metatarsal 30 (FIG. 30). The locking mechanisms 20 on the metatarsal and cuneiform sides or scaffolds 50*a*, 50*b* of the first ray fixator 50 are actuated with the actuation mechanism from the locked position to the open position to release the locking mechanisms 12 from the wires 12 (FIG. 31). The first ray fixator 50 is then urged or slid upwardly or partially upwardly on the wires 14 such that the first ray fixator 50 is positioned on the wires 14 upwardly a sufficient distance such that the compression-distraction tool 20 may be engaged with the wires 14 between the first ray fixator 50 and the bones. The first ray fixator 50 may be locked in this position by actuating the actuation mechanisms 12*b* to the locked position or may remain unlocked. Maintaining the first ray fixator 50 in this position assists with maintaining the positional alignment of the first metatarsal 30 relative to the medial cuneiform 32 and the prepared opposing surfaces, as well as clearing space for attaching the compression-distraction tool 20 (FIGS. 32 and 33). The compression-distraction tool 20 is then engaged with the wires 14 by urging the compression-distraction tool 20 onto the wires 14 by guiding the wires 14 into the slots 12*a* with the locking mechanisms 12 in the open position (FIG. 33). The locking mechanisms 20 of the compression-distraction tool 20 are then actuated to the locked position to secure the compression-distraction tool 20 to the wires 14, the first metatarsal 30 and the medial cuneiform 32 (FIG. 34). The first ray fixator 50 is removed from the wires 14 and the procedure using the compression-distraction tool 20 proceeds as is described above and shown in FIGS. 19-22 and 35A-36C.

Referring to FIGS. 35A-35C and as is described above, the compression-distraction handle 28 is placed on the compression-distraction tool 20 for distraction in FIGS. 35A-35C. The compression-distraction handle 28 may include a visual indicator, such as the word, "Distract" shown in FIGS. 35A and 35B and facing toward the actuation mechanisms 12*b* to provide a visual indication to the surgeon that the compression-distraction handle 28 and the compression-distraction tool 20 are configured for distraction of the bones, such as the first metatarsal 30 and the medial cuneiform 32. From this configuration, the compression-distraction handle 28 is squeezed to distract the bones.

Figures 36A, 36B:
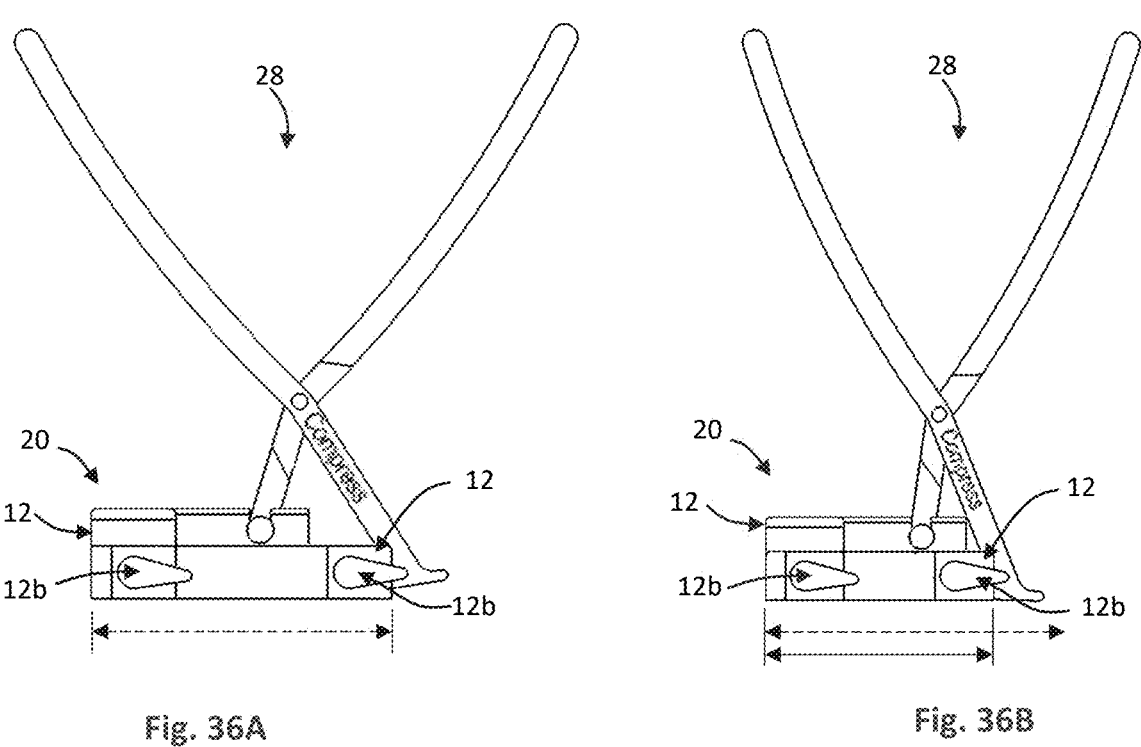
FIG. 36A illustrates a side perspective view of the compression-distraction tool of FIG. 7 and the compression-distraction handle of FIG. 4, wherein the compression-distraction tool and the compression-distraction handle are prepared for compression.
FIG. 36B illustrates a side perspective view of the compression-distraction tool and the compression-distraction handle of FIG. 36A, wherein the compression-distraction handle is actuated to compress the bones.
Figure 36C:
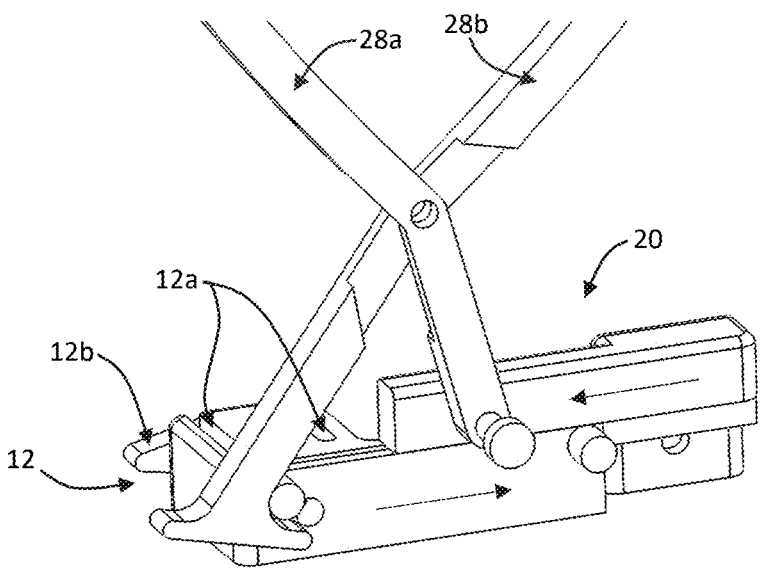
FIG. 36C illustrates a magnified, opposite side perspective view of the compression-distraction tool and the compression distraction handle of FIG. 36A, wherein the compression-distraction handle is actuated to compress the bones.

Referring to FIGS. 36A-36C, in contrast, the compression-distraction handle 28 is pivoted one hundred eighty degrees (180°) relative to the compression-distraction tool 20 and is engaged with the compression-distraction tool 20 to facilitate compression of the joint or the bones, such as the first metatarsal 30 and the medial cuneiform. The compression-distraction handle 28 may include a visual indicator, such as the word, "Compress" shown in FIGS. 36A and 36B and facing toward the actuation mechanisms 12*b* to provide a visual indication to the surgeon that the compression-distraction handle 28 and the compression-distraction tool 20 are configured for compression of the bones, such as the first metatarsal 30 and the medial cuneiform 32. From this configuration, the compression-distraction handle 28 is squeezed to compress the bones or urge the generally parallel prepared surfaces of the first metatarsal 30 and the medial cuneiform 32 toward each other.

Referring to FIGS. 37-58, in a second preferred embodiment, surgical instruments 210 for bunion correction include a compression-distraction tool 220 and a first ray fixator 250. The second preferred embodiment of the surgical instruments 210 is similar to the first preferred embodiment described above and reference numbers are utilized to identify the same or similar features of the second preferred embodiment with a "2" prefix identifying the second preferred embodiment compared to the first preferred embodiment.

The second preferred first ray fixator 250 includes a locking mechanism 212 in a metatarsal side or scaffold 250a of the first ray fixator 250. The locking mechanism 212 is utilized to secure the metatarsal scaffold 250a and the first ray fixator 250 to the bone wires 14 that are mounted to the patient's metatarsal. The locking mechanism 212 includes slots 212a, an actuation mechanism 212b comprised of a screw, locking levers 212e, a wedge 212f, a k-wire guide cap 212g, a scaffold housing 260 with scalloped gripping surfaces 260a and a back cover 262. The preferred actuation mechanism 212b may be actuated by a screwdriver or other tool to tighten or loosen the locking mechanism 212 to engage or release the bone wires 14. The scalloped gripping surfaces 260a of the scaffold housing 260 and complementary scalloped gripping surfaces 264 on the locking levers $212e_1$, $212e_2$ engage an arcuate portion of the wires 14 for secure locking but are not limited for inclusion with the scaffold housing 260 and the locking levers $212e_1$, $212e_2$ and these components may be otherwise designed and configured to securely engage the wires 14.

The second preferred surgical instruments 210 also include a metatarsal alignment wire 266 preferably extending from the metatarsal scaffold housing 260 and having a horizontal leg 266a and a vertical leg 266b. The horizontal leg 266a is preferably connected to the scaffold housing 260 and the vertical leg 266b preferably extends at a ninety-degree (90°) angle from a distal end of the horizontal leg 266a and generally perpendicular to an upper surface of the scaffold housing 260 and the first metatarsal long axis 30a in the mounted configuration. The metatarsal alignment wire 266 is preferably mounted to the scaffold housing 260 at a hub 260b. The metatarsal alignment wire 266 is configured to improve dorsal alignment, as is described in greater detail below.

The second preferred compression-distraction tool 220 includes a gear train 268 to actuate compression and distraction of the metatarsal 30 relative to the cuneiform 32 during operation. The compression-distraction tool 220 is not limited to inclusion of the gear train 268 and may be otherwise designed to have an alternative actuation mechanism to drive the compression and distraction of the bone 30, 32 during use, such as the compression-distraction handle 28.

Referring to FIGS. 28-51, the metatarsal scaffold 250a is releasably lockable to the wires 14, similar to the function of the locking mechanism 12 of the first preferred embodiment, however the locking mechanism 212 has been developed and tested for improved gripping and holding strength for engaging the wires 14. The second preferred locking mechanism 212 includes two locking levers 212e, including first and second locking levers $212e_1$, $212e_2$, that slide along the wedge 212f to urge the locking levers $212e_1$, $212e_2$ toward and away from the wires 14 when they are inserted through the slots 212a1, 212a2 in the metatarsal scaffold 250a. The locking levers $212e_1$, $212e_2$ include the scalloped gripping surfaces 264 that engage a side of the wire 14 and clamp the wire 14 with the complementary scaffold gripping surfaces 260a on the scaffold housing 260. The actuation mechanism or actuation screw 212b is rotated to urge the locking levers $212e_1$, $212e_2$ along the wedge 212f to lock or release the wires 14. Although the locking mechanism 212 of the second preferred embodiment is shown only associated with the metatarsal scaffold 250a, the first ray fixator 250 is not so limited and the cuneiform side or scaffold 250b may also include a locking mechanism 212 for locking and releasing the cuneiform scaffold 250b to associated wires 14.

The locking mechanism 212 is actuated via the actuation mechanism 212b, which is comprised of a dual-thread screw in the second preferred embodiment, to move upward relative to the scaffold housing 260 to apply an outward force against the locking levers 212e, thereby driving the locking levers $212e_1$, $212e_2$ to interact with the associated k-wire 14 that is positioned in the slots 212a1, 212a2 or to move the wedge 212f downward away from the locking levers 212e, allowing them to retract and release the associated k-wire 14. As the actuation mechanism or screw 212b is turned, the threads interacting with the threads in the wedge 212f raise and lower the wedge 212f, as shown in FIGS. 39-45. The second preferred locking mechanism 212 also utilizes roughened or grooved surfaces on the k-wires 14 that interact with the scalloped gripping surfaces 260a, 264 on the scaffold housing 260 and the locking levers $212e_1$, $212e_2$ to further increase the locking strength of the construct.

The scalloped gripping surfaces 260a, 264 on the scaffold housing 260 and the locking levers $212e_1$, $212e_2$ have been added to further strengthen the fixation of the wires 14 to the locking mechanism 212 and to counteract rotational forces on the k-wires 14. The scalloped gripping surfaces 264 on the locking levers $212e_1$, $212e_2$ align with the scalloped gripping surfaces 264 on the scaffold housing 260 of the metatarsal scaffold 250a such that as the k-wires 14 are rotated about the first metatarsal long axis 30, the axis of the scalloped gripping surfaces 260a, 264 are aligned with the new rotated axis of the k-wire 14. FIGS. 46-49 show how the angle of the scalloped gripping surfaces 260a, 264 changes to accommodate a rotated k-wire 14.

Figures 37, 38:
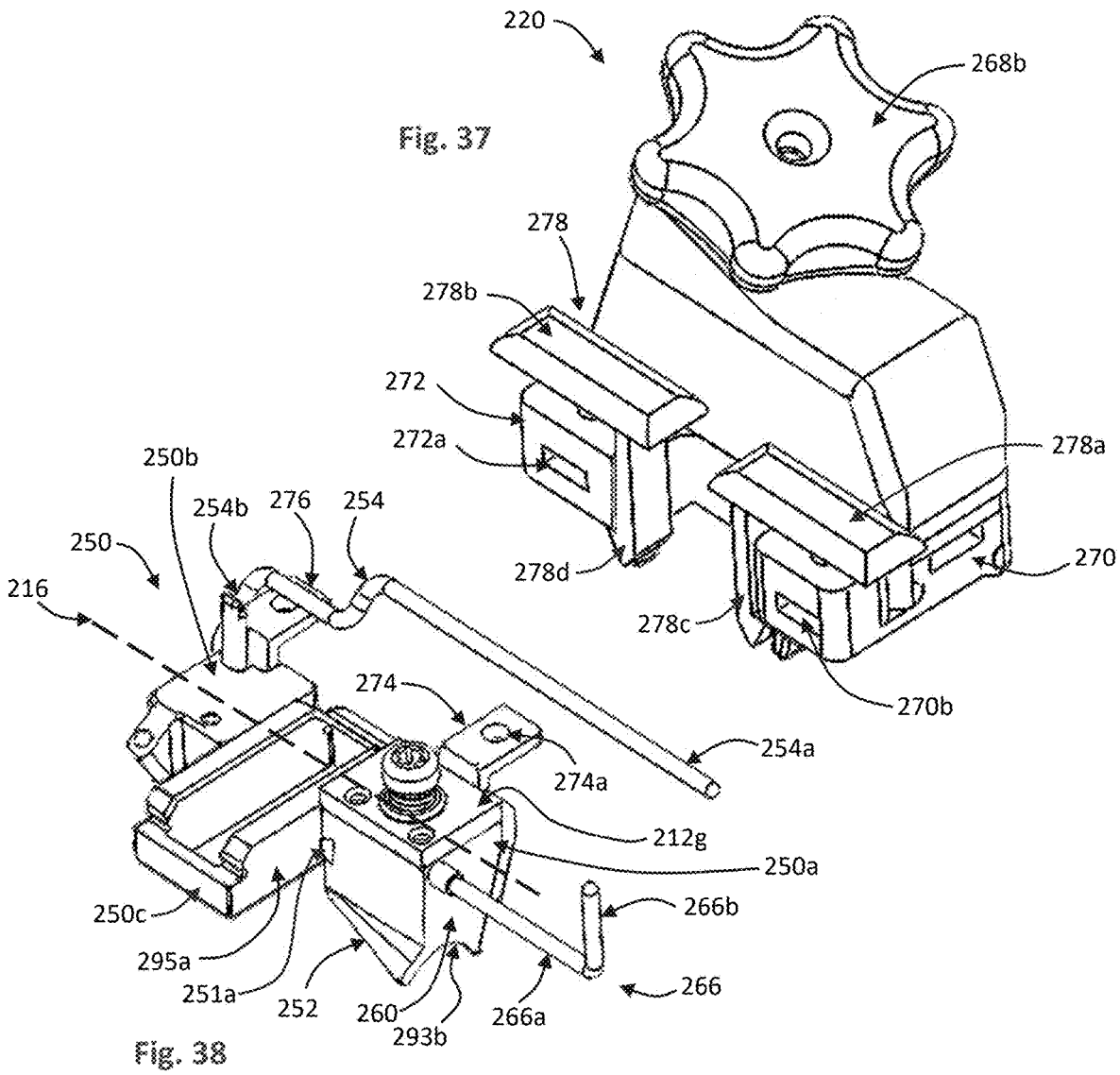
FIG. 37 illustrates a side perspective view of a compression-distraction tool of surgical instruments in accordance with a second preferred embodiment of the present invention for bunion correction.
FIG. 38 illustrates a side perspective view of a first ray fixator of the surgical instruments of the second preferred embodiment of the present invention for bunion correction.
Figure 39:
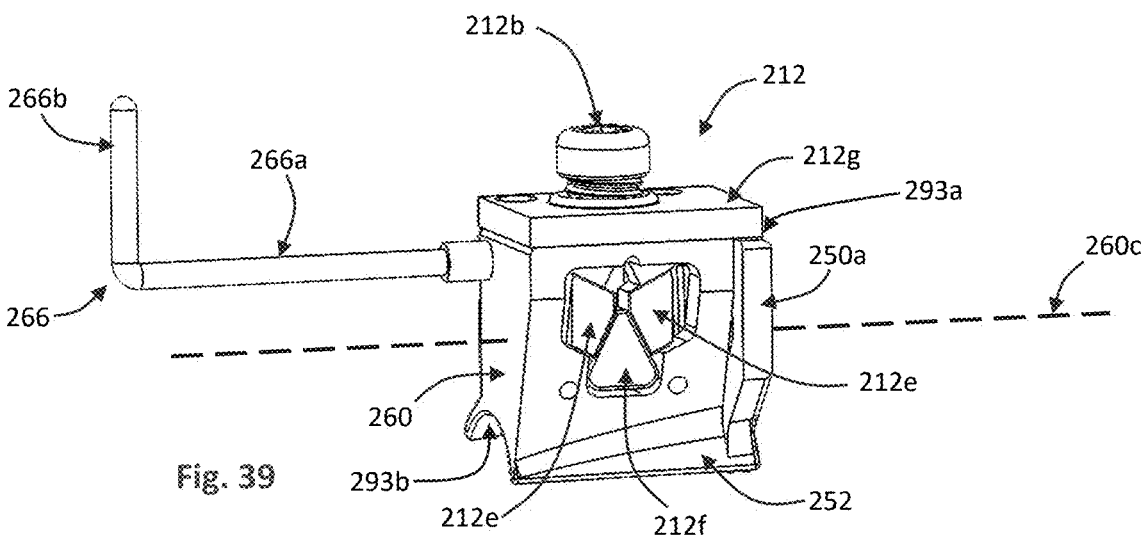
FIG. 39 illustrates a rear perspective view of a metatarsal scaffold of the first ray fixator of FIG. 38, wherein a back cover is removed to expose an internal locking mechanism.
Figure 40:
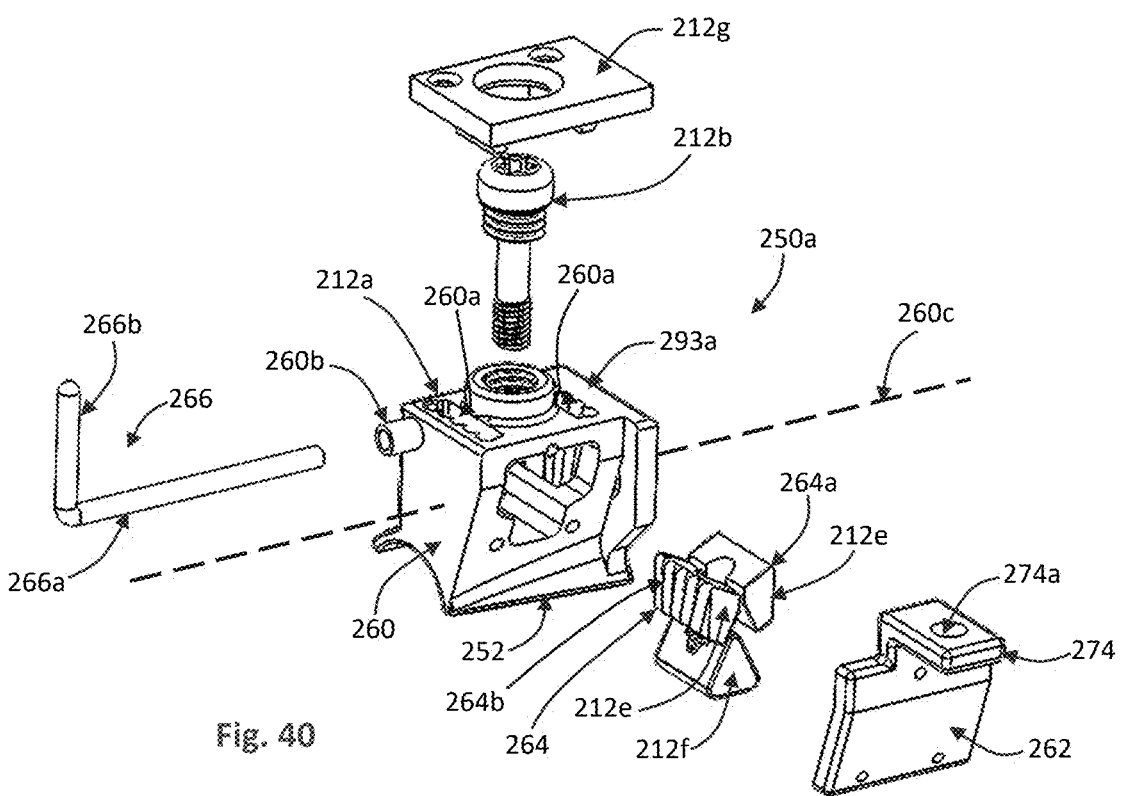
FIG. 40 illustrates an exploded view of the metatarsal scaffold of FIG. 39.
Figures 44, 45, 46, 47:
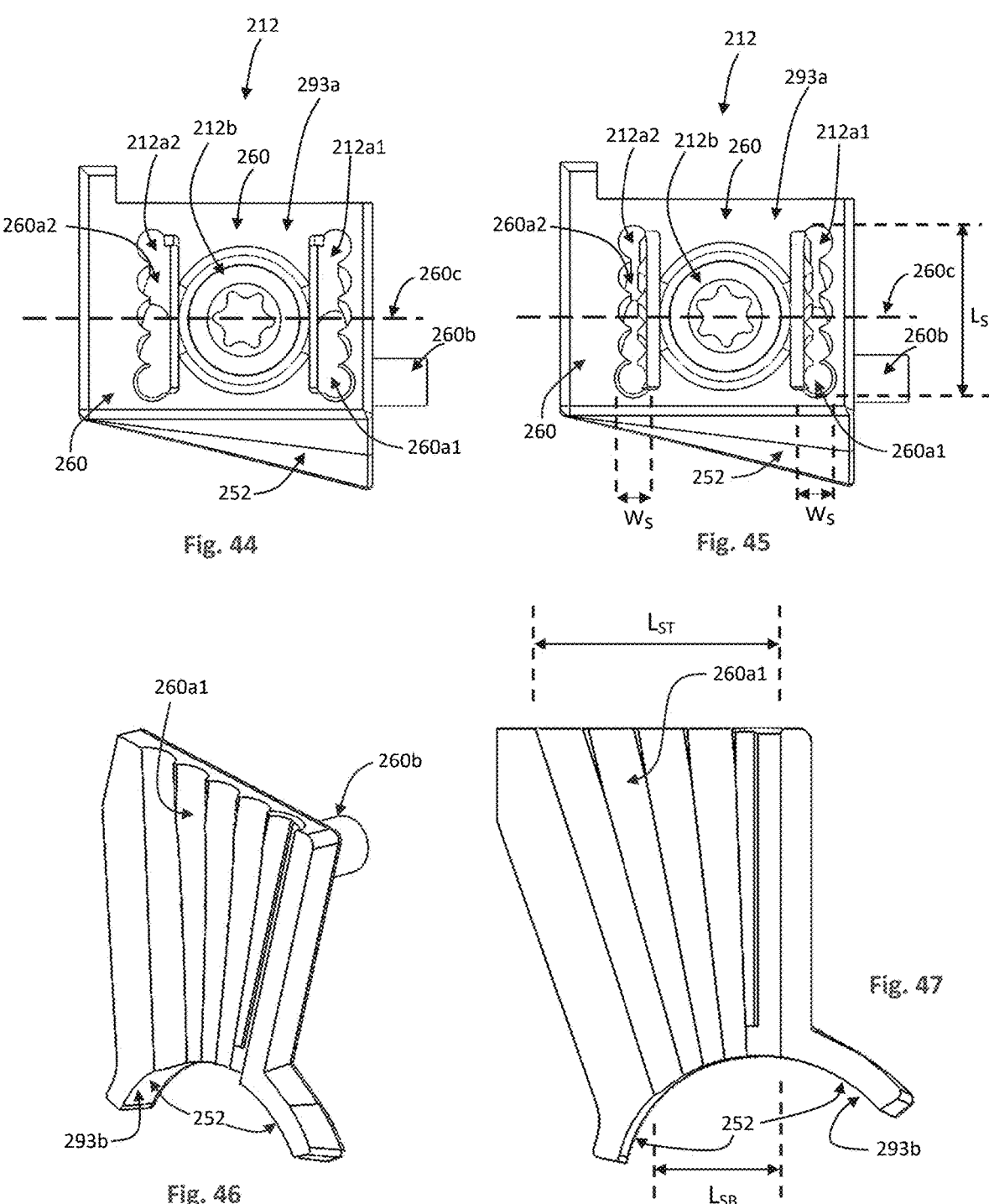
FIG. 44 illustrates a top plan view of the metatarsal scaffold of FIG. 39, wherein the internal locking mechanism is in the unlocked position.
FIG. 45 illustrates a top plan view of the metatarsal scaffold of FIG. 39, wherein the internal locking mechanism is in the locked position.
FIG. 46 illustrates a side perspective view of a scalloped gripping surface of the locking mechanism of the metatarsal scaffold of FIG. 39.
FIG. 47 illustrates a side elevational view of the scalloped gripping surface of FIG. 46.
Figure 51:
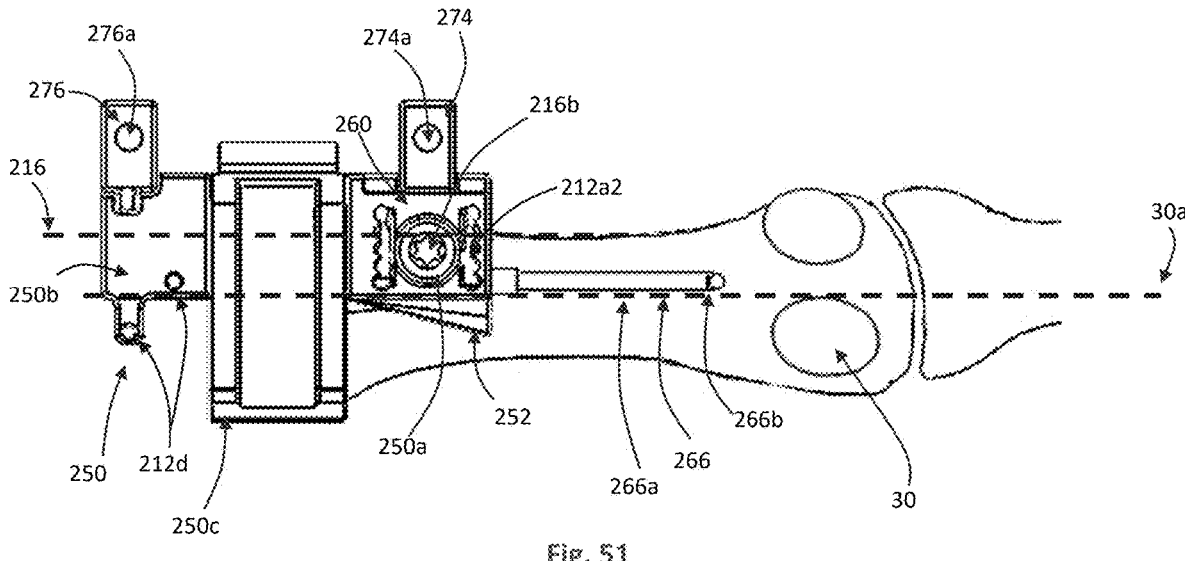
FIG. 51 illustrates a top plan view of the first ray fixator of FIG. 38 positioned on a first metatarsal and the alignment wire of FIG. 50 showing a perfect circle to confirm dorsal view alignment.

Referring to FIGS. 38, 50 and 51, aligning the first ray fixator 250 onto the dorsal surface of the first metatarsal 30 is a preferred step in the use of the second preferred surgical instruments 210 for correcting a bunion. The longitudinal axis 216 of the first ray fixator 250 should be closely aligned with the first metatarsal long axis 30a of the first metatarsal 30 in the mounted configuration and an axis perpendicular to the first metatarsal long axis 30a should be perpendicular to the dorsal surface of the first metatarsal 30. Such positioning aligns the orthogonal coordinate frame of the first ray fixator 250 with the anatomic coordinate frame of the first metatarsal 30. To improve the ability to align the first ray fixator 250 to the metatarsal 30, the ninety-degree (90°) bend is included in the metatarsal alignment wire 266 that is mounted to the metatarsal scaffold 250a.

The horizontal leg 266a of the metatarsal alignment wire 266 is used to align the first ray fixator 250 to the first metatarsal long axis 30a of the first metatarsal 30 from both a dorsal view and a medial view. However, this visual alignment does not provide sufficient visualization of alignment on the dorsal surface. By including the ninety-degree (90°) bend in the metatarsal alignment wire 266, the surgeon or other medical professional can make use of the concept of a "perfect circle" view. When x-ray imaging the 1st metatarsal from a dorsal perspective (FIG. 51), visualization of the sesamoid bones provides confirmation of dorsal view alignment. By placing the first ray fixator 250, utilizing this dorsal viewpoint, such that the vertical leg 266*b* of the metatarsal alignment wire 266 becomes a "perfect circle", as shown, dorsal placement of the first ray fixator 250 can be confirmed. Alternatively, and in similar fashion, the vertical leg 266*b* of the metatarsal alignment wire 266 can be aligned with the long axis 30*a* of the great toe when the toe is placed in extension.

Figure 52:
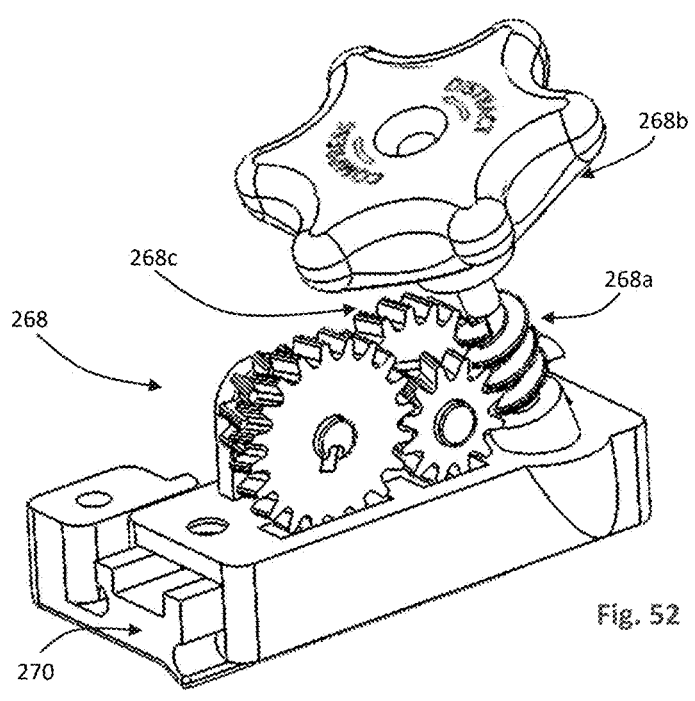
FIG. 52 illustrates a side perspective view of a gear-train of the compression-distraction tool of FIG. 37.
Figure 53:
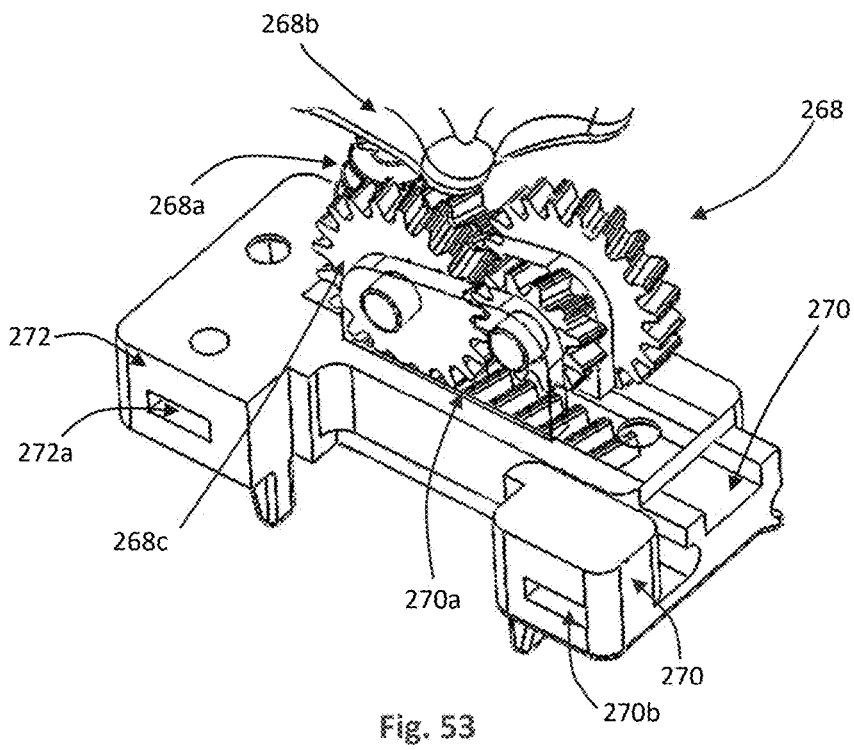
FIG. 53 illustrates a magnified top perspective view of the gear-train of FIG. 52.
Figure 54:
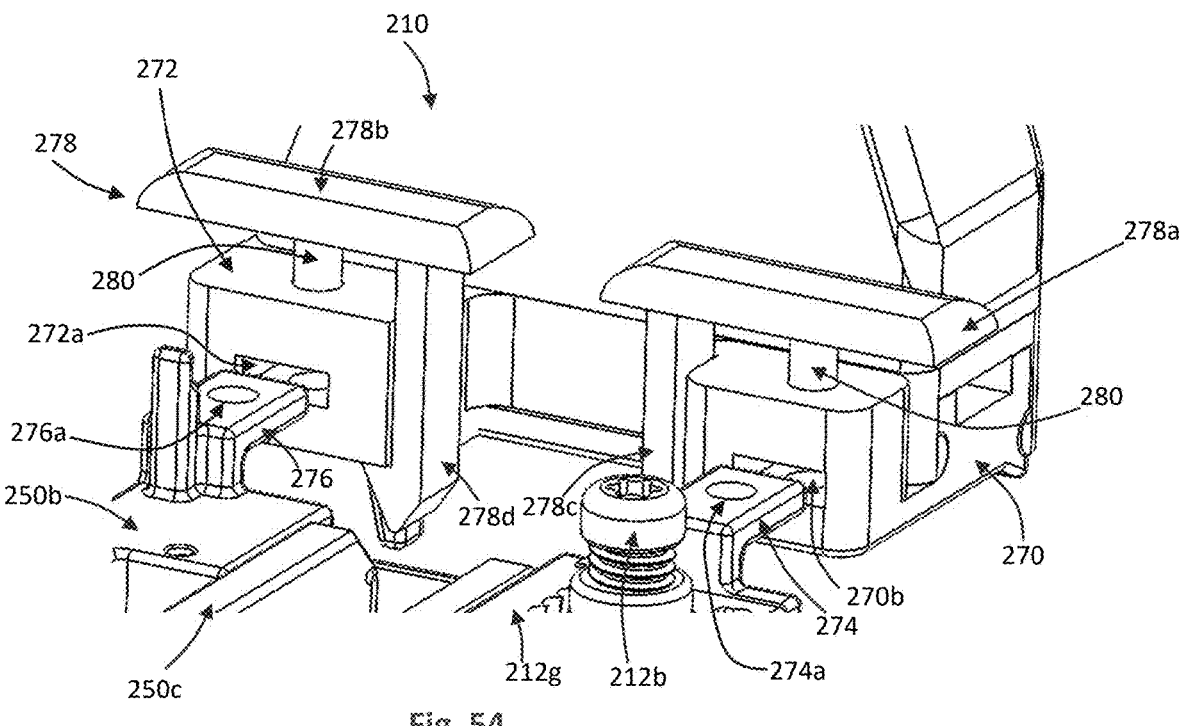
FIG. 54 illustrates a magnified side perspective view of compression-distraction tool of FIG. 37 and the first ray fixator of FIG. 38, wherein tabs of the first ray fixator are being inserted into slots in the compression-distraction tool.

Referring to FIGS. 52 and 53, the compression-distraction tool 220 of the second preferred embodiment includes the gear train 268 to drive compression and distraction of the tarsometatarsal joint or compression and distraction of the first metatarsal 30 relative to the medial cuneiform 32. The gear train 268 includes a worm or worm gear 268*a* attached to a driving knob 268*b*. The driving knob 268*b* is not limiting and the compression-distraction tool 220 may include an alternative actuation mechanism to drive the compression and distraction of the compression-distraction tool 220. The worm gear 268*a* provides a mechanical one-way force constraint so that torque input from the driving knob 268*b* translates to a sliding member 270, but forces acting on the sliding member 270 generally do not translate backward through the gear-train 268. The driving knob 268*b* may be pivoted to compress or distract the first metatarsal 30 relative to the cuneiform 32 in the working configuration.

Additionally, the rotational torque of the gear train 268 is translated to a linear displacement of the sliding member 270 through a rack and pinion configuration. The sliding member 270 is driven by a pinion gear 268*c* in either a compression or distraction direction via interaction with a rack 270*a* of the sliding member 270. The driving knob 268*b* preferably includes a visual indicator thereon to prompt the surgeon regarding whether the direction of rotation of the driving knob 268*b* will result in compression of the joint via a "COMPRESS" indicator with a directional arrow or a distraction of the joint via a "DISTRACT" indicator with an opposite direction arrow. The sliding member 270 is preferably connected to the metatarsal scaffold 250*a* and a base member 272 of the compression-distraction tool 220 is preferably connected to the cuneiform scaffold 250*b* in the mounted configuration, as is described in greater detail below. The gear train 268 is supported by the base member 272 such that the sliding member 270 moves relative to the base member 272 when the driving knob 268*b* is actuated by the surgeon.

Referring to FIGS. 37, 38, 54 and 58, the compression-distraction tool 220 is removably connectable to the metatarsal scaffold 250*a* and the cuneiform scaffold 250*b* after the joint faces of the metatarsal 30 and the cuneiform 32 are prepared and the first ray fixator 250 is secured to the metatarsal 30 and the cuneiform 32 across the joint. A metatarsal tab 274 extends from the metatarsal scaffold 250*a* and a cuneiform tab 276 extends from the cuneiform scaffold 250*b* toward the longitudinal leg 254*a* of the alignment arm 254. The metatarsal and cuneiform tabs 274, 276 are removably insertable into a sliding member slot 270*b* in the sliding member 270 and a base member slot 272*a* in the base member 272, respectively, when the first ray fixator 250 is secured across the joint between the first metatarsal 30 and the medial cuneiform 32 by the wires 14 to secure the compression-distraction tool 220 to the first ray fixator 250.

The compression-distraction tool 220 is secured to the first ray fixator 250 by an attachment mechanism 278 including first and second sliding members 278*a*, 278*b*. The first sliding member 278*a* is connected to and slidable generally perpendicular to the translation direction of the sliding member 270 and the second sliding member 278*b* is connected to the base member 272 and slidable generally perpendicular to the translation direction of the sliding member 270. Each of the first and second sliding members 278*a*, 278*b* includes an engagement pin 280. To engage the compression-distraction tool 220 to the metatarsal scaffold 250*a* and the cuneiform scaffold 250*b*, the metatarsal tab 274 is aligned with the sliding member slot 270*b* and the cuneiform tab 276 is aligned with the base member slot 272*a*. the attachment mechanism 278 is actuated to move the first and second sliding members 278*a*, 278*b* upwardly away from the base member 272 and the sliding member 270 such that the engagement pins 280 move upwardly to provide clearance in the sliding member and base member slots 270*b*, 272*a*. The metatarsal and cuneiform tabs 274, 276 are urged into the sliding member and base member slots 270*b*, 272*a* until holes 274*a*, 276*a* of the metatarsal tab 274 and the cuneiform tab 276, respectively, are aligned with the engagement pins 280. The attachment mechanism 278 is biased in an engaged position and is released such that the pins 280 slide into the holes 274*a*, 276*a* to secure the metatarsal and cuneiform scaffolds 250*a*, 250*b* to the compression-distraction tool 220. To maintain the fixation and orientation of the first metatarsal 30 to the medial cuneiform 32, the first ray fixator 250 is a rigid construct when the cut guide aperture 250*c* is secured to the metatarsal and cuneiform scaffolds 250*a*, 250*b*. However, when the compressor-distractor tool 220 is attached and secured to the metatarsal and cuneiform scaffolds 250*a*, 250*b*, the cut guide aperture 250*c* may be removed such that the metatarsal scaffold 250*a* is translatable relative to the cuneiform scaffold 250*b*. By securing the compressor-distractor tool 220 to the first ray fixator 250 before the cut guide aperture 250*c* is disengaged, the corrected alignment of the first metatarsal 30 to the medial cuneiform 32 is not lost. Therefore, it is preferred that the cut guide aperture 250*c* is not released from the metatarsal and cuneiform scaffolds 250*a*, 250*b* until the compressor-distractor tool 220 is locked onto the metatarsal and cuneiform scaffolds 250*a*, 250*b*, as is described above. To accomplish this, the attachment mechanism 278 is added to the compressor-distractor tool 220 and the cut guide aperture 250*c* is configured for removable mounting to the metatarsal and cuneiform scaffolds 250*a*, 250*b*.

In operation, the metatarsal and cuneiform scaffold tabs 274, 276 are urged into the sliding member and base member slots 270*b*, 272*a*. The tabs 274, 276 are connected to the compressor-distractor tool 220 when the engagement pins 280 are positioned in the metatarsal and cuneiform holes 274*a*, 276*a*.

Referring to FIGS. 38, 51 and 55-58, the compressor-distractor tool 220 and the first ray fixator 250 are designed and configured such that the cut guide aperture 250*c* may only be removed from the first ray fixator 250 when the compressor-distractor tool 220 is engaged or connected to the metatarsal and cuneiform scaffolds 250*a*, 250*b* or, preferably, the first ray fixator 250 when mounted across the joint. The cut guide aperture 250*c* includes locking buttons 282*a*, 282*b* that release the cut guide aperture 250*c* only when the compressor-distractor tool 220 is locked to the first ray fixator 250. The locking buttons 282*a*, 282*b* positioned on the lateral aspect of the cut guide aperture 250*c* and are biased to and outwardly extending position, preferably by spring plungers. The locking buttons 282*a*, 282*b* are preferably include small cylindrical ends that extend outward due to the internal spring force and are retractable into the cut guide aperture 250*c* by applying an inward force against the locking buttons 282*a*, 282*b* that overcomes the spring force. The cylindrical ends of the locking buttons 282*a*, 282*b* can be forced inward against the spring force, but when released extend back outward. When the cut guide aperture 250*c* is attached to the metatarsal and cuneiform scaffolds 250*a*, 250*b*, the cylindrical ends of the locking buttons 282*a*, 282*b* extend out on the lateral side of the metatarsal and cuneiform scaffolds 250*a*, 250*b*, thereby locking the cut guide aperture 250*c* to the metatarsal and cuneiform scaffolds 250*a*, 250*b* by preventing sliding of the cut guide aperture 250*c* away from the metatarsal and cuneiform scaffolds 250*a*, 250*b*.

Figures 57A, 58:
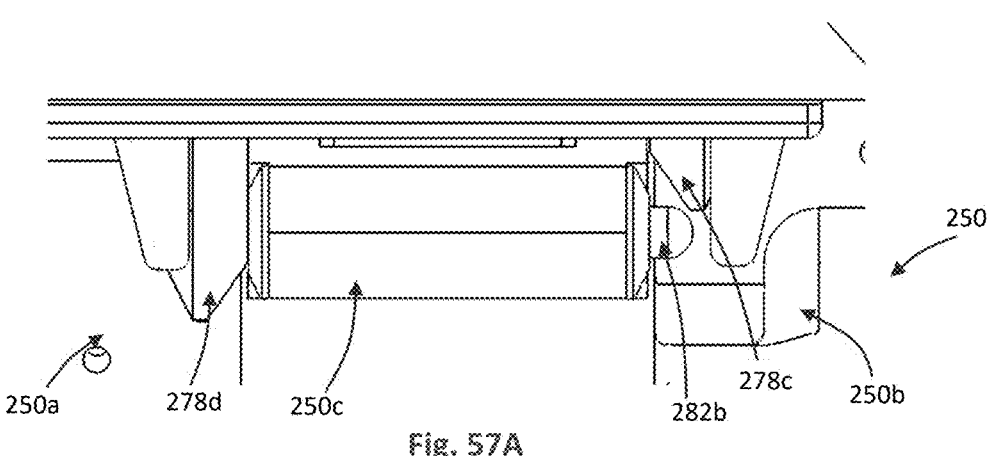
FIG. 57A illustrates a side elevational view of a portion of the compressor-distractor of FIG. 57, taken from within rectangle 57A of FIG. 57.
FIG. 58 illustrates a side perspective view of the compressor-distractor of FIG. 37 mounted to the metatarsal scaffold and a cuneiform scaffold of the first ray fixator of FIG. 38 and the cut guide of FIG. 56 removed from the metatarsal and cuneiform scaffolds.

The first sliding member 278*a* includes a first release arm 278*c* and the second sliding member 278*b* includes a second release arm 278*d* that translate relative to the compression-distraction tool 220 as the compression-distraction tool 220 is secured to the first ray fixator 250. The first and second release arms 278*c*, 278*d* of the attachment mechanism 278 have chamfered ends that interact with the engagement pins 282*a*, 282*b* such that when the engagement pins 280 are fully positioned in the metatarsal and cuneiform holes 274*a*, 276*a*, the corresponding chamfered ends of the first and second release arms 278*c*, 278*d* translate downward and applies an inward force on the corresponding cylindrical ends of the locking buttons 282*a*, 282*b* as shown in FIG. 57A.

When locking buttons 282*a*, 282*b* have been depressed by the chamfered ends of the first and second release arms 278*c*, 278*d* of the attachment mechanism 278 causing both spring plunger cylindrical ends to retract into the cut guide aperture 250*c*, the cut guide aperture 250*c* is released for sliding medially and away from the compression-distraction tool 220 and out of engagement with the metatarsal and cuneiform scaffolds 250*a*, 250*b*. This movement disassembles the first ray fixator 250 such that the metatarsal and cuneiform scaffolds 250*a*, 250*b* may be utilized with the compression-distraction tool 220 to compress or distract the joint. Because the compression-distraction tool 220 is now locked onto the metatarsal and cuneiform scaffolds 250*a*, 250*b*, the alignment of the first metatarsal 30 relative to the medial cuneiform 32 with the prepared ends is preserved and the tarsometatarsal joint can be distracted or compressed by actuating the driving know 268*b*.

As is described above, prior to or during the engagement of the compression-distraction tool 220 to the first ray fixator 250, the locking mechanism 212 of the second preferred embodiment that is associated with the metatarsal scaffold 250*a* may be released or loosened to allow frontal plane rotation of the first metatarsal 30 (i.e., rotation of the metatarsal k-wires 14 within the slots 212*a*) to change the rotational orientation of the first metatarsal 30 relative to the medial cuneiform 32.

In operation, the use of the second preferred embodiment of the surgical instruments 210 preferably corrects alignment of the patient's bones at the TMT joint. After resecting the connective tissues of the first tarsometatarsal joint or TMT joint, and with the first metatarsal 30 in the deformed state, the first ray fixator 250 is placed on the dorsal aspect of the first metatarsal 30 with the positioning paddle 56*a* against the head of the first metatarsal 30. The vertical leg 266*b* of the metatarsal alignment wire 266 is used to aid aligning the first ray fixator 250 in a dorsal orientation relative to the first metatarsal 30 using the perfect circle method and the horizontal leg 266*a* of the metatarsal alignment wire 266 is used to aid in aligning the first ray fixator 250 with the long axis 30*a*.

Once the position of the first ray fixator 250 is satisfactory in accordance with the determination of the medical professional, bone wires or k-wires 14 are inserted into the medial aspect of slots 212*a*1, 212*a*2 in the locking mechanism 212 of the metatarsal scaffold 250*a*. After the wires 14 are inserted, a driver or other tool is used to rotate the actuation screw or actuation mechanism 212*b* clockwise to secure the first ray fixator 250 to the k-wires 14 and thereby the first metatarsal 30. The surgeon or other medical professional then determines an amount of the metatarsal base to cut from the first metatarsal 30. If the cut guide 56 that is pre-installed in the cut guide aperture 250*c* is not the correct size, this initial cut guide 56 is remove and another of a plurality of other sizes of the cut guide 56 is selected and positioned in the cut guide aperture 250*c*. The cut guide 56 is preferably inserted into the cut guide aperture 250*c* so that the cut guide slot 56*b* is on the metatarsal side of the positioning paddle 56*a*. After cutting the desired amount of the metatarsal base from the metatarsal 30, the cut guide 56 is removed from the cut guide aperture 250*c* and the cut bone portion is removed from the joint. The cut guide 56 is rotated one-hundred eighty degrees relative to the cut guide aperture 250*c* and is reinserted into the cut guide aperture 250*c*. The cut guide slot 56*b* is now on the cuneiform side of the positioning paddle 56*a*. The first metatarsal 30 is then repositioned to the desired anatomically correct orientation relative to the second metatarsal 44 and the medial cuneiform 32. The longitudinal leg 254*a* of the alignment arm 254, preferably in combination with a fluoroscope, is used to orient the first metatarsal 30 with the second metatarsal 44 and the vertical leg 266*b* of the metatarsal alignment wire 266 is used to align the first metatarsal 30 in the frontal plane. With the first ray fixator 250 and the first metatarsal 30 oriented as desired, two k-wires or bone wires 14 are inserted into the medial cuneiform 32 through the two holes in the cuneiform scaffold 250*b*. An amount of the distal end of the medial cuneiform 32 is then cut by the surgeon. If the cut guide 56 that is installed in the cut guide aperture 250*c* is not the correct size, the cut guide 56 is removed another one of the plurality of other sizes of the cut guide 56 is selected for insertion into the cut guide aperture 250*c*. The appropriate cut guide 56 is preferably inserted such that the cut guide slot 56*b* is on the cuneiform side of the positioning paddle 56*a*.

After cutting the desired amount of the distal end of the medial cuneiform 32, the compression-distraction tool 220 is moved or slid onto the metatarsal and cuneiform tabs 274, 276 of the metatarsal scaffold 250*a* and the cuneiform scaffold 250*b*, respectively. With the metatarsal and cuneiform tabs 274, 276 fully inserted into the sliding member and base member slots 270*b*, 272*a*, each of the first and second sliding members 278*a*, 278*b* is urged downwardly toward the metatarsal and cuneiform tabs 274, 276 to secure the compression-distraction tool 220 to the first ray fixator 250. Once both first and second sliding members 278*a*, 278*b* are fully depressed, the cut guide aperture 250*c* is urged by sliding medially away from the metatarsal and cuneiform scaffolds 250*a*, 250*b*. Because the compression-distraction tool 220 is now locked onto the first ray fixator 250, the first ray alignment is held securely in place.

The TMT joint is subsequently distracted or compressed by rotating the driving knob 268*b* on the compression-distraction tool 220 counterclockwise or clockwise, depending on whether compression or distraction is desired. If the TMT joint is distracted, the cut joint surfaces may be fenestrated or otherwise prepared for subsequent compression and fusion. If additional frontal plane rotation of the first metatarsal 30 is desired, the k-wires 14 attached to the metatarsal 30 are unlocked by rotating the actuation mechanism 212*b* on the metatarsal scaffold 250*a* counterclockwise. The metatarsal 30 may then be rotated so the k-wires 14 move across the scalloped gripping surfaces 264, 260*a* to reach the desired rotational orientation. The intermetatarsal angle is held in place as the frontal rotation is being performed. Once the desired frontal plane rotation is achieved, the k-wires 14 associated with the metatarsal scaffold 250*a* are locked by again rotating the actuation mechanism 212*b* clockwise. Preparation of the joint can be done as needed, or the joint can be compressed by rotating or pivoting the driving knob 268*b* on the compression-distraction tool 220 clockwise. With the prepared cut planes of the joint compressed, a fixation of choice can be applied to secure the first ray. Once secured, the k-wires 14 are unlocked and the surgical instruments 210 may be removed from the first metatarsal 30 and the medial cuneiform 32. The metatarsal and cuneiform scaffolds 250*a*, 250*b*, 350*a*, 350*b* may alternatively be moved in compression or distraction by connecting the scissor compression-distraction tool 20 of the first preferred embodiment thereto.

Figure 59:
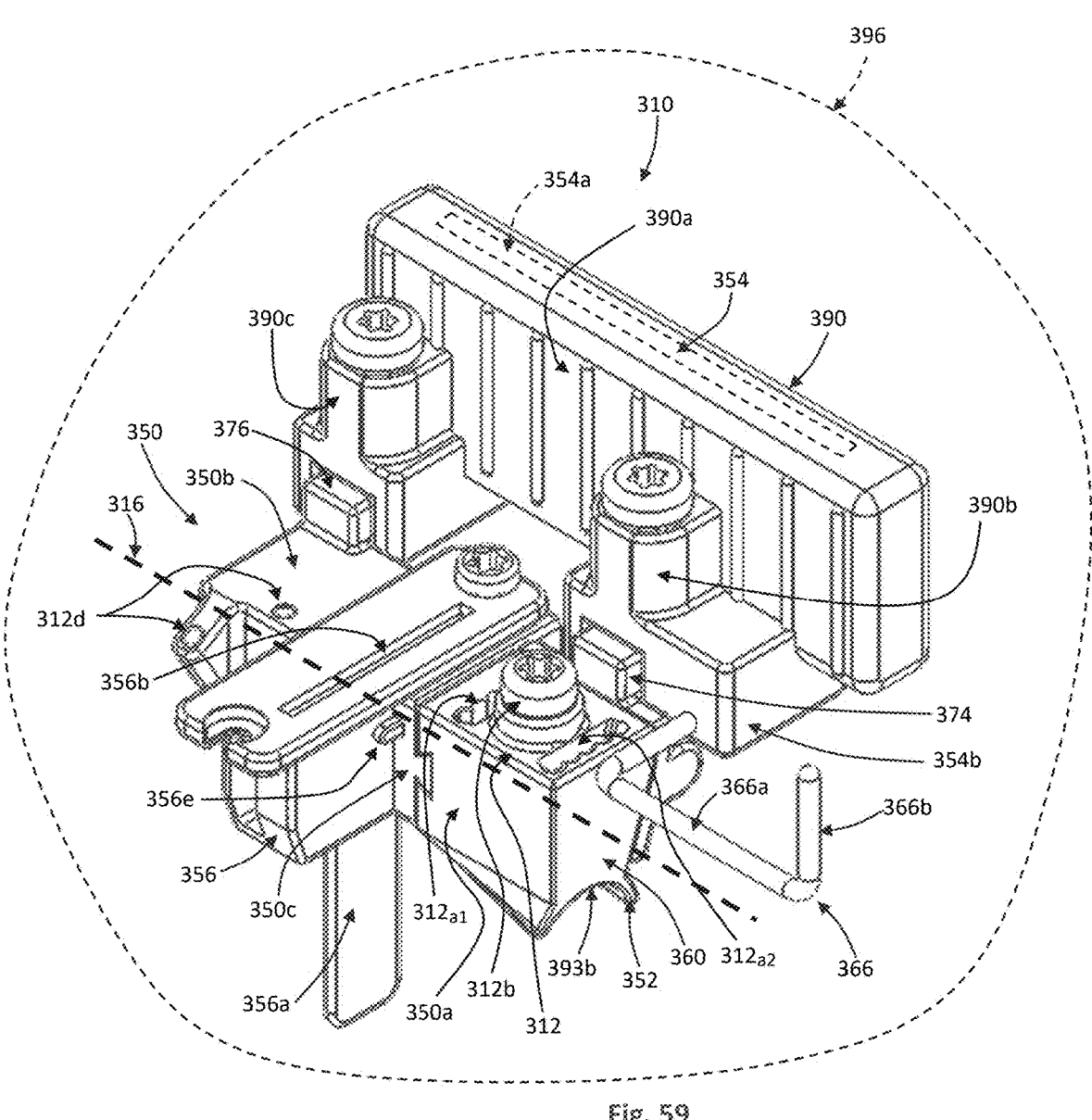
FIG. 59 illustrates a side perspective view of a first ray fixator and bridge assembly of surgical instruments in accordance with a third preferred embodiment of the present invention for bunion correction.
Figure 60:
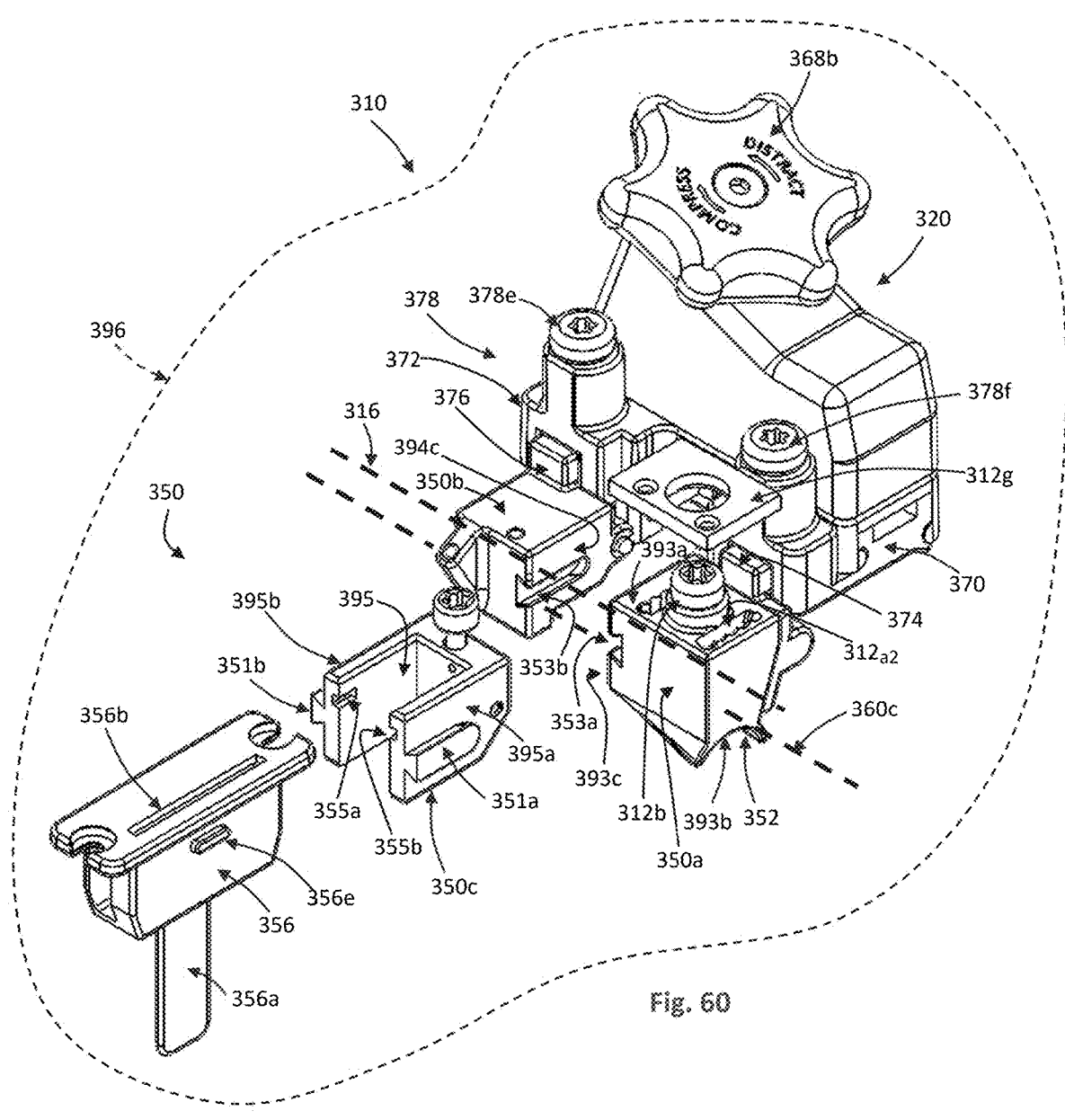
FIG. 60 illustrates a partially exploded, side perspective view of the first ray fixator of FIG. 59 and the compression-distraction tool of FIG. 37.
Figure 61:
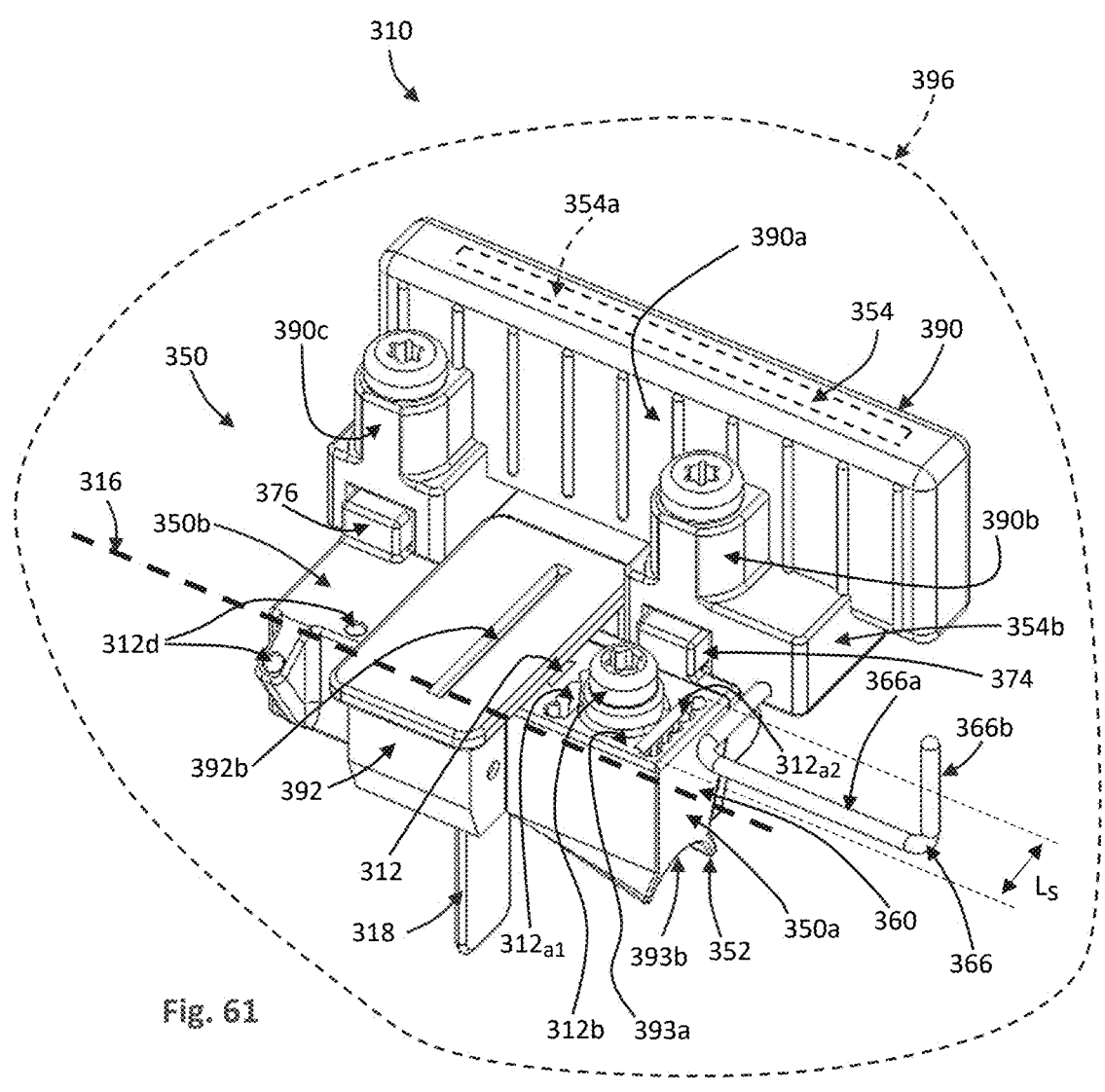
FIG. 61 illustrates a side perspective view of an alternative embodiment of the first ray fixator and bridge assembly of the surgical instruments of FIG. 59, wherein a cut guide aperture is replaced with a cut guide.

Referring to FIGS. 59-61, in a third preferred embodiment, surgical instruments 310 for bunion correction include the compression-distraction tool 320, which is substantially the same as the second preferred compression distraction tool 220, 320, a first ray fixator 350, which is substantially the same as the second preferred first ray fixator 250 and a bridge 390. The third preferred embodiment of the surgical instruments 310 is similar to the first and second preferred embodiments described above and reference numbers are utilized to identify the same or similar features of the third preferred embodiment with a "3" prefix identifying the third preferred embodiment compared to the first and second preferred embodiments.

The first ray fixator 350 of the third preferred embodiment of the surgical instruments 310 includes the metatarsal and cuneiform scaffolds 350*a*, 350*b* and the cut guide aperture 350*c* that is used with a cut guide 356 or a unitary cut guide 392 that is removably mountable between the metatarsal and cuneiform scaffolds 350*a*, 350*b*. The cut guide 356*a* preferably includes a positioning paddle 356*a* and the unitary cut guide 392 preferably includes a positioning paddle 318 that may be positioned in the joint between the proximal end of the first metatarsal 30 and the distal end of the cuneiform 32 to facilitate cutting a portion of the ends of the first metatarsal 30 and the cuneiform 32 during use. The positioning paddles 318, 356*a* are preferably positioned in the resected tarsometatarsal joint between the first metatarsal 30 and the cuneiform 32 during the preferred procedure. The cut guide aperture 350*c* preferably includes two opposing tongues 351*a*, 351*b* that are removably mountable in opposing fixator slots 353*a*, 353*b* on inside surfaces of the cuneiform scaffold 350*b* and the metatarsal scaffold 350*a*, respectively. The cut guide 356 preferably includes opposing cut guide tabs 356*e* that are removably mountable in aperture slots 355*a*, 355*b* of the cut guide aperture 350*c*. In the third preferred embodiment, the compression-distraction tool 320 includes the attachment mechanism 378, which is comprised of first and second attachment fasteners 378*e*, 378*f*. The first and second attachment fasteners 378*e*, 378*f* are removably mountable in the holes (not shown) of the metatarsal and cuneiform tabs 374, 376.

The first ray fixator 350 of the third preferred embodiment is utilized for preparing the first metatarsal 30 and the cuneiform 32 for a bunion correction procedure. The first ray fixator 350 includes the metatarsal scaffold 350*a*, the cuneiform scaffold 350*b* and the cut guide aperture 350*c* or the unitary cut guide 392. The metatarsal scaffold 350*a* has a housing with a top surface 393*a*, a bone contacting surface 393*b* and a first guide engagement surface 393*c*. The cuneiform scaffold 350*b* has a housing with a second guide engagement surface 394*c*. The metatarsal scaffold 350*a* and the cuneiform scaffold 350*b* define the longitudinal axis 316 of the first ray fixator 350 in the assembled configuration. The unitary cut guide 392 may be removably mountable to the metatarsal and cuneiform scaffolds 350*a*, 350*b* with a tongue and groove arrangement, a clip, a fastener or other attachment mechanisms or methods that facilitate removable mounting of the unitary cut guide 392 to the metatarsal and cuneiform scaffolds 230*a*, 350*b*.

In the preferred embodiments, the bone contacting surface 293*b*, 393*b* may be comprised of an arcuate bone contacting surface 293*b*, 393*b*. The arcuate bone contacting surface 293*b*, 393*b* is configured to engage the first metatarsal 30, the medial cuneiform 32, a phalange or another bone or bone fragment. The arcuate configuration of the bone contacting surface 293*b*, 393*b* may be specifically designed and configured to complement the surface of the bone where the metatarsal scaffold 250*a*, 350*a* will be mounted. The bone contacting surface 293*b*, 393*b* is not limited to having the arcuate configuration and may be generally planar, wedge-shaped or otherwise configured to positioning on the bone for attachment and manipulation of the bone or bone fragment, as is described herein.

The cut guide aperture 350*c* of the first ray fixator 350 of the third preferred embodiment has the cut guide opening 395, a first cut engagement surface 395*a* and a second cut engagement surface 395*b*. The cut guide opening 395 is oriented generally perpendicular to the longitudinal axis 316 such that the cut guide 356 may be removably insertable into the cut guide opening 395. The cut guide aperture 350*c* is removably mountable to the metatarsal scaffold 350*a* and the cuneiform scaffold 350*b* by engaging the first guide engagement surface 393*c* with the first cut engagement surface 395*a* and the second guide engagement surface 394*c* with the second cut engagement surface 395*b*. In the third preferred embodiment, the first and second cut engagement surfaces 395*a*, 395*b* include the opposing tongues 351*a*, 351*b* and the first and second guide engagement surfaces 393*c*, 394*c* include the opposing fixator slots 353*a*, 353*b* to releasably mount the cut guide aperture 350*c* to the metatarsal scaffold 350*a* and the cuneiform scaffold 350*b*.

In the third preferred embodiment, the first guide engagement surface 393*c* includes a first groove or fixator slot 353*a* and the first cut engagement surface 395*a* includes a first tongue 351*a* of the opposing tongues 351*a*, 351*b*. The first tongue 351*a* is slidably engageable with the first groove or fixator slot 353*a* to engage and disengage the cut guide aperture 350*c* with the metatarsal scaffold 350*a*. The first tongue 351*a* may alternatively be positioned on the first guide engagement surface 393*c* and the first groove or fixator slot 353*a* may be positioned on the first cut engagement surface 395*a* without significantly impacting the function and operation of connection of the cut guide aperture 350*c* to the metatarsal scaffold 350*a*. In addition, the cut guide aperture 350*c* may be otherwise connectable to the metatarsal scaffold 350*a* by fasteners, adhesive bonding, clamping, integral formation or otherwise. The second guide engagement surface 394*c* preferably includes a second groove or fixator slot 353*b* and the second cut engagement surface 395*b* includes a second tongue 351*b*. The second tongue 351*b* is slidably engageable with the second groove or fixator slot 353*b* to assist with engagement and disengagement of the cut guide aperture 350*c* with the metatarsal scaffold 350*b*. The second groove or fixator slot 353*b* and the second tongue 351*b* may similarly be switched to the second cut engagement surface 395*b* and the second guide engagement surface 394*c*, respectively, without significantly impacting the operation of the cut guide aperture 350*c*, the metatarsal scaffold 350*a* and the cuneiform scaffold 350*b*.

The cut guide aperture 350*c* of the third preferred embodiment includes the first tongue 351*a* on the first side or first cut engagement surface 395*a* and the second tongue 351*b* on the second side or second cut engagement surface 395*b*. The metatarsal side or scaffold 350*a* includes the first groove or fixator slot 353*a* and the cuneiform side or scaffold 350*b* includes the second groove or fixator slot 353*b*. The first tongue 351*a* is positioned in the first groove 353*a* and the second tongue 351*b* is positioned in the second groove 353*b* in the assembled configuration (FIG. 59).

Referring to FIGS. 38 and 55-58, the cut guide aperture 250*c* may include the first and second cut engagement surfaces 295*a*, 295*b* with the first and second opposing tongues 251*a*, 251*b*, respectively, that slidably engage with the first and second guide engagement surfaces 393*c*, 394*c* into the first and second grooves or fixator slots 253*a*, 253*b* to selectively connect the cut guide aperture 250*c* with the cuneiform and metatarsal scaffolds 250*a*, 250*b*. The cut guide aperture 250*c* of the second preferred embodiment includes the first locking button 282*a* extending from the first cut engagement surface 295*a* and the second locking button 282*b* extending from the second cut engagement surface 295*b*. The first and second locking buttons 282*a*, 282*b* are biased toward an extended configuration (FIG. 56) and are moveable to a depressed configuration. The first and second locking buttons 282*a*, 282*b* are positioned proximate a distal end of the cut guide aperture 250*c*. The third preferred cut guide aperture 350*c* may include the locking buttons 282*a*, 282*b* and have a similar configuration for connection and securing to the metatarsal scaffold and the cuneiform scaffold 350*a*, 350*b* as the second preferred cut guide aperture 250*c* without significantly impacting the function and operation of the third preferred first ray fixator 350.

The second preferred metatarsal scaffold 250*a* may include an inner metatarsal edge 267*a* proximate a distal end of the first guide engagement surface 293*c* and the cuneiform scaffold 250*b* may include an inner cuneiform edge 267*b* proximate a distal end of the second guide engagement surface 294*c*. The first locking button 282*a* is located proximate and inwardly relative to the inner metatarsal edge 267*a* and the second locking button 282*b* is located proximate and inwardly relative to the inner cuneiform edge 267*b* in the assembled configuration (FIG. 55) and inhibits disengagement of the cut guide aperture 250*c* from the metatarsal and cuneiform scaffolds 250*a*, 250*b* in the assembled configuration. The cut guide aperture 250*c* is not limited to being locked or secured to the metatarsal and cuneiform scaffolds 250*a*, 250*b* by the first and second locking buttons 282*a*, 282*b* and may be otherwise designed and configured for removable connection to the metatarsal and cuneiform scaffolds 250*a*, 250*b*, such as by fastening, adhesive bonding, clamping or otherwise securing the cut guide aperture 250*c* to the metatarsal and cuneiform scaffolds in the assembled configuration.

Referring to FIGS. 59 and 61, in the third preferred embodiment, the surgical instruments 310 may include the bridge 390. The bridge 390 includes a body 390*a*, a first attachment stub 390*b* positioned at a first side of the body 390*a* and a second attachment stub 390*c* positioned at a second opposite side of the body 390*a*. The metatarsal scaffold 350*a* includes the metatarsal tab 374 and the cuneiform scaffold 350*b* includes the cuneiform tab 376. The first attachment stub 390*b* is fixed to the metatarsal tab 374 and the second attachment stub 390*c* is fixed to the cuneiform tab 376 in the assembled configuration (FIGS. 59 and 61) to provide stability to the first ray fixator 350 in the assembled configuration. The first and second attachment stubs 390*b*, 390*c* may include attachment fasteners to selectively secure the bridge 390 to the first ray fixator 350. The bridge 390 may also be utilized as a handle for the surgeon to manipulate the first ray fixator 350 into position relative to the first metatarsal 30 during operation. The alignment arm 354 may extend from the bridge 390, may be comprised of the bridge 390 or may be encased or embedded in the bridge 390 such that the longitudinal leg 354*a* may be viewed under fluoroscopy to align the longitudinal leg 354*a* with the second metatarsal 44. The alignment arm 354 of the third preferred embodiment includes the longitudinal leg 354*a* embedded in the body 390*a* of the bridge 390 and the lateral leg 354*b* comprised of portions of the body 390*a* and the first and second attachment stubs 390*b*, 390*c* that position the longitudinal leg 354*a* laterally relative to the first ray fixator 350. The alignment arm 354 is, incorporated into the bridge 390 that is removably mountable to the metatarsal side or scaffold 350*a* and the cuneiform side or scaffold 350*b*. The metatarsal alignment wire 366 of the third preferred embodiment extends from the bridge 390 and includes the horizontal leg 366*a* that extends generally parallel relative to the longitudinal axis 316 of the first ray fixator 350 and the vertical leg 366*b* that extends generally perpendicular to the longitudinal axis 316. The vertical leg 366*b* preferably extends from the horizontal leg 366*a* generally perpendicular to the top surface 393*a* of the metatarsal scaffold 350*a*. The metatarsal alignment wire 366 is not limited to extending form the bridge 390 and may extend from the metatarsal scaffold 350*a* or another component of the third preferred surgical instruments 310.

The third preferred metatarsal scaffold 350*a* preferably includes the locking mechanism 312 having the first and second slots 312*a*1, 312*a*2 that are oriented generally perpendicular relative to the longitudinal axis 316 and the k-wire guide cap 312*g*. The first and second slots 312*a*1, 312*a*2 are configured to receive a portion of the first and second k-wires 14 therein, respectively, to secure the metatarsal scaffold 350*a* to the first metatarsal 30. The locking mechanism 312 is similarly designed and configured in comparison to the second preferred locking mechanism 212. The first slot 312*a*1 is associated with the first locking lever 212*e*$_1$ and the second slot 312*a*2 is associated with the second locking lever 212*e*$_2$ such that the first slot 312*a*1 and the first locking lever 212*e*$_1$ engage the portion of the first k-wire 14 and the second slot 312*a*2 and the second locking lever 212*e*$_2$ engage the portion of the second k-wire 14 in a locked configuration to secure the metatarsal scaffold 350*a* to the first metatarsal 30 during operation.

Referring to FIGS. 38-61, the second and third preferred embodiments of the surgical instruments 210, 310 include the locking mechanism 212, 312 for securing the metatarsal scaffold 250*a*, 350*a* or nearly any orthopedic device to a bone or bone fragment, such as the first metatarsal 30, through the wires 14. The locking mechanisms 212, 312 of the second and third embodiment are substantially the same and components and reference numbers for the locking mechanism 212 of the second preferred embodiment are described herein for clarity with the understanding that the locking mechanism 312 of the third preferred embodiment is substantially the same as the locking mechanism 212 of the second preferred embodiment. The locking mechanism 212, 312 includes the housing or scaffold housing 260 having the top surface 293a, 393a and the bone contacting surface 293b, 393b opposite the top surface 293a, 393a. The housing or scaffold housing 260, 360 defines a long locking axis 260c, 360c that extends generally parallel to the longitudinal axis 216, 316. The locking mechanism 212, 312 also includes the first and second slots 212a1, 212a2, 312a1, 312a2 extend between the top surface 293a, 393a and the bone contacting surface 293b, 393b through the housing 260, 360. The first and second slots 212a1, 212a2, 312a1, 312a2 extend generally perpendicular to the long locking axis 260c, 360c.

The first and second slots 212a1, 212a2, 312a1, 312a2 of the locking mechanism 212, 312 have a slot length $L_S$ and a slot width $W_S$. In the preferred embodiments, the slot length $L_S$ is two and one-half (2½) to ten (10) times greater than the slot width $W_S$ or the slot length $L_S$ may be approximately five time greater than the slot width $W_S$. The slot length $L_S$ is not limited to being any specific ratio greater than the slot width $W_S$ but is preferably greater than the slot width $W_S$ to permit the wires 14 to pivot relative to or about the long locking axis 260c, 360c in the first and second slots 212a1, 212a2, 312a1, 312a2 when the bone fasteners or wires 14 are positioned in the first and second slots 212a1, 212a2, 312a1, 312a2 and the locking mechanism 212, 312 is in the unlocked configuration. The preferred first and second slots 212a1, 212a2, 312a1, 312a2 may also include a top slot length $L_{ST}$ proximate the top surface 293a, 393a and a bottom slot length $L_{SB}$ proximate the bone contacting surface 293b, 393b. The top slot length $L_{ST}$ is greater than the bottom slot length $L_{SB}$ to accommodate the pivoting of the wires 14 in the first and second slots 212a1, 212a2, 312a1, 312a2 when the first metatarsal 30 is pivoted relative to the scaffold housing 260, 360 during use. The top and bottom slot lengths $L_{ST}$, $L_{SB}$ are not limited to this configuration and may be the same or substantially equivalent but configuring the top slot length $L_{ST}$ to be greater than the bottom slot length $L_{SB}$ is preferred to accommodate the pivoting of the wires 14 in the first and second slots 212a1, 212a2, 312a1, 312a2.

The first and second slots 212a1, 212a2, 312a1, 312a2 also preferably include first and second slot gripping surfaces 260a1, 260a2 that are formed on the scaffold housings 260, 360 and preferably face each other within the scaffold housing 260, 360. The first and second slot gripping surfaces 260a1, 260a2 are preferably comprised of scalloped gripping surfaces that are designed and configured to engage and hold the shafts of the wires 14 to secure the wires 14 to the scaffold housing 260, 360 in the locked configuration.

The locking mechanism 212, 312 also includes a first locking lever 212e1 and a second locking lever 212e2 positioned in the housing or scaffold housing 260, 360 between the top surface 293a, 393a and the bone contacting surface 293b, 393b in the assembled configuration. The first locking lever 212e1 includes a first lock gripping surface 264a and the second locking lever 212e2 including a second lock gripping surface 264b. The first slot gripping surface 260a1 faces the first lock gripping surface 264a and the second slot gripping surface 260a2 faces the second lock gripping surface 264b in the assembled configuration (FIGS. 39 and 42-45). The spacing of the first slot and lock gripping surfaces 260a1, 264a and the second slot and lock gripping surfaces 260a2, 264b generally define the first and second slots 212a1, 212a2, 312a1, 312a2 for positioning and engagement of the wires 14. In the preferred embodiments, the The first and second slot gripping surfaces 260a1, 260a2 and the first and second lock gripping surfaces 264a, 264b are preferably scalloped, but are not so limited. The first and second slot gripping surfaces 260a1, 260a2 and the first and second lock gripping surfaces 264a, 264b may be otherwise designed and configured to engage and secure the bone fasteners or wires 14 to the scaffold housing 260, 360 in the locked configuration. The first and second slot gripping surfaces 260a1, 260a2 and the first and second lock gripping surfaces 264a, 264b may, for example, include knurled surfaces, roughened surfaces, surface treatments or other designs that facilitate engagement of the wires 14 with the first and second slot gripping surfaces 260a1, 260a2 and the first and second lock gripping surfaces 264a, 264b in the locked configuration.

In the preferred embodiments, the first lock gripping surface 264a includes a first scalloped surface and the first scalloped surface has a first scallop radius. The first scallop radius is configured to engage a surface of the wire 14 to secure the wire 14 to the scaffold housing 260, 360 in the locked configuration. The scallop radius is preferably designed and configured to facilitate engagement of typical k-wires 14 used during the bunion correction surgery. The second lock gripping surface 264b and the first and second slot gripping surfaces 260a1, 260a2 also preferably include the scalloped surfaces with the scallop radii for engagement of the wires 14. The scalloped surfaces of the first and second lock gripping surface 264a, 264b and the first and second slot gripping surfaces 260a1, 260a2 have a generally fan-like configuration, thereby defining the top and bottom slot lengths $L_{ST}$, $L_{SB}$ to facilitate the pivoting of the wires 14 relative to the scaffold housing 260, 360 and securing the wires 14 to the scaffold housing 260, 360. The scalloped surfaces are not limited to having the fan-like configuration and may be otherwise designed and configured, but the fan-like configuration is preferred to facilitate the typical pivoting and movement of the first metatarsal 30 relative to the medial cuneiform 32 in the bunion correction surgery.

The locking mechanism 212, 312 further includes a wedge 212f positioned between the first and second locking levers 212e1, 212e2 in the housing 260, 360 and an actuation mechanism 212b, 312b configured for manipulation by a user to move the wedge 212f and the first and second locking levers 212e1, 212e2. The actuation mechanism 212b, 312b is preferably exposed at the top surface 293a, 393a for accessibility by the user and preferably for engagement by a tool (not shown) to drive the movement of the locking mechanism 212, 312 to and between the locked and unlocked position or configuration. The actuation mechanism 212b, 312b is specifically movable such that the first lock gripping surface 264a and the second lock gripping surface 264b move at least along the long locking axis 260c, 360c toward or away from the first and second slot gripping surfaces 260a1, 260a2, respectively. In the preferred embodiments, the actuation mechanism 212b, 312b moves the wedge 212f generally vertically perpendicular to the long locking axis 260c, 360c such that its opposing wedge surfaces interact with rear surfaces of the first and second locking levers 212e1, 212e2 to move the first and second locking levers 212e1, 212e2 concurrently upward and toward the opposing first and second slot gripping surfaces 260a1, 260a2 to engage the wires 14 between the first and second lock gripping surfaces 264a, 264b and the first and second slot gripping surfaces 260a1, 260a2, respectively. The wedge 212f and first and second locking levers 212e1, 212e2 are not limited to operating in this specific manner and may be otherwise designed and configured to facilitate engagement and locking of the wires 14, such as by flipping the wedge 212f such that downward motion urges the first and second locking levers $212e_1$, $212e_2$ toward each other, direct outward force is applied to the first and second locking levers $212e_1$, $212e_2$ to accomplish locking or other mechanisms are utilized to fix the wires 14 using the locking mechanism 212, 312.

In the second and third preferred embodiments, the actuation mechanism 212$b$, 312$b$ is comprised of an actuation screw that is threadably secured to the wedge 212$f$. The wedge 212$f$ preferably includes a threaded hole into which the threads on the shaft of the actuation screw 212$b$, 312$b$ extend to urge the wedge 212$f$ generally up and down in the scaffold housing 260, 360 to move the first and second locking levers $212e_1$, $212e_2$. The actuation screw 212$b$, 312$b$ preferably has a tool fitting on its top surface for engagement by a tool to drive the rotation of the actuation screw 212$b$, 312$b$. The actuation mechanism 212$b$, 312$b$ is not limited to being comprised as the actuation screw and may be otherwise designed and configured to move the first and second locking levers $212e_1$, $212e_2$. The actuation mechanism 212$b$, 312$b$ may be comprised of an alternative actuator, such as a cam-lever that is attached to the wedge 212$f$ to raise and lower the wedge 212$f$ in the metatarsal scaffold housing 260, 360 or other mechanisms or methods that are able to move the wedge 212$f$ upwardly and downwardly.

When operating the preferred locking mechanism 212, 312, the first locking lever $212e_1$ moves toward the top surface 293$a$, 393$a$ and toward the first slot gripping surface $260a_1$ and the second locking lever $212e_2$ moves toward the top surface 293$a$, 393$a$ and toward the second slot gripping surface $260a_2$ when the actuation mechanism 212$b$, 312$b$ is moved in the locking direction. In contrast, the first locking lever $212e_1$ moves toward the bone contacting surface 293$b$, 393$b$ and away from the first slot gripping surface $260a_1$ and the second locking lever $212e_2$ moves toward the bone contacting surface 293$b$, 393$b$ and away from the second slot gripping surface $260a_2$ when the actuation mechanism 212$b$, 312$b$ is moved in an unlocking direction.

Referring to FIGS. 23-34, 38-51, 55, 56 and 58-61, the first ray fixator 50, 250, 350 is used for preparing the first metatarsal 30 and the cuneiform 32 for the bunion correction procedure. The first ray fixator 50, 250, 350 includes the metatarsal side or scaffold 50$a$, 250$a$, 350$a$, the cuneiform side or scaffold 50$b$, 250$b$, 350$b$ and the cut guide aperture 50$c$, 250$c$, 350$c$ positioned between the metatarsal side or scaffold 50$a$, 250$a$, 350$a$ and the cuneiform scaffold 50$b$, 250$b$, 350$b$. The metatarsal and cuneiform scaffolds 50$a$, 50$b$, 250$a$, 250$b$, 350$a$, 350$b$ and the cut guide aperture 50$c$, 250$c$, 350$c$ may be uniformly constructed, such as in the first ray fixator 50 of the first preferred embodiment, or may be comprised of an assembly, such as in the first ray fixator 250, 350 of the second and third preferred embodiments.

The metatarsal side 50$a$, 250$a$, 350$a$ is preferably comprised of the metatarsal scaffold 50$a$, 250$a$, 350$a$ that is positioned above and/or on the first metatarsal 30 in the preferred procedure. The cuneiform side 50$b$, 250$b$, 350$b$ is preferably comprised of the cuneiform scaffold 50$b$, 250$b$, 350$b$ that is positioned above and/or on the medial cuneiform 32 in the preferred procedure. The metatarsal scaffold 250$a$, 350$a$ and the cuneiform scaffold 250$b$, 350$b$ of the second and third preferred embodiments is removably mountable to the cut guide aperture 250$c$, 350$c$ such that the first ray fixator 250, 350 may be assembled and disassembled for use during the procedure, as is described herein.

The cut guide aperture 50$c$ may include the retention clip 58 attached thereto that is configured to removably retain the cut guide 56 in the cut guide aperture 50$c$, such as in the first preferred embodiment. The second and third preferred embodiments of the cut guide aperture 250$c$, 350$c$ may also include the retention clip 58 to releasably secure the cut guide 356 therein but may also include alternative connection mechanisms to retain the cut guide 56, 356 in the cut guide aperture 50$c$, 250, 350$c$. The retention clip 58 may, for example, be comprised of a screw that secures the cut guide 56, 356 in the cut guide aperture 50$c$, 250$c$, 350$c$. In addition, the cut guide 56, 356 may alternatively be secured to the cut guide aperture 50$c$, 250$c$, 350$c$, for example, the third preferred embodiment of the cut guide 356 includes the opposing tabs 356$e$ that slide into the aperture slots 355$a$ to secure the cut guide 356 in the cut guide aperture 350$c$.

The first ray fixator 50, 250, 350 also preferably includes first and second metatarsal slots or holes 12$d$, $212a_1$, $212a_2$, $312a_1$, $312a_2$ extending through the metatarsal side or scaffold 50$a$, 250$a$, 350$a$ between the top surface 93$a$, 293$a$, 393$a$ and a bone contacting surface 93$b$, 293$b$, 393$b$ of the metatarsal side or scaffold 50$a$, 250$a$, 350$a$. The bone contacting surface 93$b$, 293$b$, 393$b$ does not necessarily contact the patient's bone during the procedure, such as the first metatarsal 30, but is generally the surface of the metatarsal side or scaffold 50$a$, 250$a$, 350$a$ that is closest to the patient's bone when the first ray fixator 50, 250, 350 is mounted to the bone. The first and second metatarsal slots or holes 12$d$, $212a_1$, $212a_2$, $312a_1$, $312a_2$ are configured to receive wires or fasteners 14 to connect the metatarsal side or scaffold 50$a$, 250$a$, 350$a$ to the adjacent bone, such as the first metatarsal 30.

The first and second metatarsal slots $212a_1$, $212a_2$, $312a_1$, $312a_2$ may be associated with the metatarsal side locking mechanism 212, 312 that is configured to engage and disengage the metatarsal side or scaffold 250$a$, 350$a$ with the first and second metatarsal wires 14 positioned in the first and second metatarsal slots $212a_1$, $212a_2$, $312a_1$, $312a_2$. Alternatively, the wires 14 may be positioned in the holes 12$d$ of the first preferred embodiment in the metatarsal side or scaffold 50$a$ for engagement with the bone.

The first ray fixator 50, 250, 350 further includes a cuneiform hole 12$d$, 212$d$, 312$d$ extending through the cuneiform side or scaffold 50$b$, 250$b$, 350$b$ between the top surface of the cuneiform side 50$b$, 250$b$, 350$b$ and a bone contacting surface of the cuneiform side 50$b$, 250$b$, 350$b$. Each of the preferred embodiments include two cuneiform holes 12$d$, 212$d$, 312$d$ in the cuneiform side 50$b$, 250$b$, 350$b$, although the first ray fixator 50, 250, 350 is not so limited and may include a single cuneiform hole or multiple holes 12$d$, 212$d$, 312$d$ for receiving cuneiform side wires 14 to secure the cuneiform side 50$b$, 250$b$, 350$b$ to the underlying bone or alternative securing features, such as clamps, adhesive bonding, straps or other features to secure the cuneiform side 50$b$, 250$b$, 350$b$ to the underlying bone, preferably the medial cuneiform 32 in the preferred procedure. In the second and third preferred embodiments, the cuneiform side or scaffold 250$b$, 350$b$ includes a first hole 212$d$, 312$d$ that extends generally perpendicularly through the top surface and an angled hole 212$d$, 312$d$ that extends at an angle relative to the top surface. Both the cuneiform holes 212$d$, 312$d$ in the second and third preferred cuneiform side 250$b$, 350$b$ are configured to direct and guide the wire 14 into the underlying bone, such as the medial cuneiform 32, to secure the cuneiform side 250$b$, 350$b$ to the bone.

The first ray fixator 50, 250, 350 also defines the longitudinal axis 16, 216, 316 and includes the alignment arm 54, 254, 354 having the longitudinal leg 54$a$, 254$a$, 354$a$. The alignment arm 54, 254, 354 includes the lateral leg 54$b$, 254$b$, 354$b$ that is attached to the first ray fixator 50, 250, 350. The longitudinal leg 54a, 254a, 354a is spaced laterally from the metatarsal side or scaffold 50a, 250a, 350a, the cuneiform side or scaffold 50b, 250b, 350b and the cut guide aperture 50c, 250c, 350c or generally toward the second metatarsal 44 when the first ray fixator 50, 250, 350 is mounted to the first metatarsal 30 in the preferred bunion correction procedure. The longitudinal leg 54a, 254a, 354a is oriented generally parallel to the longitudinal axis 16, 216, 316 and is configured to orient the first metatarsal 44 relative to the second metatarsal 44 having the second metatarsal long axis 44a.

The alignment arm 54, 254, 354 of the preferred embodiments or the alignment guide 42 includes a lateral leg 42b, 54b, 254b, 354b that is fixed to the cuneiform side or scaffold 50b, 250b, 350b or the bridge 390 that spaces the longitudinal leg 42a, 54a, 254a, 354a laterally from the first ray fixator 50, 250, 350. The lateral leg 42b, 54b, 254b, 354b spaced the longitudinal leg 42a, 54a, 254a, 354a laterally such that the longitudinal leg 42a, 54a, 254a, 354a may be readily aligned with the second metatarsal long axis 44a of the second metatarsal 44 during the preferred bunion correction surgery. The longitudinal leg 42a, 54a, 254a, 354a extends parallel to the longitudinal axis 16, 216, 316 and from the cuneiform side or scaffold 50b, 250b, 250b toward the metatarsal side or scaffold 50a, 250a, 350a. The lateral leg 42b, 54b, 254b, 354b is not limited to extending completely laterally or having any specific size or shape and may be comprised of nearly any structure that spaces the longitudinal leg 42a, 54a, 254a, 354a laterally from the first ray fixator 50, 250, 350. For example, the second preferred lateral leg 254b includes jogs or direction changes to avoid the cuneiform tab 276 and the third preferred lateral leg 354b is comprised of portions of the body 390a and/or the first and second attachment stubs 390b, 390c that space the longitudinal leg 354a from the first ray fixator 350. The lateral leg 42b, 54b, 254b, 354b extends or includes portions that extend generally perpendicular to the longitudinal axis 16, 216, 316 and the longitudinal leg 52b, 54b, 254b, 354b extends substantially parallel to the longitudinal axis 16, 216, 316.

The first ray fixator 250, 350 may also include the metatarsal alignment wire 366 having the horizontal leg 266a, 366a and the vertical leg 266b, 366b. The horizontal leg 266a, 366a preferably extends generally parallel to the longitudinal axis 16, 216, 316 and the vertical leg 266b, 366b extends generally perpendicular relative to the longitudinal axis 16, 216, 316 from an end of the horizontal leg 266a, 366a. the horizontal leg 266a, 366a is preferably used to align the first ray fixator 250, 350 with the first metatarsal 30 and the vertical leg 266b, 366b is preferably used when x-ray imaging the first metatarsal 30 from a dorsal perspective (FIG. 51). Positioning the vertical leg 266b, 366b to form a perfect circle and visualizing the sesamoid bones provides confirmation of dorsal view alignment of the first ray fixator 250, 350 relative to the first metatarsal 30 or the bone or bone segment. By placing the first ray fixator 250, 350, utilizing this dorsal viewpoint, such that the vertical leg 266b, 366b of the metatarsal alignment wire 266, 366 becomes a "perfect circle," dorsal placement of the first ray fixator 250, 350 can be confirmed. In the second preferred embodiment, the horizontal leg 266a may be fixed or removably secured to the metatarsal scaffold 250 and in the third preferred embodiment, the horizontal leg 366a is fixed to the bridge 390. The vertical leg 266b, 366b of the second and third preferred embodiments in spaced from the first ray fixator 250, 350 in the assembled configuration. The horizontal leg 266a, 366a is configured to align the first ray fixator 250, 350 to the first metatarsal long axis 30a of the first metatarsal 30 and the vertical leg 266b, 366b is configured to provide dorsal alignment of the first ray fixator 250, 350 with the first metatarsal 30.

Referring to FIGS. 1-61, the surgical instruments 10, 210, 310 of the preferred embodiments may be collected, provided and/or shipped as a kit. The kit may be assembled and collected specifically for preparing the first metatarsal 30 and the cuneiform 32 for the preferred bunion correction procedure but is not so limited and may be assembled and provided for alternative procedures where bones or bone fragments are prepared for realignment and fusion or for an insertion of an articulation preservation implant. The kit may include the first ray fixator 50, 250, 350 and the compression-distraction tool 20, 220, 320. The metatarsal side or scaffold 250a, 350a and the cuneiform side or scaffold 250b, 350b of the first ray fixator 250, 350 of the second and third preferred embodiments are movable relative to each other, generally parallel to the longitudinal axis 216, 316, when the cut guide aperture 250c, 350c is removed from the metatarsal and cuneiform scaffolds 250a, 350a, 250b, 350b. The metatarsal scaffold 250a, 250b and the cuneiform scaffold 250b, 350c are specifically movable toward and away from each other when the compression-distraction tool 20, 220, 320 is mounted to the metatarsal and cuneiform scaffolds 250a, 350a, 250b, 350b and the cut guide aperture 250c, 350c is detached from the metatarsal and cuneiform scaffolds 250a, 350a, 250b, 350b. The kit may also include first and second metatarsal k-wires 14 and first and second cuneiform k-wires 14 that are used to mount the first ray fixator 50, 250, 350 to the bones.

The attachment mechanisms 278, 378 of the of the second and third preferred embodiments attach the compression-distraction tool 220, 320 to the metatarsal and cuneiform scaffolds 250a, 250b, 350a, 350b and are movably mounted to the compression-distraction tool 220, 320. In the second preferred embodiment, connecting the compression-distraction tool 220, 320 to the first ray fixator 250 releases the cut guide aperture 250c from the metatarsal scaffold 250a and the cuneiform scaffold 250b for removal from the metatarsal and cuneiform scaffolds 250a, 250b. In the third preferred embodiment, the compression-distraction tool 350 is releasably mounted to the metatarsal side or scaffold 350a with a first tool screw or attachment fastener 378e and to the cuneiform side or scaffold 350b with a second tool screw or attachment fastener 378f.

The kit for preparing the first metatarsal 30 and the cuneiform 32 for the bunion correction procedure may also include the first ray fixator 50, 250, 350, the compression-distraction tool 20, 220, 320, a plurality of cut guides 29, 40, 56, 356, 392 and a sterile package 296, 396. The first ray fixator 50, 250, 350, the compression-distraction tool 20, 220, 320, the plurality of cut guides 29, 40, 56, 356, 392 are preferably positioned within the sterile package 296, 396 and configured for delivery to the user in the sterile package 296, 396. The instruments, accordingly, remain sterilized within the sterile package 296, 396 until opened by the user for the surgery. The system is not limited to including only the first ray fixator 50, 250, 350, the compression-distraction tool 20, 220, 320 and the plurality of cut guides 29, 40, 56, 356, 392 cut guides in the sterile package 296, 396 and may include less than each of these instruments or additional instruments and/or tools, such as the k-wires 14, the bridge 390, tools for drilling holes in the bones and/or cutting the bones, tools for resecting the related joint, tools for manipulating the instruments, first and second metatarsal and cuneiform wires 14 or other tools, devices or instruments that may be utilized for the preferred procedure.

The preferred kit for conducting the tarsometatarsal joint arthrodesis to orient the first metatarsal 30 relative to the cuneiform 32 may also include the cut guide 29, 56, 356, 392 having the positioning paddle 18, 56a, 356a, 318 and the cut guide slot 34, 56b, 356b, 392b. The positioning paddle 18, 56a, 356a, 318 is positioned substantially parallel to the cut guide slot 34, 46b, 356b, 392b and the cut guide 29, 56, 356, 392 may include a retention mechanism to retain the cut guide 29, 56, 356, 392 in the cut guide aperture 50c, 250c, 350c and the metatarsal and cuneiform scaffolds 250a, 350a, 250b, 350b in the assembled configuration. The retention mechanism may be comprised of the engagement slot 56d of the first preferred embodiment that is engaged by the retention clip 58 in the assembled configuration, the tabs 356e that are positioned in the first and second aperture slots 355a, 355b of the third preferred embodiment or additional connection mechanisms or methods to retain the cut guide 29, 56, 356, 392 in the cut guide aperture 50c, 250c, 350c in the assembled configuration for cutting the associated bones. The kit may also include the four bone fasteners or wires 14, preferably two metatarsal wires 14 and two cuneiform wires 14 to secure the first ray fixator 50, 250, 350 to the bones.

In a preferred procedure for conducting the tarsometatarsal joint arthrodesis to orient the first metatarsal 30 relative to the medial cuneiform 32, the metatarsal scaffold or side 50a, 250a, 350a is secured to a dorsal side of the first metatarsal 30. The metatarsal scaffold 50a, 250a, 350a is preferably assembled as part of the first ray fixator 50, 250, 350 when secured to the first metatarsal 30 with the cuneiform side or scaffold 50b, 250b, 350b and the cut guide aperture 50c, 250c, 350c or the unitary cut guide 392. Once the joint is resected, the cut guide 29, 56, 356, 392 is positioned with the positioning paddle 18, 56a, 318, 356a in the tarsometatarsal joint and near a proximal end of the first metatarsal 30. The cut guide 29, 56, 356, 392 is attachable to the cut guide aperture 50c, 250c, 350c or directly to the metatarsal and cuneiform scaffolds 250a, 350a, 250b, 350b. The proximal end of the first metatarsal 30 is then cut with assistance of the cut guide 29, 56, 356, 392 to prepare the proximal end of the first metatarsal 30 for fusion and/or fixation with an implant. The first metatarsal 30 is oriented relative to the medial cuneiform 32 and the second metatarsal 44. The first metatarsal 30 may be oriented relative to the medial cuneiform 32 by aligning the longitudinal leg 42a, 54a, 254a, 354a with the second metatarsal long axis 44a and pivoting or rotating the first metatarsal 30 and the first metatarsal long axis 30a until the vertical leg 266b, 366b is in the perfect circle orientation in the dorsal view of the patient's foot.

Once the first metatarsal 30 is oriented relative to medial cuneiform 32 and the second metatarsal 44, the cuneiform scaffold 50a, 250a, 350a is fixed to the dorsal side of the medial cuneiform 32, preferably utilizing the cuneiform wires 14. The position of the first metatarsal 30 is fixed relative to the medial cuneiform 32 by fixing the cuneiform scaffold 50b, 250b, 350b to the cuneiform 32. The cut guide aperture 250c, 350c or unitary cut guide 392, may then be removed from the metatarsal and cuneiform scaffolds 250a, 350a, 250b, 350b after the compression-distraction tool 20, 220, 320 is attached to the metatarsal and cuneiform scaffolds 250a, 350a, 250b, 350b to compress or distract the first metatarsal 30 relative to the cuneiform 32. For example, the first metatarsal 30 may be distracted relative to the cuneiform 32, an implant, allograph, bone growth material or other material may be inserted between the proximal end of the first metatarsal 30, the cuneiform 32 and the first metatarsal 30 may be compressed relative to the cuneiform 32 and a bone plate or other fastening device may be secured across the first metatarsal 30 and the cuneiform 32 to fix the bones together to promote fusion.

Once the metatarsal and cuneiform scaffolds 250a, 350a, 250b, 350b are secured to the first metatarsal 30 and cuneiform 32, respectively, the bridge 390 is detached from the metatarsal and cuneiform scaffolds 250a, 350a, 250b, 350b, the cut guide aperture 250c, 350c or the unitary cut guide 392 is detached from the metatarsal and cuneiform scaffolds 250a, 350a, 250b, 350b and the compression-distraction tool 20, 220, 320 is attached to the metatarsal and cuneiform scaffolds 250a, 350a, 250b, 350b, the prepared joint, bones or bone fragments may be compressed and/or distracted. The compression-distraction tool 20, 220, 320 is preferably removably attachable to the metatarsal and cuneiform scaffolds 250a, 350a, 250b, 350b by engaging the metatarsal and cuneiform tabs 274, 374, 276, 376 in the tool slots or the base and sliding member slots 272a, 270b of the compression-distraction tool 220, 320. The compression-distraction tool 220, 320 may include an attachment mechanism with first and second sliding members 270, 370 272, 372, wherein the first sliding member or sliding member 270 engages the metatarsal tab 274, 374 and the second sliding member comprised of the base member 272, 372 engages the cuneiform tab 276, 376. The joint, bones or bone fragments are compressed and/or distracted by translating the metatarsal scaffold 250a, 350a relative to the cuneiform scaffold 250b, 350b generally along the longitudinal axis 16, 216, 316 defined by the metatarsal and cuneiform scaffolds 250a, 350a, 250b, 350b. The translation or compression and/or distraction is driven by the compression-distraction tool 20, 220, 320 by manipulating the scissor compression-distraction tool 20 of the first preferred embodiment or rotating the driving knob 268b of the second preferred embodiment. The translation of the metatarsal and cuneiform scaffolds 250a, 350a, 250b, 350b may be otherwise actuated by any compression-distraction tool that drives the translation movement of the metatarsal and cuneiform scaffolds 250a, 350a, 250b, 350b along the longitudinal axis 16, 216, 316.

In the preferred embodiments, the cut guide aperture 250c, 350c or the unitary cut guide 392 is unlocked for removal from the metatarsal and cuneiform scaffolds 250a, 350a, 250b, 350b when the compression-distraction tool 220, 320 is attached to the metatarsal and cuneiform scaffolds 250a, 350a, 250b, 350b. The attachment mechanism 278 of the compression-distraction tool 220, 320 depresses the locking buttons 282 of the cut guide aperture 250c, 350c or the unitary cut guide 392 to allow sliding of the cut guide aperture 250c, 350c or the unitary cut guide 392 out of engagement with the metatarsal and cuneiform scaffolds 250a, 350a, 250b, 350b. The cut guide 250c, 350c may be disconnected from the cut guide aperture 250c, 350c by sliding or moving generally perpendicular to the longitudinal axis 16, 216, 316, guided by the first and second tongues 251a, 251b, 351a, 351b in the opposing grooves or fixator slots 353a, 353b.

The first ray fixator 250, 350 is preferably attached to the first metatarsal 30 by the first and second metatarsal k-wires 14. The metatarsal k-wires 14 are fixed to the dorsal side of the first metatarsal 30 with the first metatarsal k-wire 14 positioned in the first slot 212a₁, 312a₁ and the second metatarsal k-wire 14 positioned in the second slot 212a₂, 312a₂. Until fully locked or when unlocked, the first and second slots 212a₁, 312a₁, 212a₂, 312a₂ facilitate pivoting of the first and second k-wires 14 and the first metatarsal 30 relative to the first ray fixator 250, 350, generally about the first metatarsal long axis 30*a*. In addition, before the cuneiform scaffold 250*b*, 350*b* is secured to the cuneiform 32 with the cuneiform wires 14, the position and orientation of the first metatarsal 30 may be moved relative to the cuneiform 32 and the second metatarsal 44. The first metatarsal 30 may, accordingly, be oriented relative to the second metatarsal 44 such that the first metatarsal long axis 30*a* is generally parallel to the second metatarsal long axis 44*a* before securing the cuneiform scaffold 250*b*, 350*b* to the cuneiform with the cuneiform wires 14. The metatarsal scaffold 250*a*, 350*a* and the cuneiform scaffold 250*b*, 350*b* are preferably secured to the first metatarsal 30 and the cuneiform 32, respectively, before the cut guide aperture 250*c*, 350*c* or the unitary cut guide 392 is disconnected from the metatarsal and cuneiform scaffolds 250*a*, 250*b*, 350*a*, 350*b* to maintain the positioning and orientation of the first metatarsal 30 relative to the cuneiform 44.

The second and third preferred embodiments of the cuneiform scaffold 250*b*, 350*b* include the cuneiform holes 212*d*, 312*d* that accept the wires 14 to connect the cuneiform scaffold 250*b*, 350*b* to the cuneiform 32. The cuneiform scaffold 250*b*, 350*b* is not limited to including the holes 212*d*, 312*d* and may include a cuneiform locking mechanism (not shown) similar to the metatarsal locking mechanism 212, 312 of the second and third preferred embodiments or the locking mechanism 12 of the first preferred embodiment.

In the preferred use of the first ray fixator 50, 250, 350 for the bunion correction surgery, the longitudinal axis 16, 216, 316 of the first ray fixator 50, 250, 350 is aligned with the first metatarsal long axis 30*a* before the wires 14 are secured to the first ray fixator 50, 250, 350 or the first metatarsal 30. Once aligned with the metatarsal scaffold 50*a*, 250*a*, 350*a* positioned on the dorsal side of the first metatarsal 30, the first ray fixator 50, 250, 350 is secured to the first metatarsal 30 by inserting the wires 14 through the holes 12*d*, 36*d*, which may be comprised of the slots 12*a*, 212*a*₁, 212*a*₂, 312*a*₁, 312*a*₂, in the metatarsal scaffold 50*a*, 250*a*, 350*a* and into the first metatarsal 30. The first ray fixator 50, 250, 350 is preferably aligned with the first metatarsal 30 before inserting any of the wires 14. Alignment of the first ray fixator 50, 250, 350 with the first metatarsal 30 or any target bone or bone fragment confirms that the first ray fixator 50, 250, 350 is in the correct orientation relative to the first metatarsal 30 and, in turn, provides a substantial visual reference for the surgeon during correction to help limit the use of x-ray.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the present description.

We claim:

1. A method for conducting a tarsometatarsal joint arthrodesis to orient a first metatarsal relative to a medial cuneiform, the method comprising:

securing a metatarsal scaffold to a dorsal side of the first metatarsal, the metatarsal scaffold connected to a cuneiform scaffold by a cut guide aperture;

positioning a cut guide with a positioning paddle in the tarsometatarsal joint and near a proximal end of the first metatarsal, the cut guide attachable to the cut guide aperture;

cutting the proximal end of the first metatarsal with assistance of the cut guide;

orienting the first metatarsal relative to the medial cuneiform and a second metatarsal;

fixing the cuneiform scaffold to a dorsal side of the medial cuneiform; and fixing the position of the first metatarsal relative to the medial cuneiform by fixing the cuneiform scaffold to the cuneiform.

2. The method of claim 1, further comprising:

attaching a compression-distraction tool to the cuneiform and metatarsal scaffolds; and disconnecting the cut guide aperture from the metatarsal and cuneiform scaffolds.

3. The method of claim 2, further comprising:

translating the metatarsal scaffold relative to the cuneiform scaffold generally along a longitudinal axis defined by the metatarsal and cuneiform scaffolds, the translation being driven by the compression-distraction tool.

4. The method of claim 3, wherein the compression-distraction tool includes a driving knob, pivoting the driving knob drives the translation of the metatarsal and cuneiform scaffolds.

5. The method of claim 2, wherein the compression-distraction tool is removably attachable to the cuneiform and metatarsal scaffolds by engaging metatarsal and cuneiform tabs of the metatarsal and cuneiform scaffolds, respectively, in tool slots of the compression-distraction tool.

6. The method of claim 5, wherein the compression-distraction tool includes an attachment mechanism with first and second sliding members, the first sliding member engaging the metatarsal tab and the second sliding member comprised of a base member and engaging the cuneiform tab when the compression-distraction tool is attached to the cuneiform and metatarsal scaffolds.

7. The method of claim 2, wherein the cut guide aperture is unlocked for removal from the metatarsal and cuneiform scaffolds when the compression-distraction tool is attached to the metatarsal and cuneiform scaffolds and an attachment mechanism of the compression-distraction tool depresses locking buttons of the cut guide aperture.

8. The method of claim 2, wherein the metatarsal scaffold, the cut guide aperture, the cuneiform scaffold, the cut guide and the compression-distraction tool are packaged in a sterile package.

9. The method of claim 1, wherein the metatarsal and cuneiform scaffolds define a longitudinal axis when connected by the cut guide aperture, the cut guide aperture disconnected from the metatarsal and cuneiform scaffolds by moving generally perpendicular relative to the longitudinal axis.

10. The method of claim 1, wherein the metatarsal scaffold is secured to the dorsal side of the first metatarsal by first and second metatarsal k-wires.

11. The method of claim 10, wherein the first and second metatarsal k-wires are secured to the metatarsal scaffold by a locking mechanism.

12. The method of claim 11, wherein the locking mechanism including first and second slots, the first metatarsal k-wire positioned in the first slot and the second metatarsal k-wire positioned in the second slot, the first and second slots facilitating pivoting of the first and second k-wires and the first metatarsal, generally about a first metatarsal long axis when the locking mechanism is unlocked and the first and second k-wires are secured to the first metatarsal.

13. The method of claim 1, wherein the first metatarsal is oriented relative to the second metatarsal such that a first metatarsal long axis of the first metatarsal is generally parallel to a second metatarsal long axis of the second metatarsal.

14. The method of claim 1, further comprising:

securing the metatarsal scaffold to the first metatarsal by inserting first and second metatarsal wires into a metatarsal locking mechanism and the first metatarsal; and securing the cuneiform scaffold to the cuneiform by inserting first and second cuneiform wires into the cuneiform scaffold and the cuneiform before disconnecting the cut guide aperture from the metatarsal and cuneiform scaffolds.

15. The method of claim 14, wherein removal of the cut guide aperture exposes the tarsometatarsal joint without losing alignment of the first metatarsal relative to the cuneiform with a compression-distraction tool fixing the position of the metatarsal and cuneiform scaffolds.

16. The method of claim 1, wherein the first metatarsal is oriented relative to the medial cuneiform and the second metatarsal by orienting a long axis of an alignment arm generally in parallel with a second metatarsal long axis of the second metatarsal.

17. The method of claim 1, wherein the first metatarsal is oriented relative to the medial cuneiform by orienting a vertical leg of a metatarsal alignment wire as a perfect circle.

18. The method of claim 1, wherein the cut guide aperture includes first and second tongues and locking buttons, the metatarsal scaffold includes a first groove and the cuneiform scaffold includes a second groove, the first tongue positioned in the first groove and the second tongue positioned in the second groove when the cut guide aperture is connected to the metatarsal scaffold and the cuneiform scaffold, the locking buttons blocking removal of the cut guide aperture from the metatarsal and cuneiform scaffold.

19. The method of claim 1, wherein the first and second cuneiform wires are secured to the cuneiform scaffold and the cuneiform by inserting the first and second cuneiform wires into a cuneiform locking mechanism of the cuneiform scaffold and the cuneiform and fastening the first and second cuneiform wires to the cuneiform scaffold with the cuneiform locking mechanism.

20. The method of claim 1, further comprising:

aligning a first ray fixator comprised of the metatarsal scaffold and the cuneiform scaffold to the first metatarsal by aligning a longitudinal axis of the first ray fixator with a first metatarsal long axis; and securing the first ray fixator to the first metatarsal by inserting bone wires through holes in the metatarsal scaffold and into the first metatarsal.

21. The method of claim 20, wherein the holes in the metatarsal scaffold are comprised of first and second slots.

* * * * *